US009983124B2

(12) United States Patent
Wang et al.

(10) Patent No.: US 9,983,124 B2
(45) Date of Patent: May 29, 2018

(54) SENSOR DEVICES COMPRISING A METAL-ORGANIC FRAMEWORK MATERIAL AND METHODS OF MAKING AND USING THE SAME

(71) Applicants: Oregon State University, Corvallis, OR (US); U.S. Department of Energy, Washington, DC (US)

(72) Inventors: Alan X. Wang, Corvallis, OR (US); Chih-hung Chang, Corvallis, OR (US); Ki-Joong Kim, Corvallis, OR (US); Xinyuan Chong, Corvallis, OR (US); Paul R. Ohodnicki, Allison Park, PA (US)

(73) Assignees: Oregon State University, Corvallis, OR (US); U.S. Department of Energy, Washington, DC (US)

( * ) Notice: Subject to any disclaimer, the term of this patent is extended or adjusted under 35 U.S.C. 154(b) by 0 days. days.

(21) Appl. No.: 15/019,811

(22) Filed: Feb. 9, 2016

(65) Prior Publication Data
US 2016/0231233 A1 Aug. 11, 2016

Related U.S. Application Data

(60) Provisional application No. 62/113,967, filed on Feb. 9, 2015.

(51) Int. Cl.
*G01N 21/35* (2014.01)
*G01N 21/3504* (2014.01)
(Continued)

(52) U.S. Cl.
CPC .......... *G01N 21/3504* (2013.01); *B01J 20/06* (2013.01); *B01J 20/226* (2013.01);
(Continued)

(58) Field of Classification Search
CPC .. G01N 21/552; G01N 21/554; G01N 21/658; G01N 21/648; G01N 21/3504; G02B 6/1226; G02B 6/122
See application file for complete search history.

(56) References Cited

U.S. PATENT DOCUMENTS 8,123,834 B2   2/2012   Masel et al.
8,480,955 B2   7/2013   Yaghi et al.
(Continued)

FOREIGN PATENT DOCUMENTS

WO   WO 2013072452 A1   5/2013
WO   WO 2013137985 A1   9/2013
WO   WO 2015183090 A1 * 12/2015   ......... G01D 5/35316

OTHER PUBLICATIONS

Lu et al., "Imparting functionality to a metal-organic framework material by controlled nanoparticle encapsulation", Nature Chemistry, vol. 4, Apr. 2012, www.nature.com/naturechemistry.*
(Continued)

*Primary Examiner* — Marcus Taningco
(74) *Attorney, Agent, or Firm* — Klarquist Sparkman, LLP

(57) ABSTRACT

Disclosed herein are embodiments of sensor devices comprising a sensing component able to determine the presence of, detect, and/or quantify detectable species in a variety of environments and applications. The sensing components disclosed herein can comprise MOF materials, plasmonic nanomaterials, or combinations thereof. In an exemplary embodiment, light guides can be coupled with the sensing components described herein to provide sensor devices capable of increased NIR detection sensitivity in determining the presence of detectable species, such as gases and volatile organic compounds. In another exemplary embodiment, optical properties of the plasmonic nanomaterials combined with MOF materials can be monitored directly to
(Continued)

detect analyte species through their impact on external conditions surrounding the particle or as a result of charge transfer to and from the plasmonic material as a result of interactions with the plasmonic material and/or the MOF material.

19 Claims, 42 Drawing Sheets

(51) Int. Cl.

| | | |
|---|---|---|
| *G02B 6/122* | (2006.01) | |
| *G01N 21/552* | (2014.01) | |
| *B01J 20/22* | (2006.01) | |
| *G01N 21/359* | (2014.01) | |
| *G01N 21/77* | (2006.01) | |
| *B01J 20/06* | (2006.01) | |
| *B01J 20/28* | (2006.01) | |
| *G02B 6/12* | (2006.01) | |

(52) U.S. Cl.
CPC ... *B01J 20/28007* (2013.01); *B01J 20/28097* (2013.01); *G01N 21/359* (2013.01); *G01N 21/554* (2013.01); *G01N 21/7703* (2013.01); *G02B 6/1226* (2013.01); *G01N 2021/7709* (2013.01); *G01N 2021/7763* (2013.01); *G01N 2201/088* (2013.01); *G02B 2006/12138* (2013.01)

(56) References Cited

U.S. PATENT DOCUMENTS

| | | | |
|---|---|---|---|
| 8,735,161 B2 | 5/2014 | Yaghi et al. | |
| 2006/0038990 A1* | 2/2006 | Habib | G01N 21/658 356/301 |
| 2010/0022020 A1 | 1/2010 | Halas et al. | |
| 2011/0003279 A1* | 1/2011 | Patel | G01D 3/10 435/5 |
| 2012/0081696 A1* | 4/2012 | Boersma | G01D 5/268 356/73.1 |
| 2012/0282142 A1 | 11/2012 | Fleischer et al. | |
| 2013/0023714 A1* | 1/2013 | Johnston | A61K 9/0009 600/1 |
| 2013/0274087 A1 | 10/2013 | Da Silva Pinto et al. | |
| 2014/0205846 A1 | 7/2014 | McFarland et al. | |
| 2016/0022976 A1* | 1/2016 | Peyman | A61K 9/5169 600/439 |
| 2016/0085003 A1* | 3/2016 | Jaiswal | G02B 5/208 850/33 |
| 2016/0320300 A1* | 11/2016 | Kasemo | G01N 21/554 |
| 2016/0343887 A1* | 11/2016 | Hossain | H01L 31/02366 |

OTHER PUBLICATIONS

Hendon et al., "Conductive metal-organic frameworks and networks: fact or fantasy?" *Phys. Chem. Chem. Phys.*, vol. 14, pp. 13120-13132, Aug. 3, 2012.

Hu et al., "Surfactant-Directed Atomic to Mesoscale Alignment: Metal Nanocrystals Encased Individually in Single-Crystalline Porous Nanostructures," *Journal of the American Chemical Society*, 136(30): 10561-10564, Jul. 9, 2014.

Huang et al., "A Novel Design of Grooved Fibers for Fiber-Optic Localized Plasmon Resonance Biosensors," *Sensors*, 2009, 9, 6456-6470, Aug. 20, 2009.

Kreno et al., "Metal-organic framework thin film for enhanced localized surface plasmon resonance gas sensing," *Analytical chemistry* 82(19), 2010: 8042-8046, Sep. 14, 2010.

Kreno et al., "Metal-Organic Framework Materials as Chemical Sensors," Chem. Rev. 2012, 112, 1105-1125, Nov. 9, 2011.

Lu et al., "Electrochemical Synthesis of a Microporous Conductive Polymer Based on a Metal-Organic Framework Thin Film," *Angewandte Communications International Edition: Conductive Polymers*, 126(25): 6572-6576, May 22, 2014.

Shekhah et al., "Step-by-Step Route for the Synthesis of Metal-Organic Frameworks," *J. Am. Chem. Soc.* 2007, 129, 15118-15119, Nov. 17, 2007.

Shekhah, Osama. "Layer-by-Layer Method for the Synthesis and Growth of Surface Mounted Metal-Organic Frameworks (SURMOFs)," *Materials*, 2010, 3, 1302-1315, Feb. 23, 2010.

Szilagyi et al., "Metal-organic framework thin films for protective coating of Pd-based optical hydrogen sensors," *J. Mater. Chem. C*, 2013, 1, 9146-8155, Oct. 17, 2013.

Tabassum and Gupta "Surface plasmon resonance-based fiber-optic hydrogen gas sensor utilizing palladium supported zinc oxide multilayers and their nanocomposite," *Applied Optics*, vol. 54, Issue 5, pp. 1032-1040, Feb. 4, 2015.

Talin et al., "Tunable Electrical Conductivity in Metal-Organic Framework Thin-Film Devices," *Science*, 343(6166): 66-69, Jan. 3, 2014.

* cited by examiner

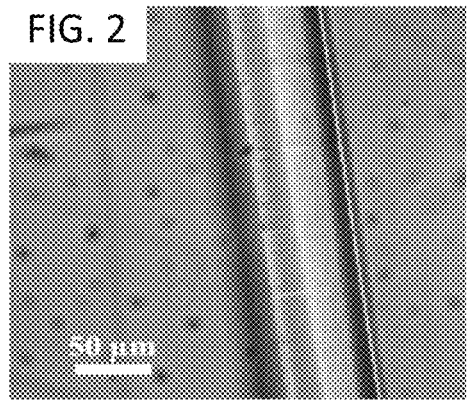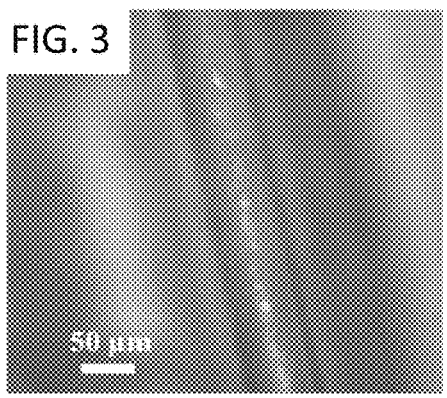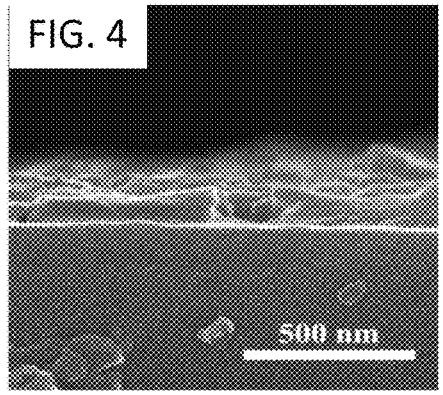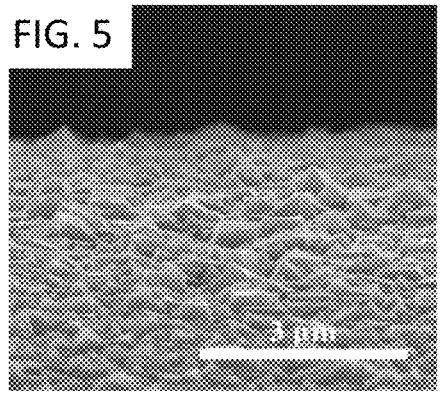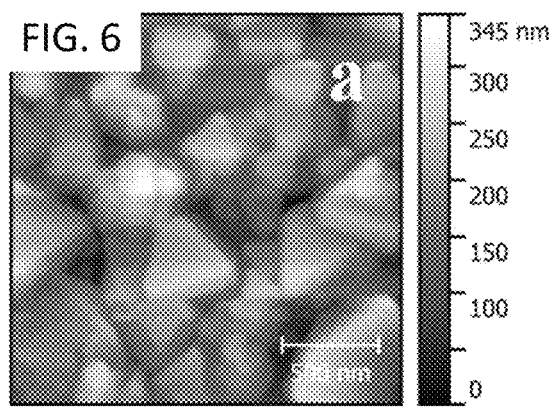

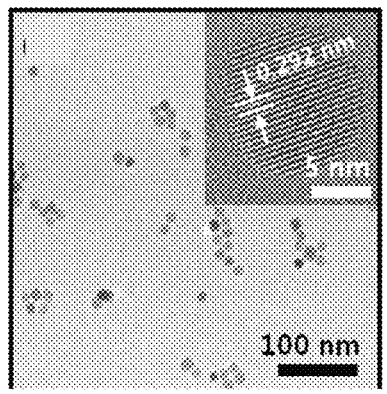 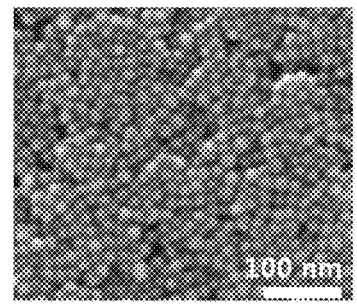
FIG. 30                              FIG. 31
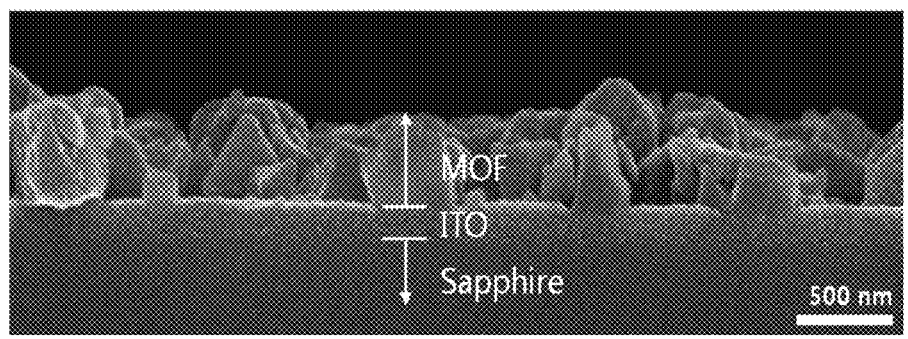
FIG. 32
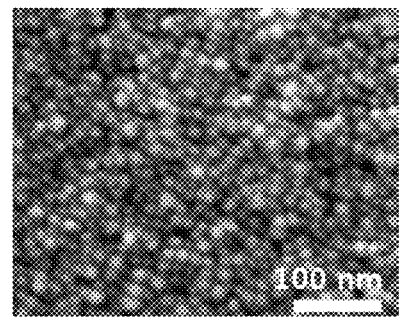
FIG. 33

SENSOR DEVICES COMPRISING A METAL-ORGANIC FRAMEWORK MATERIAL AND METHODS OF MAKING AND USING THE SAME

CROSS REFERENCE TO RELATED APPLICATION

This application claims the benefit of U.S. Provisional Patent Application No. 62/113,967, filed on Feb. 9, 2015, which is incorporated herein by reference in its entirety.

ACKNOWLEDGMENT OF GOVERNMENT SUPPORT

This invention was made with government support under Contract No. DE-FE0004000 awarded by the Department of Energy. The government has certain rights in the invention.

FIELD

The present disclosure concerns sensor devices, compositions used in such devices, and methods of making and using the same.

BACKGROUND

Metal-organic frameworks (or MOFs), which are hybrid materials composed from organic linkers and metal ions, demonstrate excellent properties for gas purification, separation, and storage. In addition, nanoporous MOF thin films are particularly useful in chemical sensing due to their tunability and structural diversity. Despite the high potential of sensors using MOFs, the lack of a highly sensitive and specific signal transduction method has limited their implementation industrially.

Infrared absorption sensors play pivotal roles in analytical chemistry, allowing the quantitative detection of small amounts of molecules and the identification of molecular structures and conformational states. Instrumentation used to detect IR absorption, however, is expensive and not easily transported. While there have been instances of using fiber-optic sensors for chemical sensing, these systems have failed to exhibit utility in particular sensing applications, such as gas sensing, due to low molecule density or high selectivity to a particular gas species of interest within complex gas mixtures. Additionally, most gases do not have fundamental vibration bands at NIR regions; therefore, there has been little success in adopting near-infrared (NIR) optical fibers and optoelectronic devices to detect gases.

SUMMARY

Disclosed herein are embodiments of a sensor device, comprising a substrate coupled to a sensing component, wherein the substrate delivers light from a light source to the sensing component comprising a metal-organic framework material, a plasmonic nanomaterial, or a combination thereof, wherein the metal-organic framework material comprises a first metal and an organic ligand, and the plasmonic nanomaterial comprises a second metal, a metal alloy, a metal oxide, a metal sulfide, a dopant, and combinations thereof; and wherein the plasmonic nanomaterial is not or is other than a spherical or ellipsoidal gold nanoparticle.

In some embodiments, the substrate is a light guide, such as a multi-mode optical fiber or a single-mode optical fiber. In some embodiments, the sensing component is coupled to the entire substrate or a portion of the substrate. In some embodiments, the portion of the substrate comprises a surface area ranging from 0.01% to 10% of the substrate. In an exemplary embodiment, the portion of the substrate comprises a distance of 5 cm to 15 cm.

In some embodiments, the substrate can be coupled to a plurality of sensing components. In some embodiments, the device can comprise a plurality of substrates each coupled to an individual sensing component. The substrate can be coupled to a sensing component comprising a combination of the metal-organic framework material and the plasmonic nanomaterial. In such embodiments, the plasmonic nanomaterial can be embedded within internal pores of the metal-organic framework material. In other such embodiments, the plasmonic nanomaterial can be encapsulated within one or more layers of the metal-organic framework material. In some embodiments, the substrate can be physically coupled to the sensing component or chemically coupled to the sensing component. Some embodiments concern using a thin layer of the sensing component coupled to the substrate. This thin layer can have a thickness ranging from 1 nm to 500 nm. In other embodiments, a thick layer of the sensing component can be coupled to the substrate. In some embodiments, the thick layer can have a thickness ranging from 500 nm to 50 μm.

In particular disclosed embodiments, the sensor devices disclosed herein can detect gases at concentrations ranging from 100 ppm to 500 ppm. Some embodiments exhibit a response time of 0.1 seconds to 100 seconds.

In some embodiments, the sensor device can be comprised of a substrate that delivers near infrared light from a light source to a sensing component comprising a metal-organic framework material, wherein the sensing component is coupled to the substrate. In exemplary embodiments, the substrate can be a light guide. Suitable detectable species can be selected from gases, volatile organic molecules, or combinations thereof. The metal-organic framework material can comprise a metal and an organic ligand. The metal can be selected from copper, silver, gold, aluminum, zinc, cobalt, nickel, magnesium, manganese, iron, or combinations thereof. The organic ligand can be selected from oxalic acid, malonic acid, succinic acid, glutaric acid, phthalic acid, terephthalic acid, citric acid, trimesic acid, benzene-1,3,5-tricarboxylic acid (BTC), 4,6-dioxido-1,3-benzenedicarboxylate (DOBDC), 1,2,3-triazole, pyrrodizaole, squaric acid, or combinations thereof. In exemplary embodiments, the metal-organic framework is Cu-BTC.

Also disclosed herein are sensor devices comprising a substrate that delivers near infrared light from a light source to a combined sensing component comprising a metal-organic framework material and a plasmonic nanomaterial, wherein the sensing component is coupled to the substrate. In such embodiments, the plasmonic nanomaterial can comprise a metal oxide, one or more dopants, a nanowire or nanorod array, or combinations thereof. In some embodiments, the metal oxide is doped with a dopant. In some exemplary embodiments, the metal oxide is $TiO_2$ and the dopant is Sn. Exemplary nanorod arrays can comprise a gold nanorod array or a gold antenna array.

Also disclosed herein are embodiments of a method of determining the presence of a detectable species, comprising exposing a sample to a sensor device embodiment or sensor device network embodiment disclosed herein and analyzing the sample for a near-infrared signal produced by a detectable species absorbed by the sensing component of the sensor device of claim 1 or the sensor device network of claim 25. In some embodiments, the sample can be an environmental sample selected from a gas sample or an air sample.

The foregoing and other objects, features, and advantages of the present disclosure will become more apparent from the following detailed description, which proceeds with reference to the accompanying figures.

BRIEF DESCRIPTION OF THE DRAWINGS

FIG. 2 is an optical image of the core of an optical fiber before coating with a representative MOF material.

FIG. 3 is an optical image of the core of an optical fiber after coating with a representative MOF material.

FIG. 4 is an SEM image of a cross-section of the MOF-coated optical fiber illustrated in FIG. 3.

FIG. 5 is an SEM image of the surface of the MOF-coated optical fiber illustrated in FIG. 3.

FIG. 6 is an AFM image of an optical fiber coated with a representative MOF material.

FIG. 30 is a TEM image of 10% Sn-doped ITO nanocrystals in hexane, with an insert providing a high-resolution TEM image.

FIG. 31 is an SEM image a deposited ITO film onto a sapphire substrate by spin-coating.

FIG. 32 is a cross-sectional view SEM image of a combined sensing component deposited on a substrate using 30 cycles of MOF deposition.

FIG. 33 is an SEM image of a deposited ITO film on sapphire after $O_2$ plasma treatment.

Figure 44:
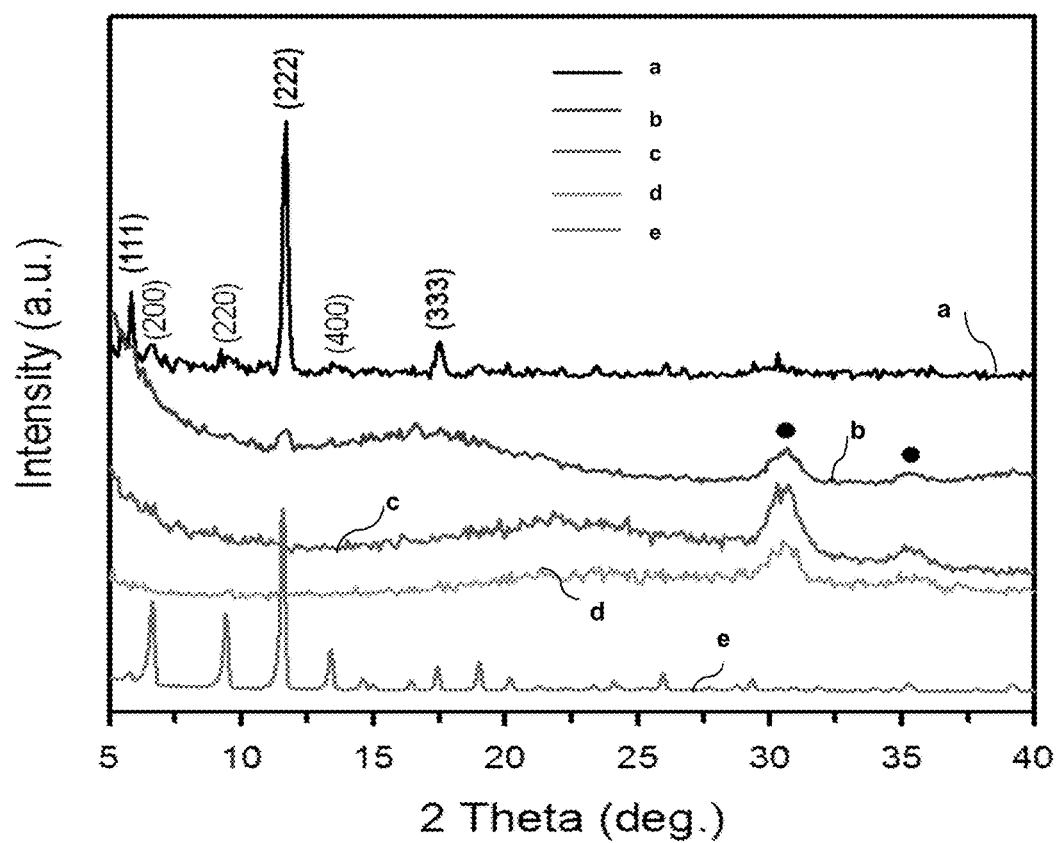

FIG. 44 illustrates XRD patterns of an as-deposited ITO film (orange), an $O_2$ plasma-treated ITO film (green), a combined sensing component after 10 cycles of MOF material growth (purple), a combined sensing component after 30 cycles of MOF material growth (black), and a bulk MOF material prepared by a solvothermal reaction, which is shown for reference (red).

Figure 45:
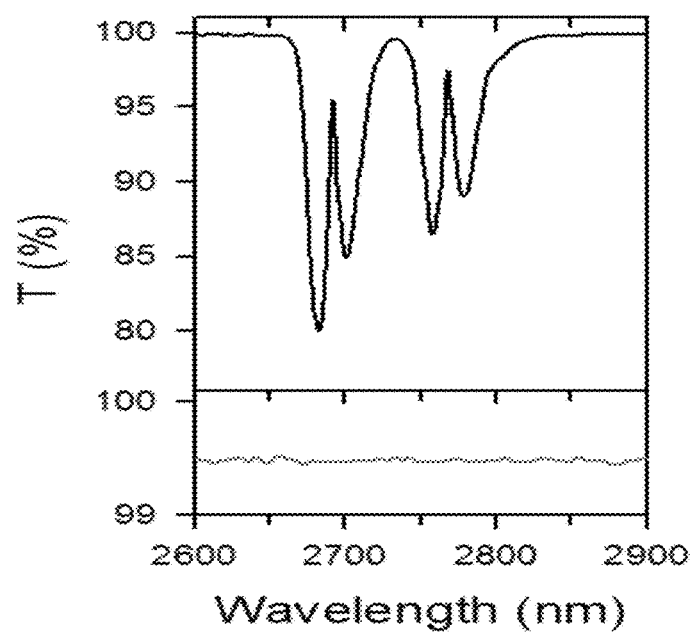

FIG. 45 is a graph of transmittance as a function of wavelength illustrating the difference in % T at high (100%) (top) and low (0.1%) (bottom) concentrations of $CO_2$ flowing on ITO/Sapphire and MOF//ITO/Sapphire samples.

Figure 46:
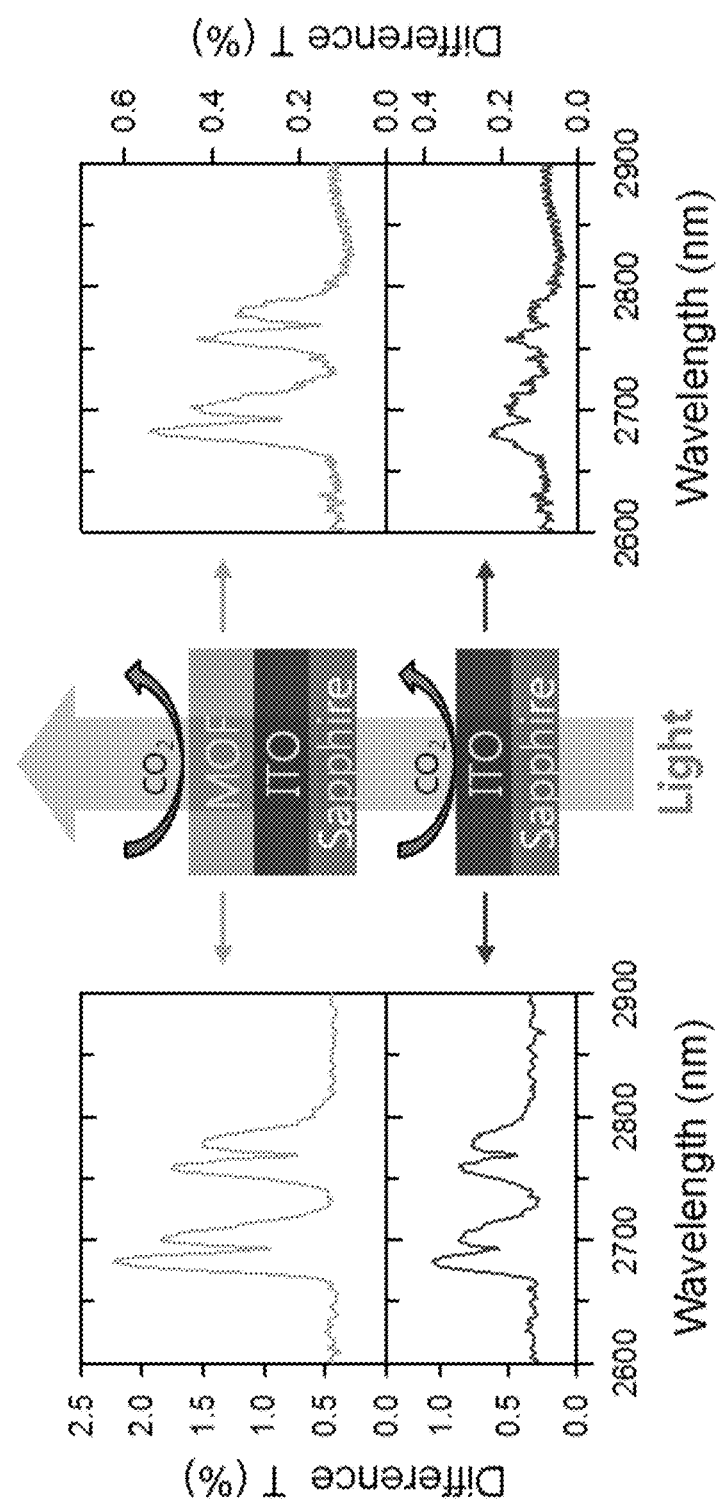

FIG. 46 illustrates a schematic diagram of $CO_2$ flowing on exemplary sensor device samples (middle), the difference in each sample's transmittance (% T) at high concentration of $CO_2$ flowing (left) and low concentration of $CO_2$ flowing (right).

Figure 47A:
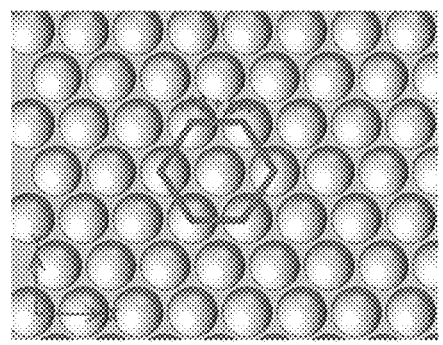
Figure 47B:
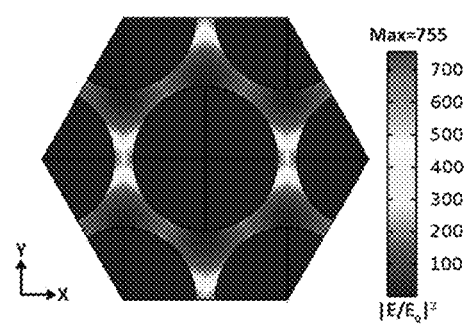
Figure 47C:
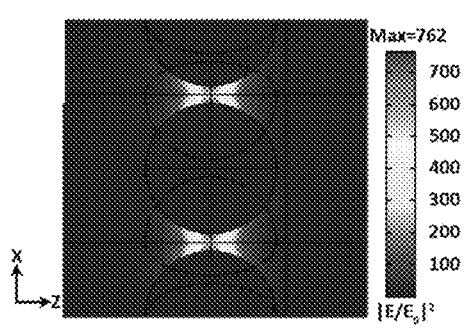

FIGS. 47A-47C illustrate results obtained from a 3D FEM simulation of an ITO nanocrystal array; FIG. 47A is a schematic of the simulation model and electric field intensity distribution on XY (FIG. 47B) and XZ (FIG. 47C) planes at λ=2700 nm.

Figures 48A, 48B:
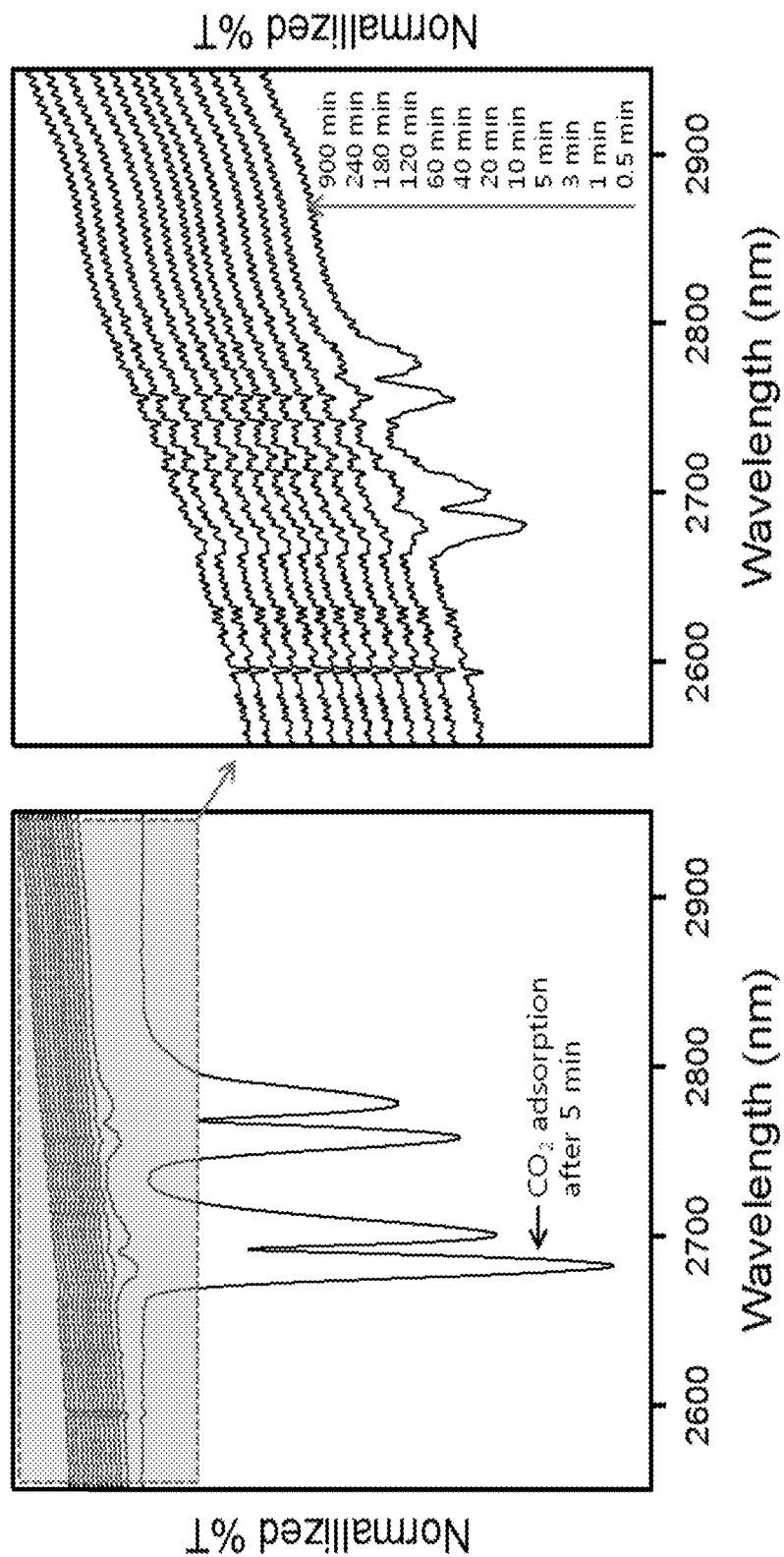

FIGS. 48A and 48B illustrate results obtained from recovery analysis of a flow cell used in an exemplary embodiment; FIG. 48A is an absorption spectrum of $CO_2$ at ~2700 nm, with magnified spectra of the dotted square inset area as a function of elapsed time (FIG. 48B)

Figures 49A, 49B:
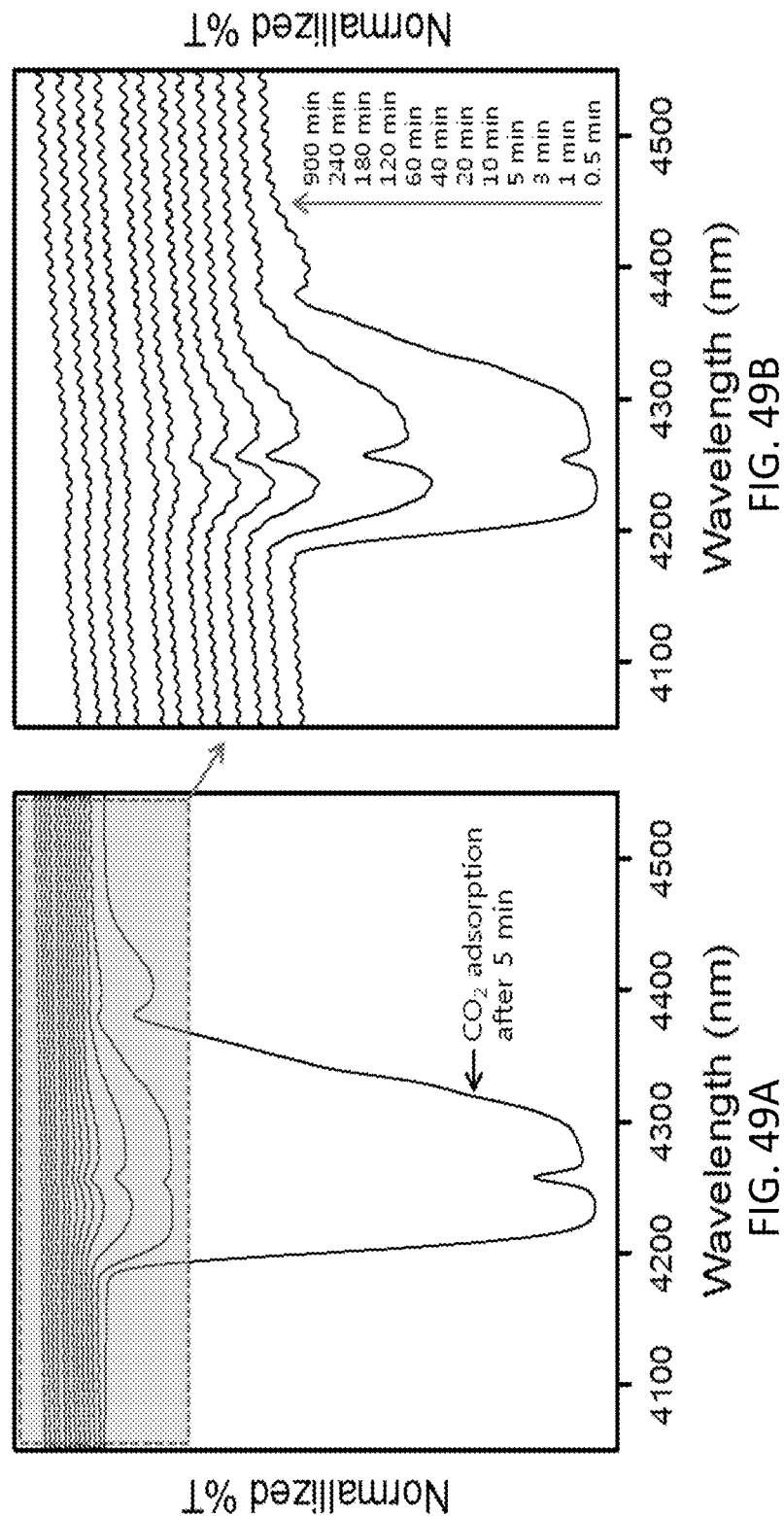

FIGS. 49A and 49B illustrate results obtained from recovery analysis of a flow cell used in an exemplary embodiment; FIG. 49A is an absorption spectrum of $CO_2$ at ~4200 nm, with magnified spectra of the dotted square inset area as a function of elapsed time (FIG. 49B)

Figure 50A:
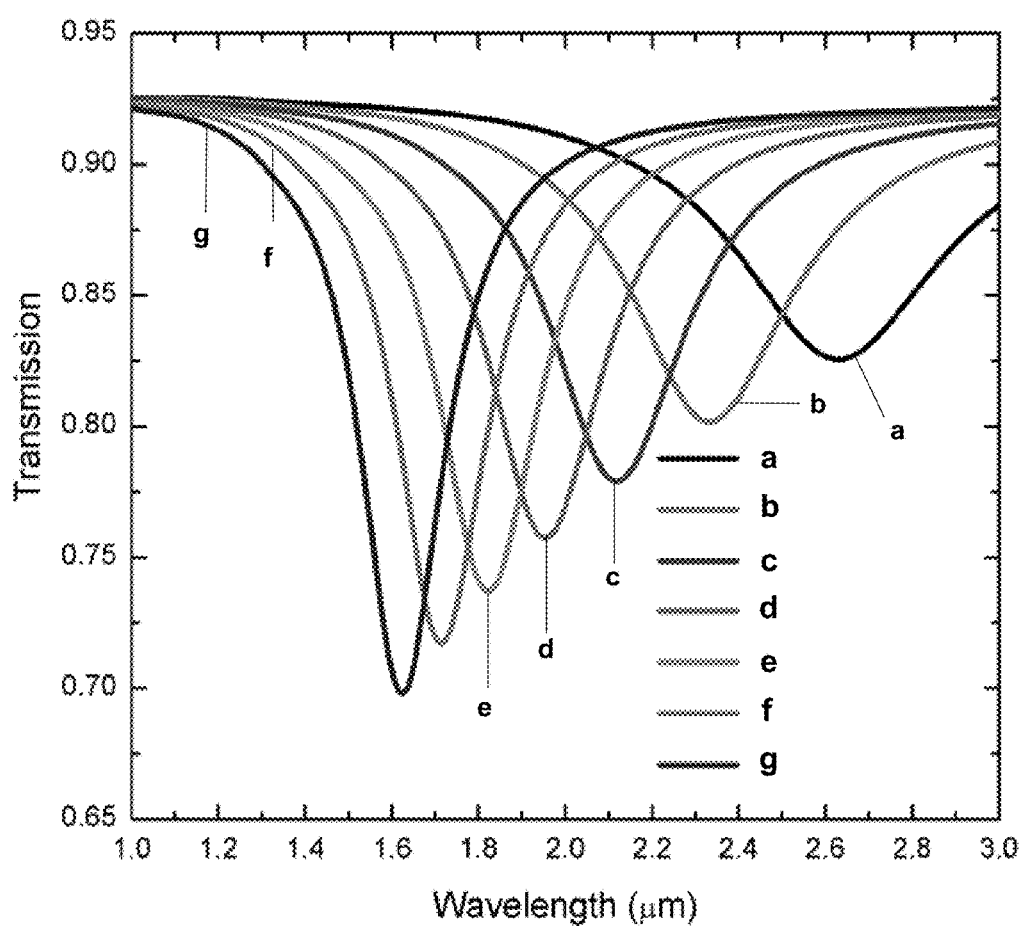
Figure 50B:
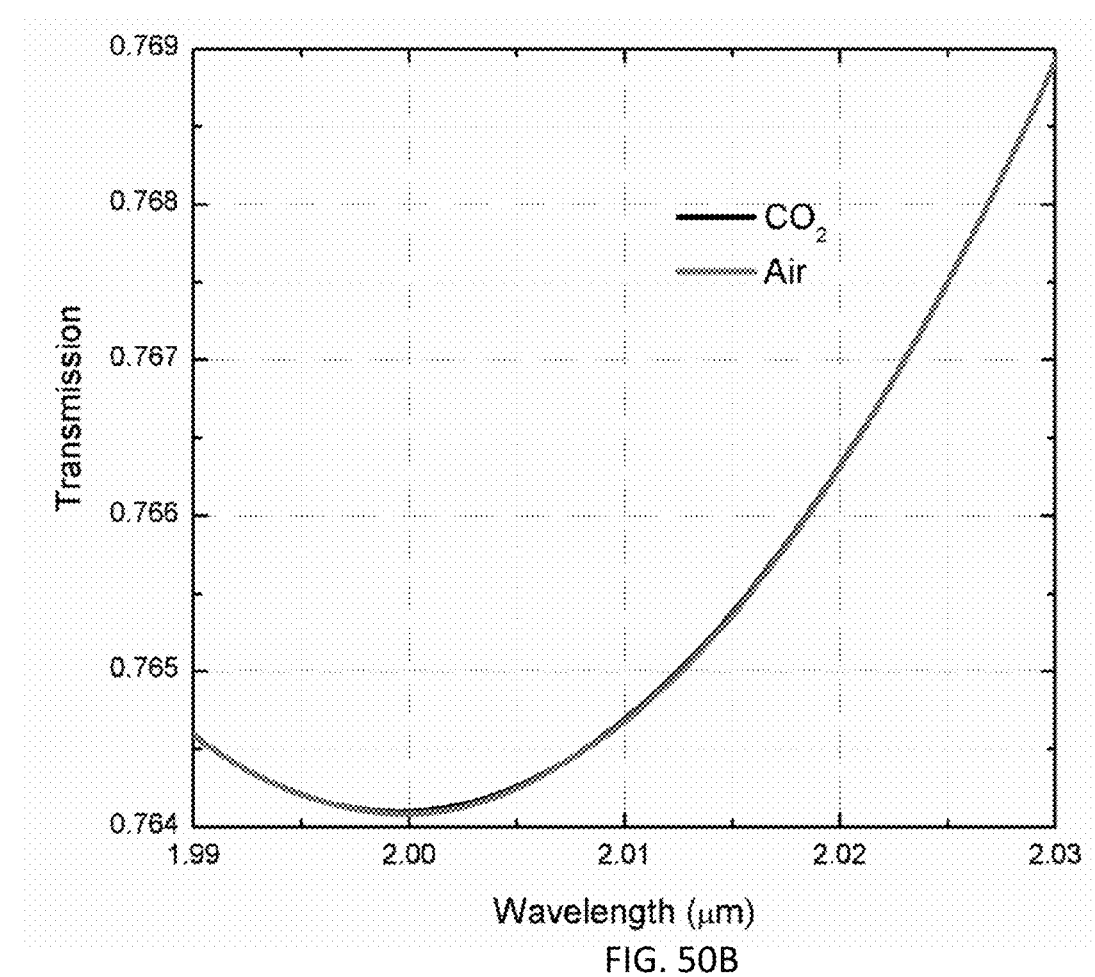
Figure 50C:
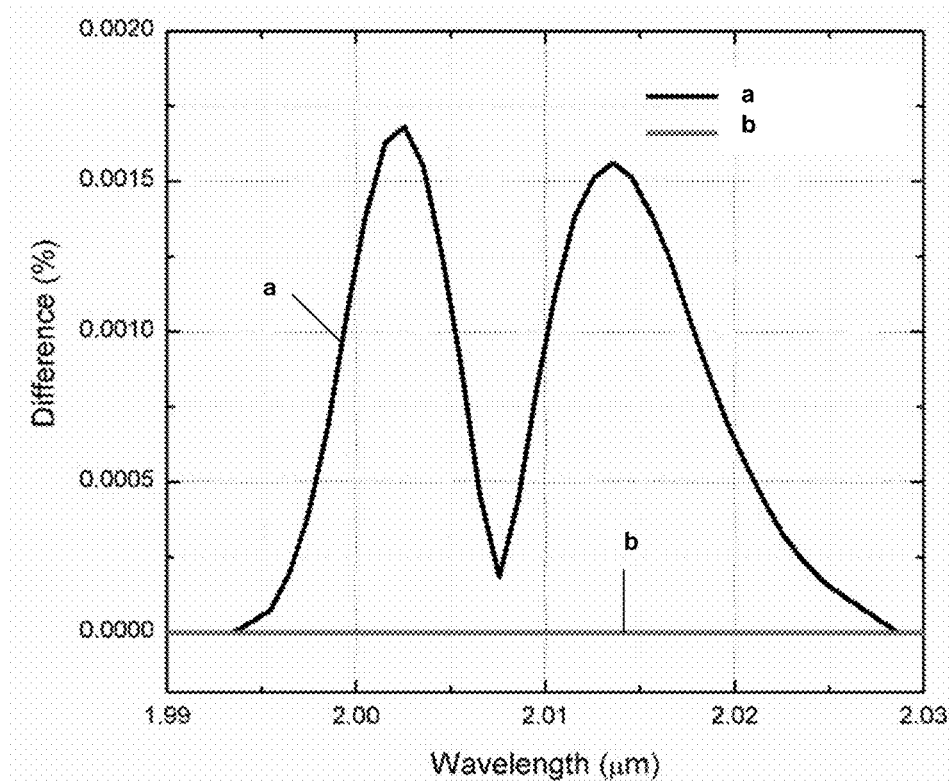
Figure 50D:
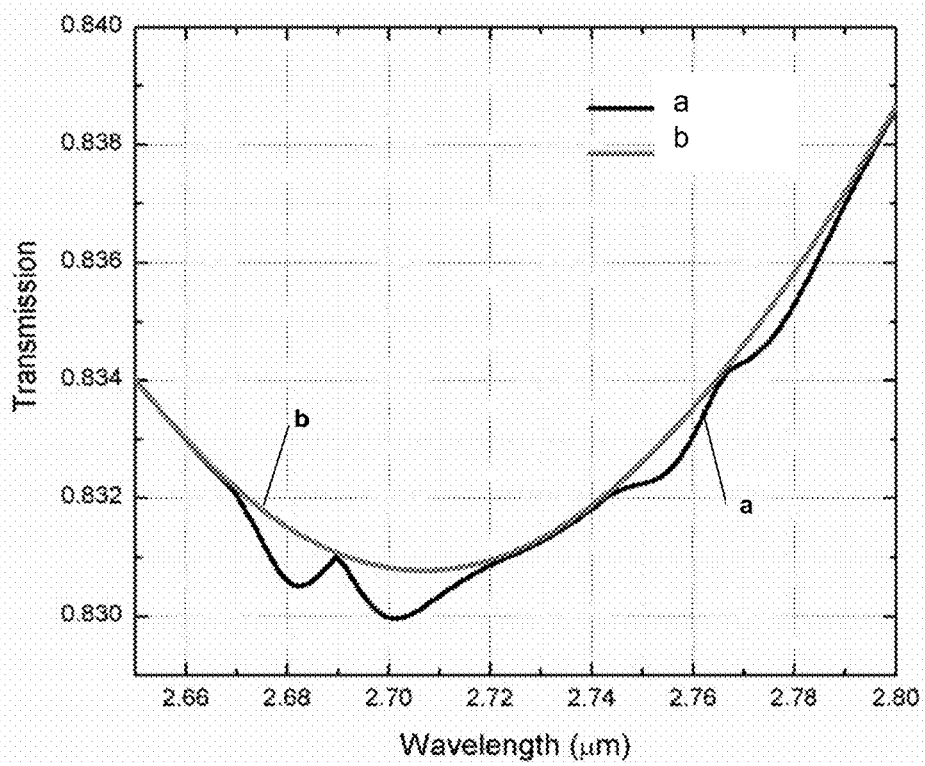
Figure 50E:
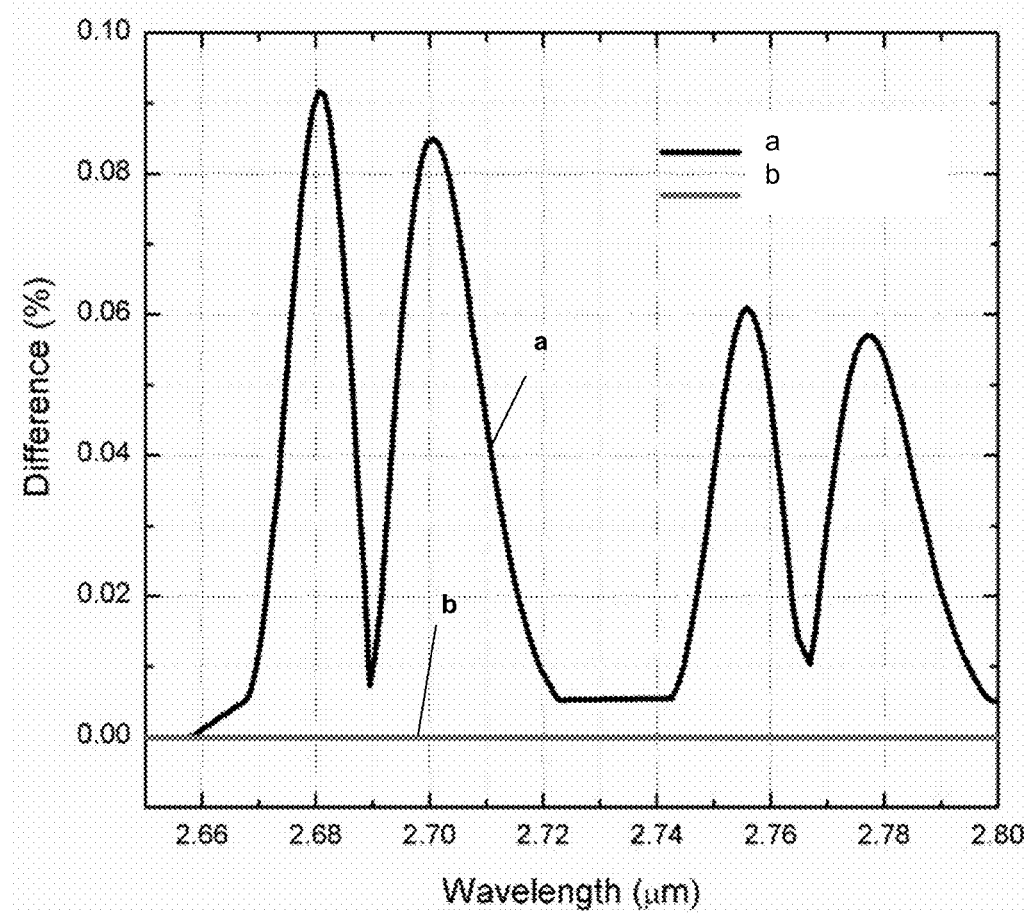
Figure 50F:
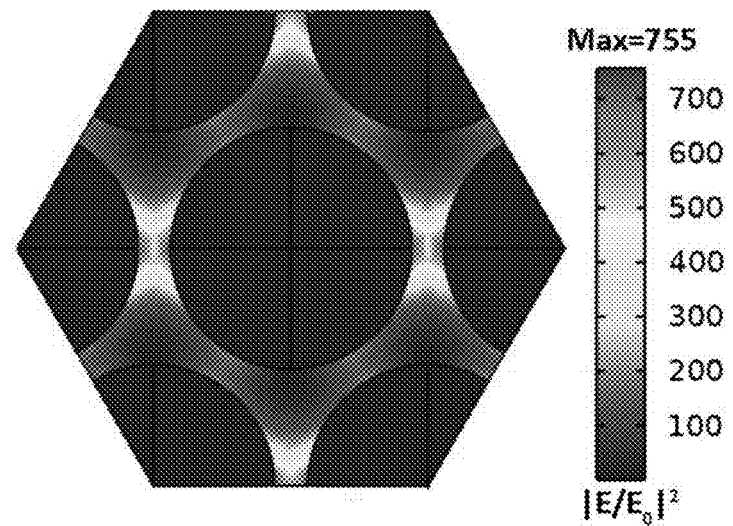

FIGS. 50A-50F illustrate results obtained from analyzing an embodiment of an ITO nanoparticle film; FIG. 50A is a combined transmission spectrum illustrating transmission spectra an ITO nanoparticle thin film with differing carrier concentration; FIG. 50B is a combined transmission spectrum illustrating transmittance through the ITO nanoparticle film with air and $CO_2$ as the ambient gas at 2.0 µm; FIG. 50C is an IR absorption peak illustrating the IR absorption of $CO_2$ at 2.0 µm with (line a) and without the nanoparticle film (line b); FIG. 50D is a combined transmission spectrum illustrating transmittance through the ITO nanoparticle film with air (line b) and $CO_2$ (line a) as the ambient gas at 2.7 µm; FIG. 50E is an IR absorption peak illustrating the IR absorption of $CO_2$ at 2.7 µm with (line a) and without the nanoparticle film (line b); and FIG. 50F illustrates the optical field intensity distribution.

Figure 51A:
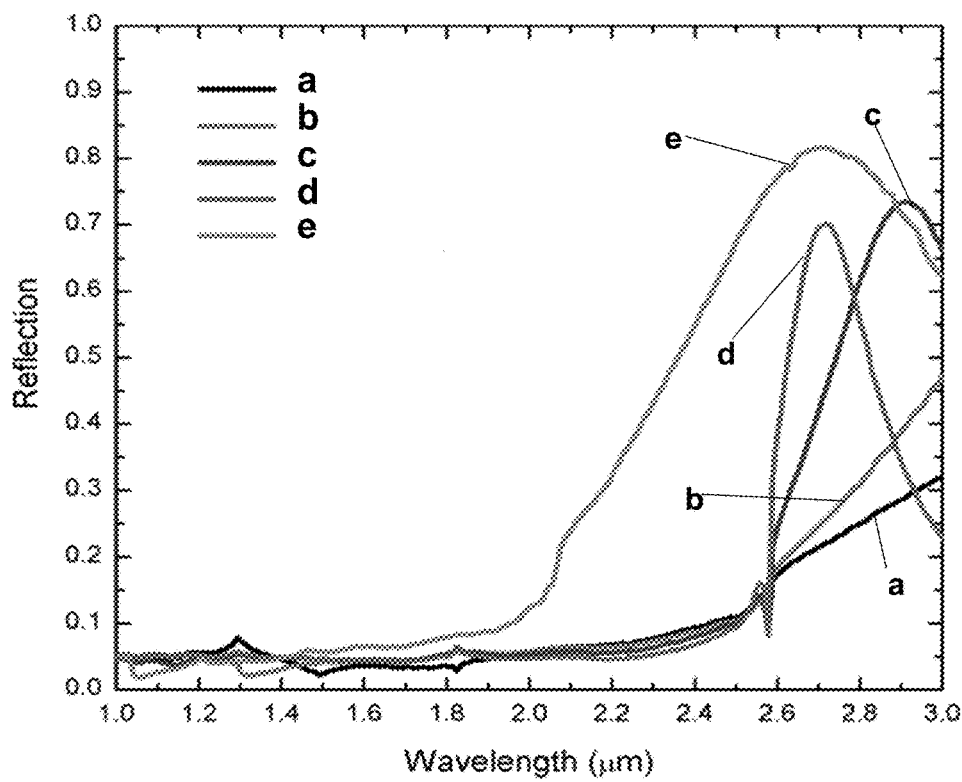
Figure 51B:
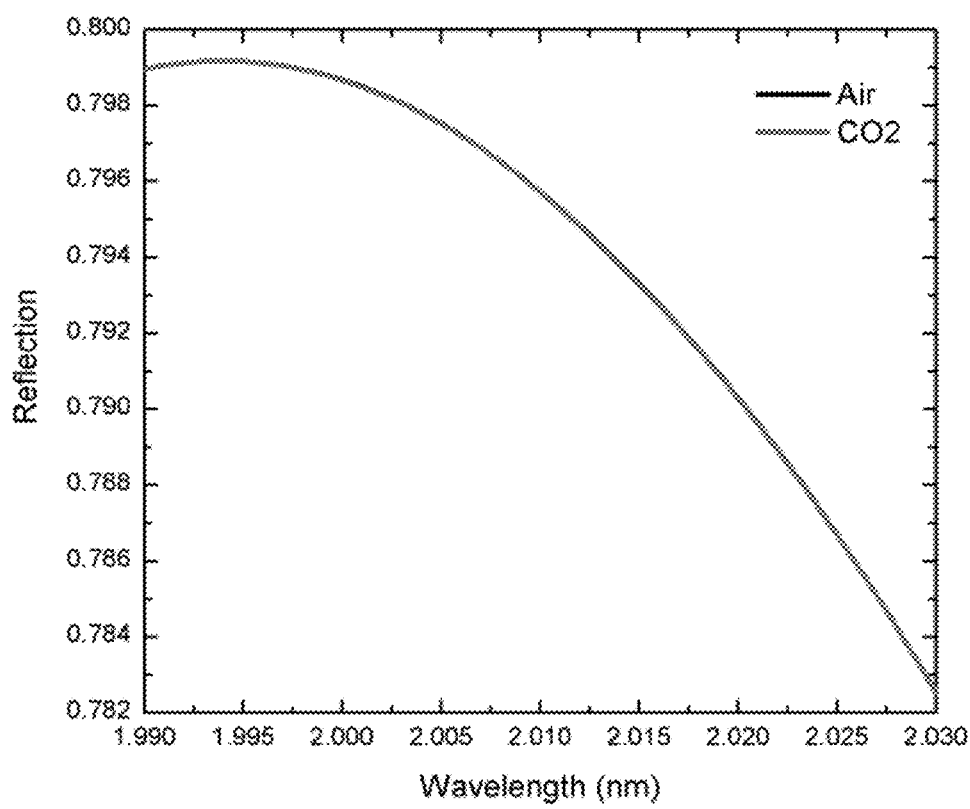
Figure 51C:
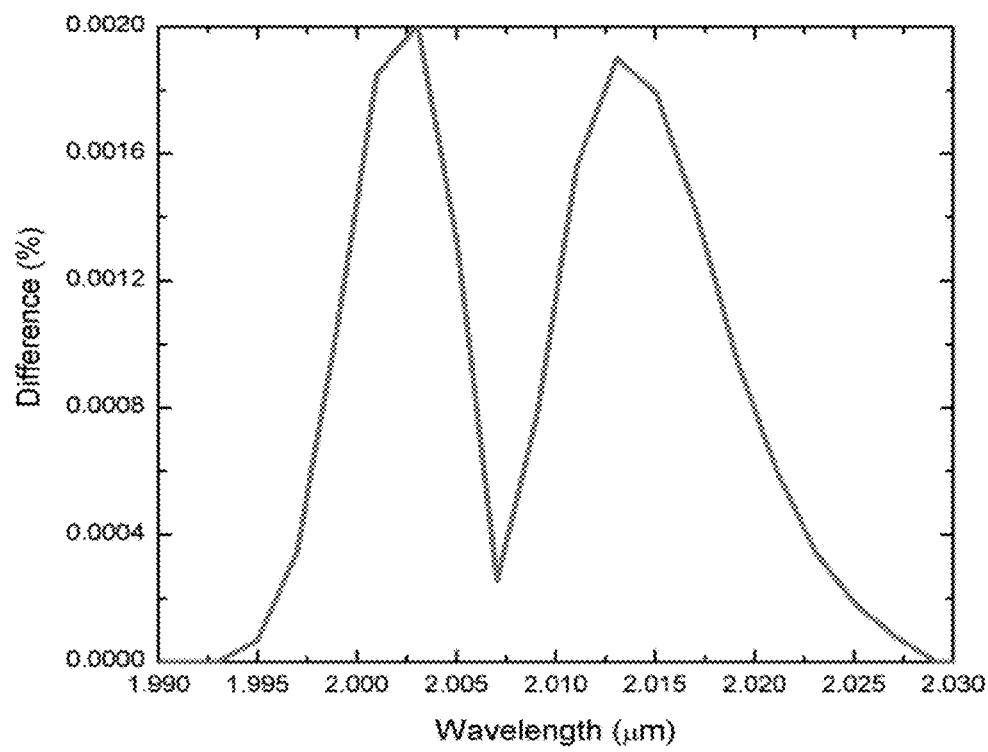
Figure 51D:
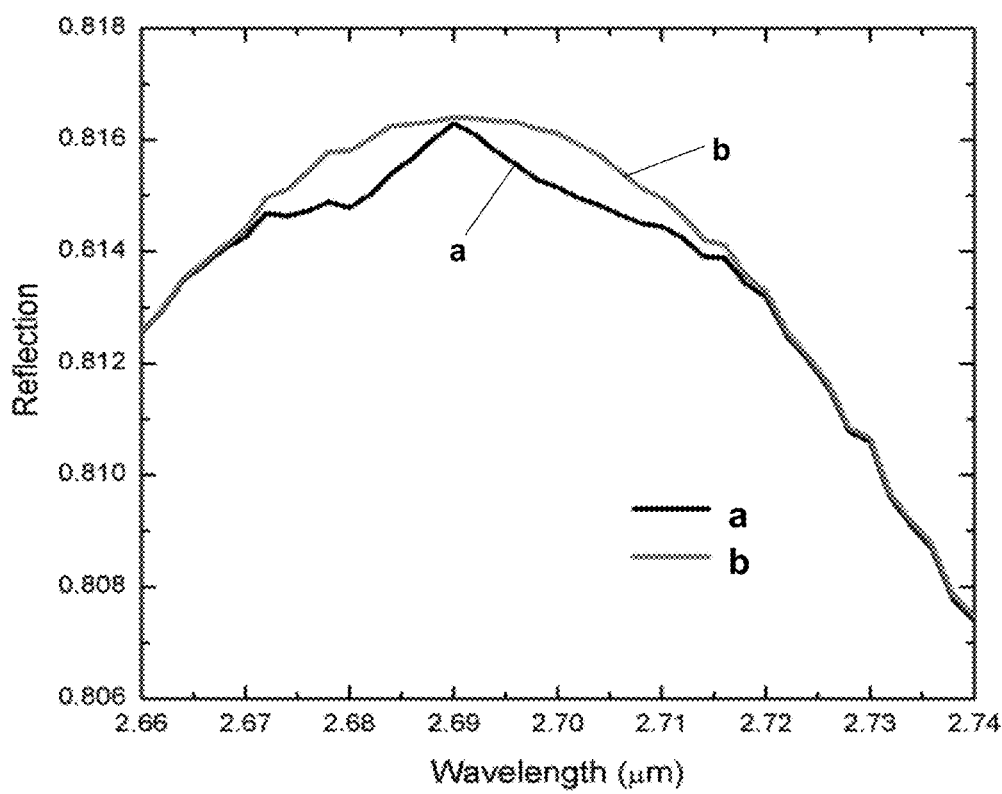
Figure 51E:
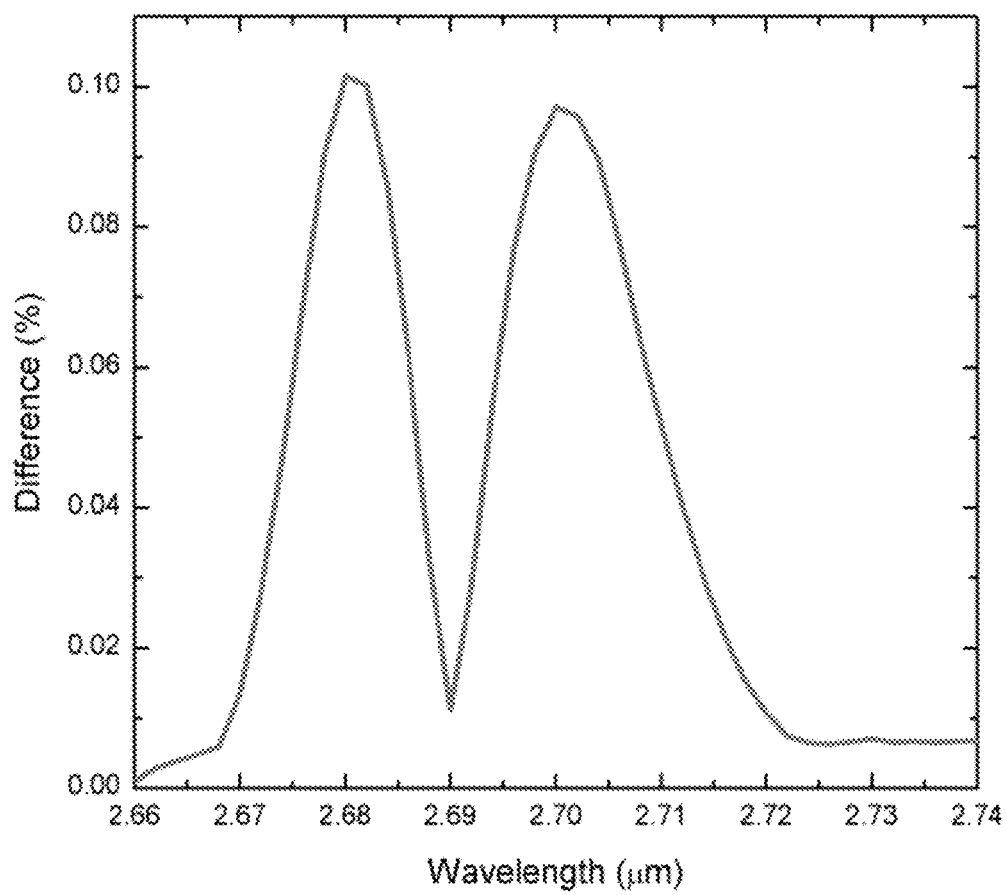
Figure 51F:
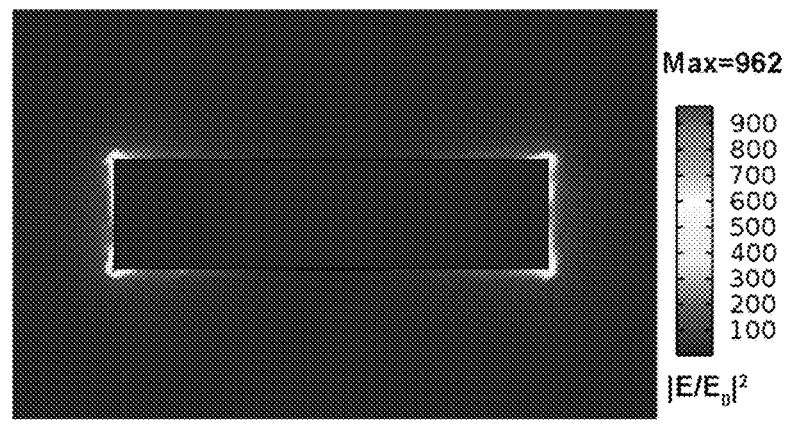

FIGS. 51A-51F illustrate results obtained from analyzing an embodiment of a gold nanorod array; FIG. 51A is a combined reflection spectrum illustrating reflection spectra of different gold nanorod arrays having different sizes and periods; FIG. 51B is a combined reflection spectrum illustrating the reflection spectra obtained for air and $CO_2$ at 2.0 µm; FIG. 51C illustrates the difference of the two spectra in FIG. 51B at 2.0 µm; FIG. 51D is a combined reflection spectrum illustrating the reflection spectra for air (line b) and $CO_2$ (line a) at 2.7 µm; FIG. 51E illustrates the difference of the two spectra in FIG. 51D 2.7 µm; and FIG. 51F illustrates the optical field intensity distribution of a single Au nanorod.

Figure 52A:
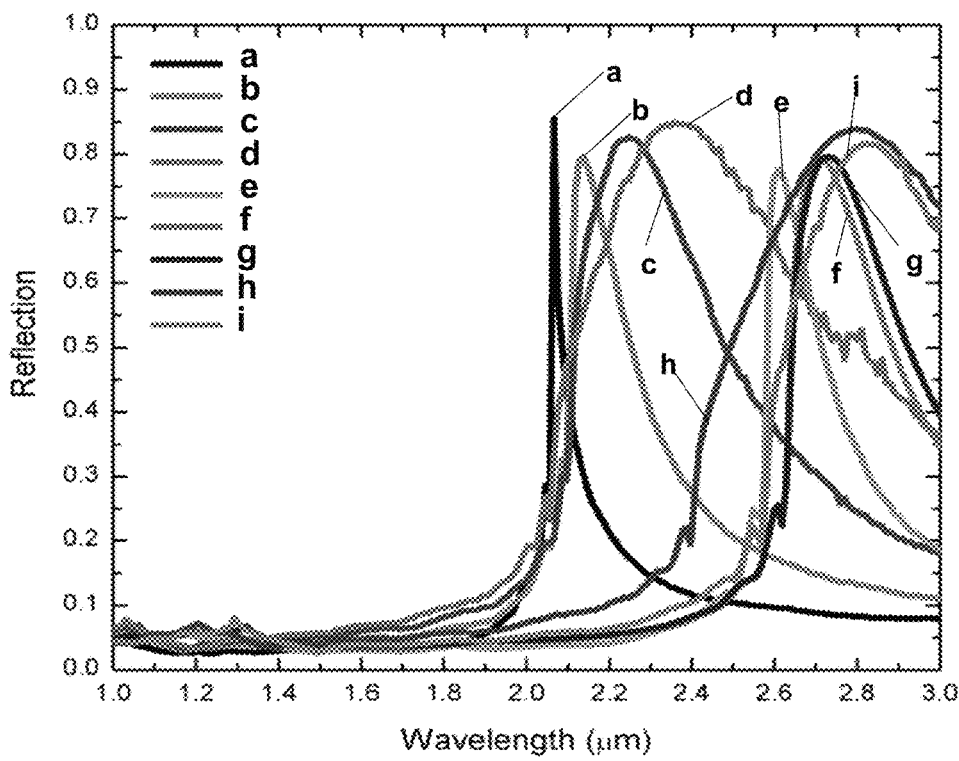
Figure 52B:
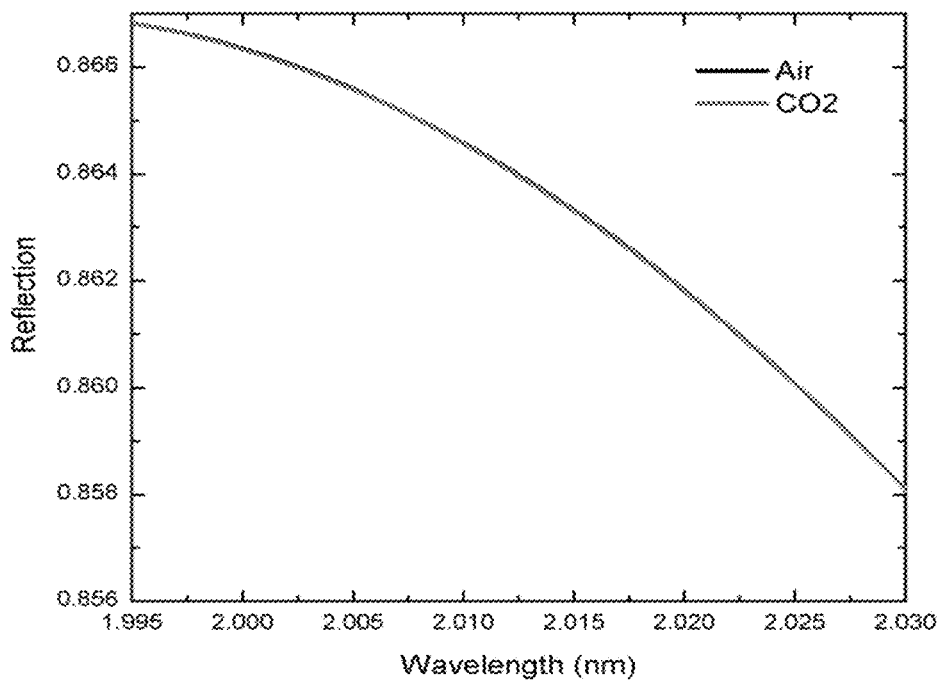
Figure 52C:
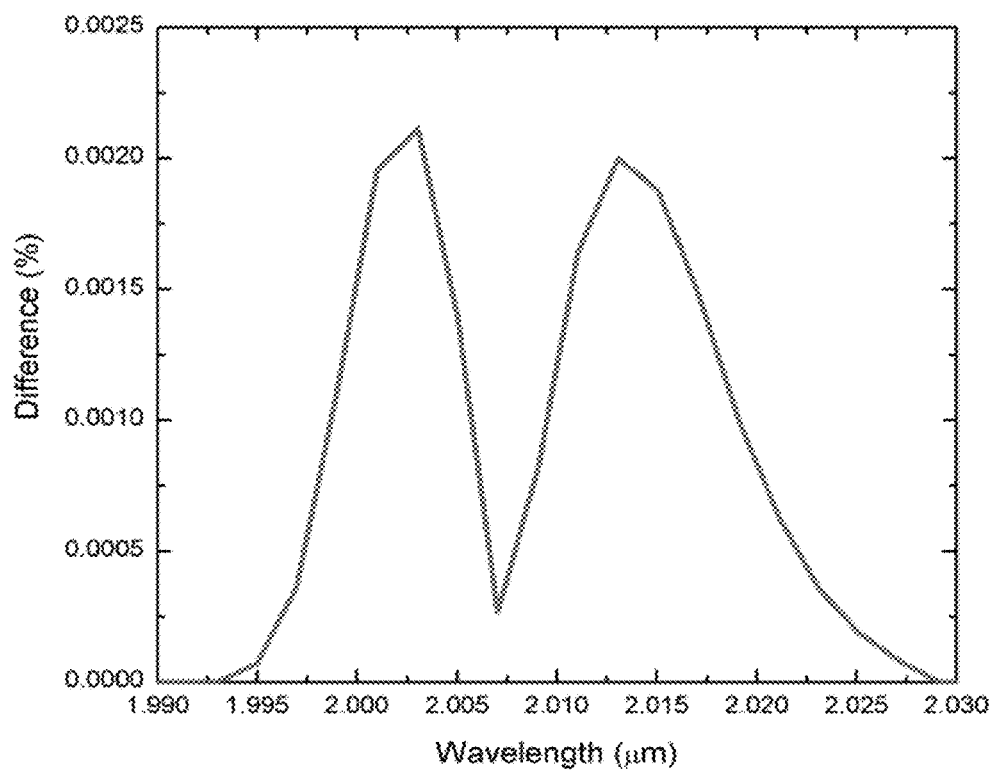
Figure 52D:
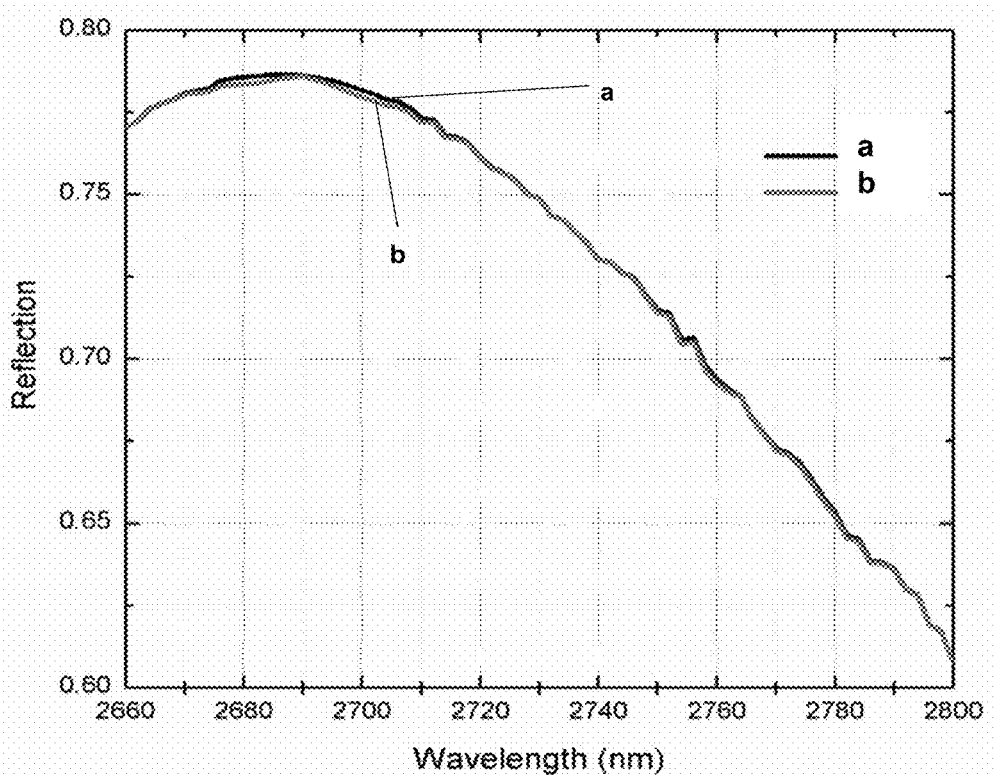
Figure 52E:
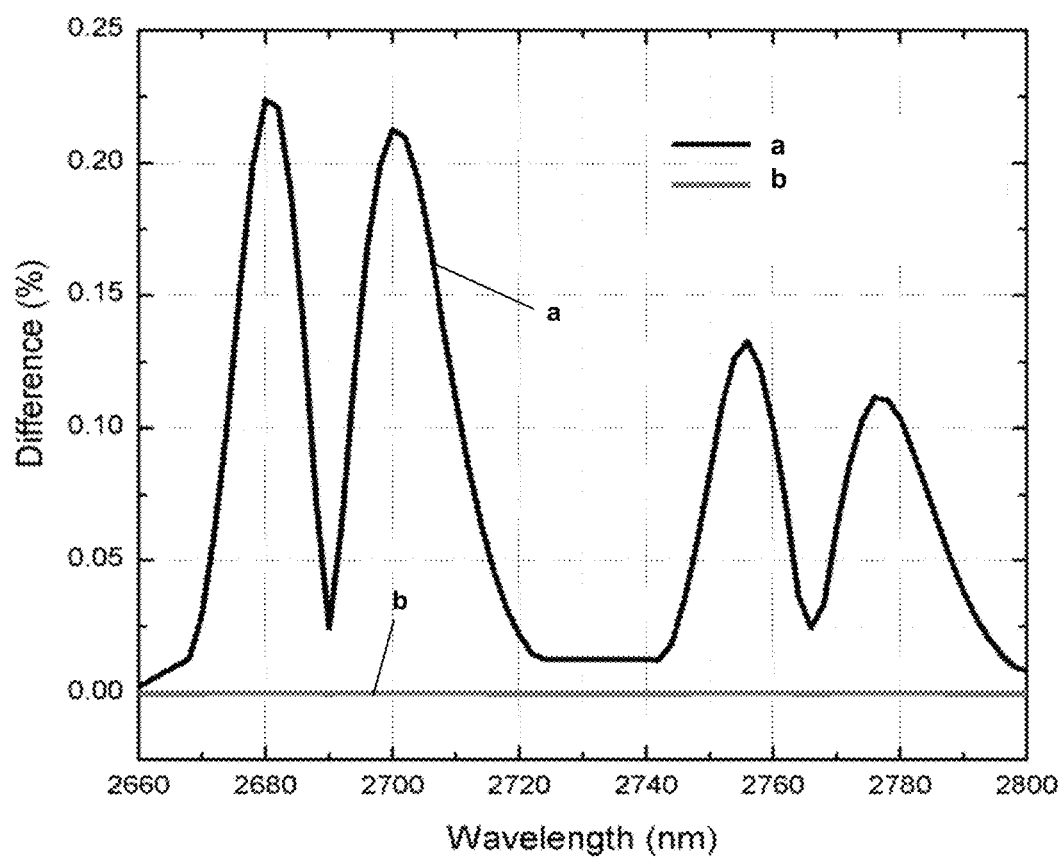
Figure 52F:
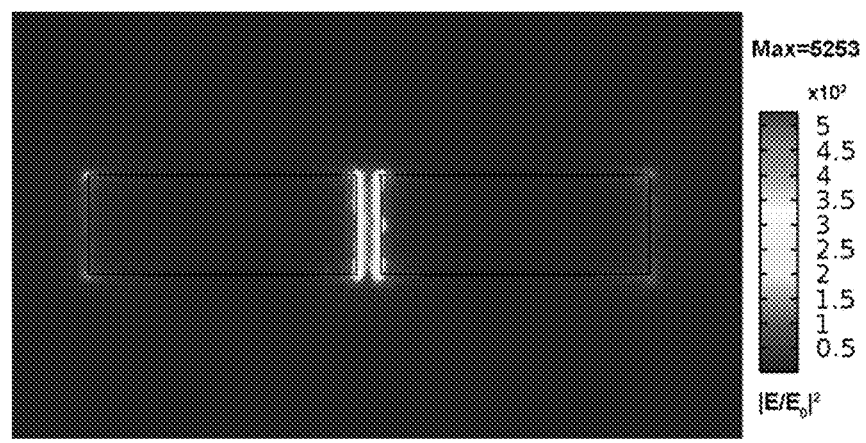

FIGS. 52A-52F illustrate results obtained from analyzing an embodiment of a gold dipole antenna array; FIG. 52A is a combined reflection spectrum illustrating reflection spectra of different gold dipole antenna arrays having different sizes and periods; FIG. 52B is a combined reflection spectrum illustrating the reflection spectra obtained for air and $CO_2$ at 2.0 µm; FIG. 52C illustrates the difference of the two spectra in FIG. 52B at 2.0 µm; FIG. 52D is a combined reflection spectrum illustrating the reflection spectra for air (line a) and $CO_2$ (line b) at 2.7 µm; FIG. 52E illustrates the difference of the two spectra in FIG. 52D 2.7 µm (line a=with pattern; line b=without pattern); and FIG. 52F illustrates the optical field intensity distribution between two Au nanorods.

Figure 53:
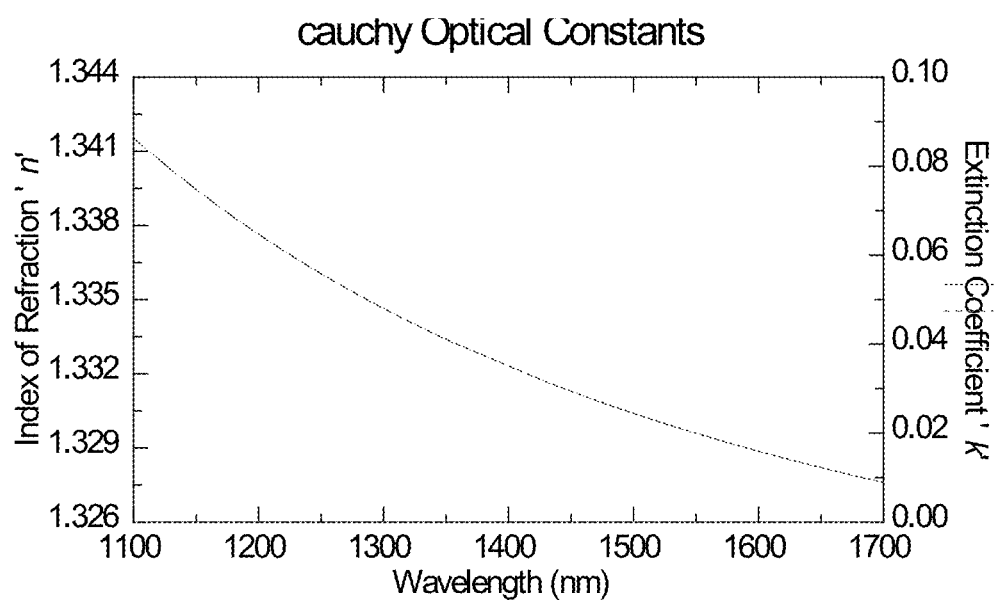

FIG. 53 is a graph illustrating the refractive index of an MOF material measured by an ellipsometer.

Figure 54:
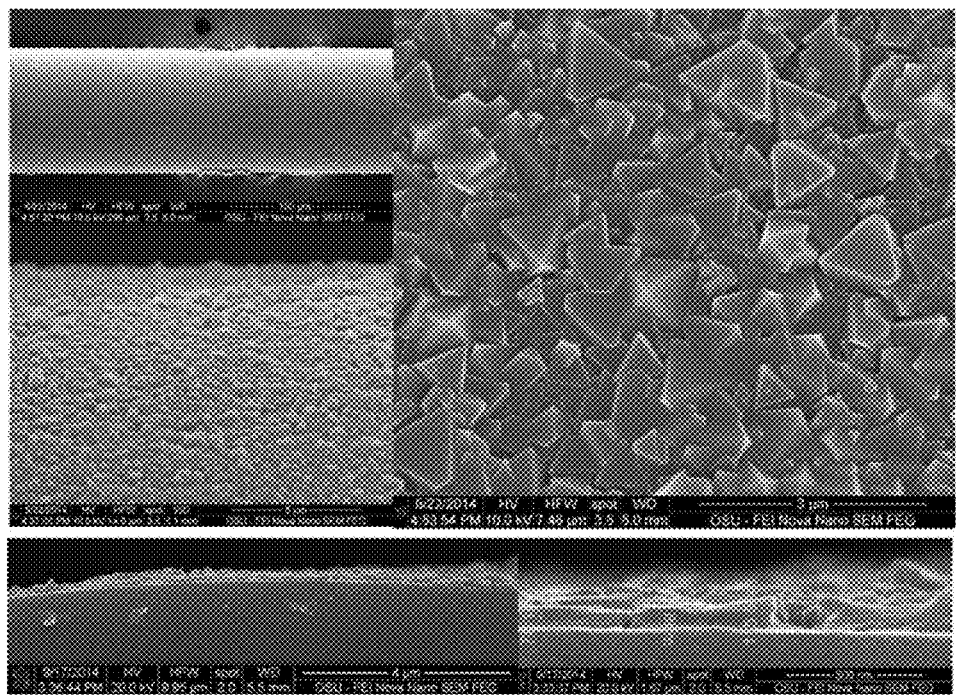

FIG. 54 illustrates combined SEM images of etched optical fiber coated with an MOF material.

Figure 55:
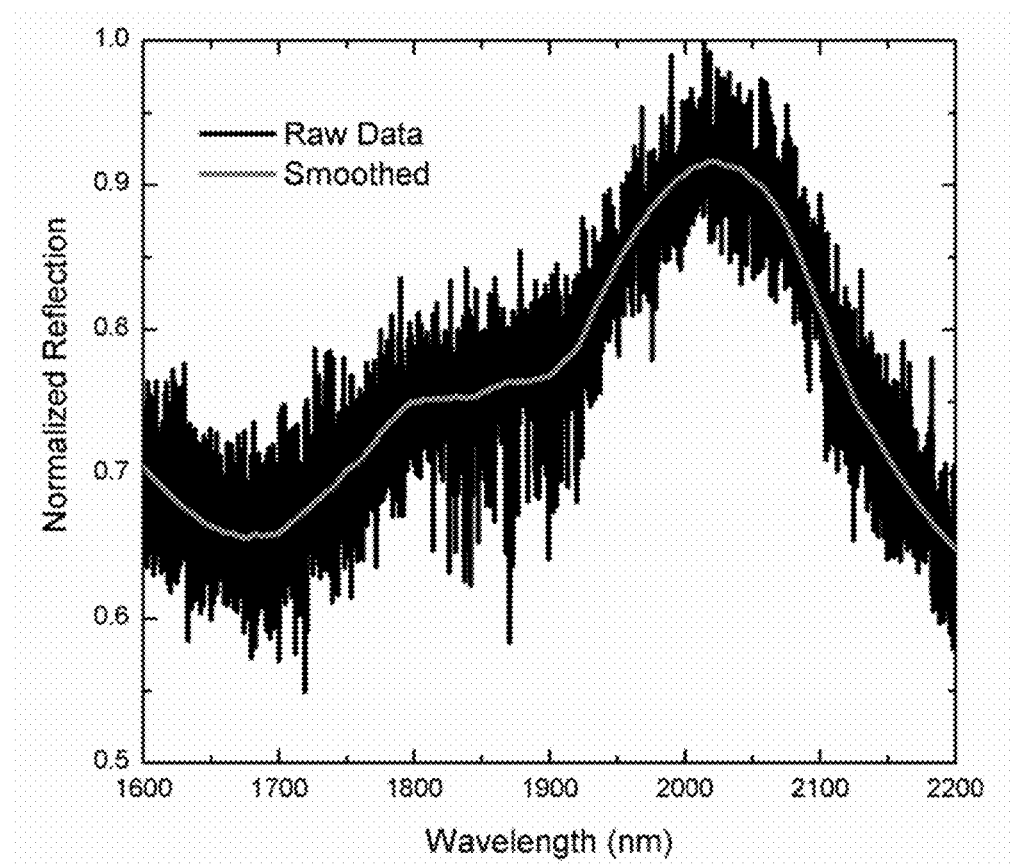

FIG. 55 is a reflection spectrum obtained from an exemplary Au nanorod embodiment.

Figure 56:
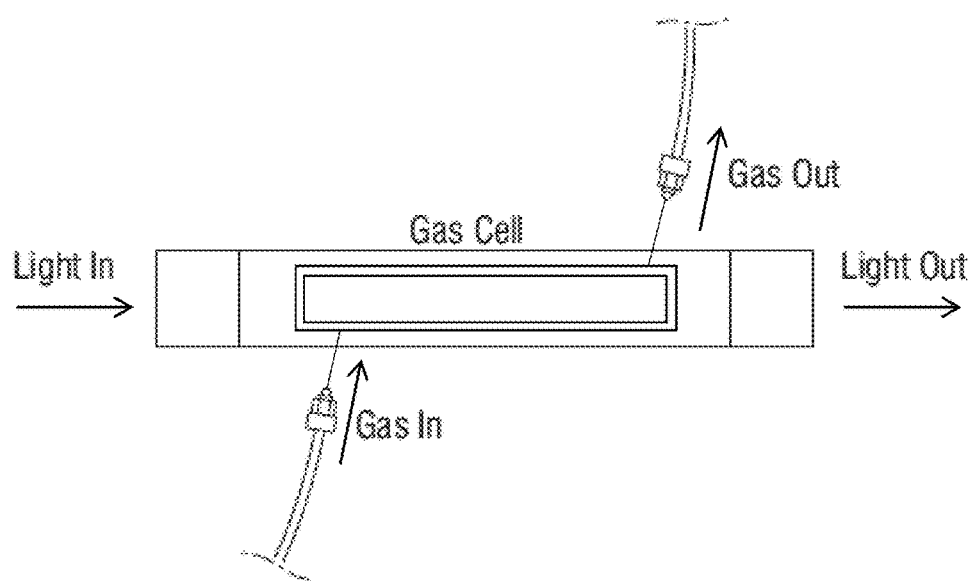

FIG. 56 is a photographic image of a sensor cell.

Figure 57:
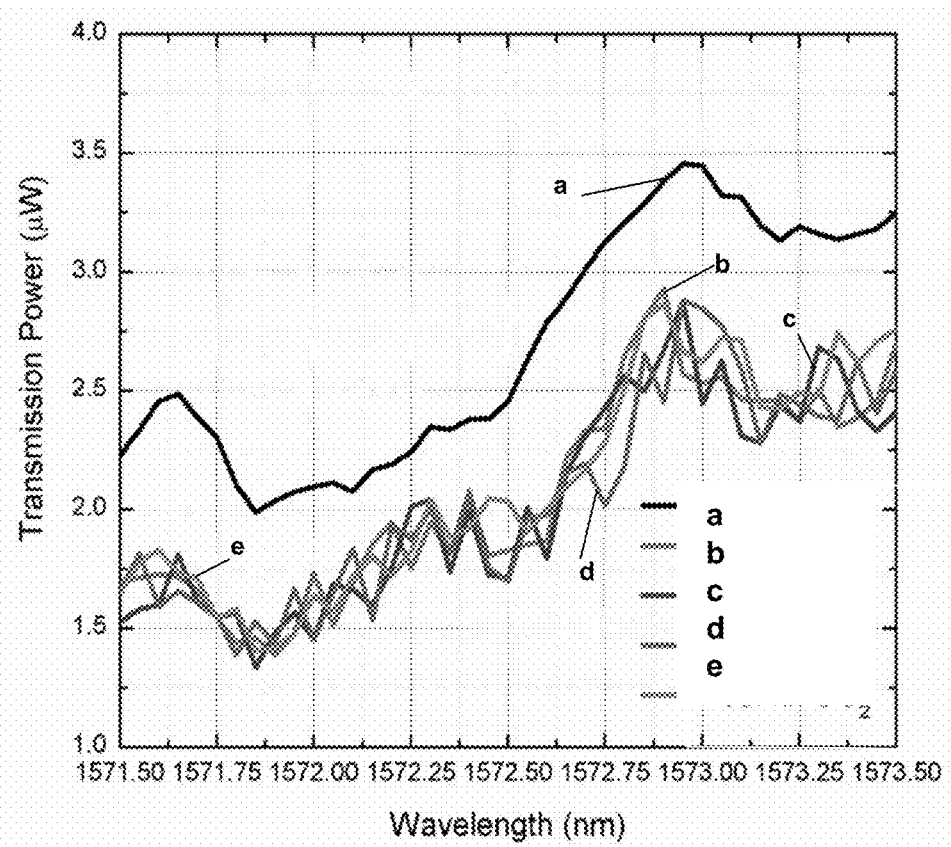

FIG. 57 is a combined transmission spectrum illustrating various transmission spectra obtained from analysis using the sensor cell embodiment illustrated in FIG. 56 at 1571.5 nm and 1573.5 nm.

Figure 58A:
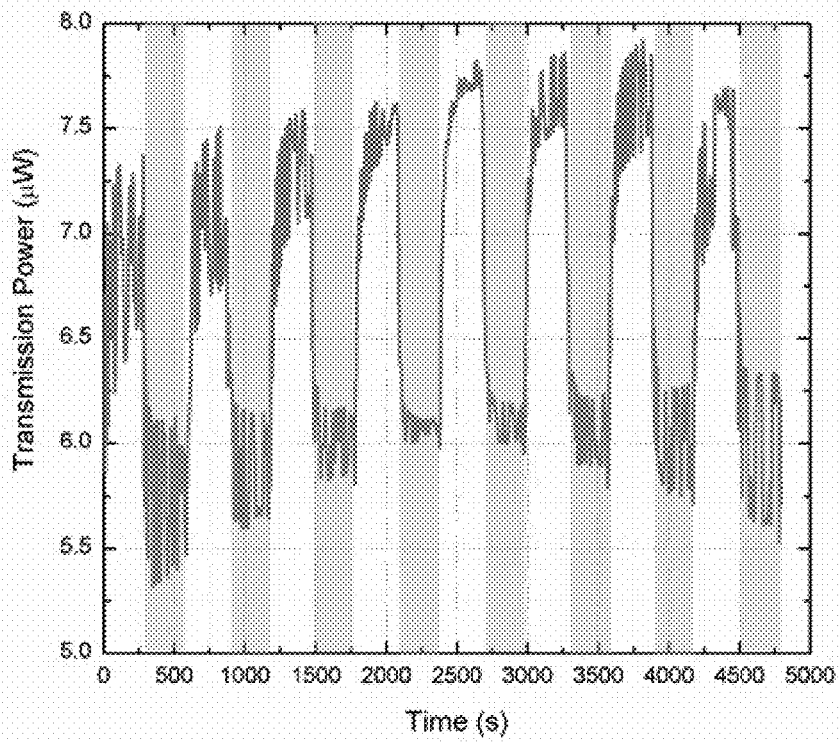
Figure 58B:
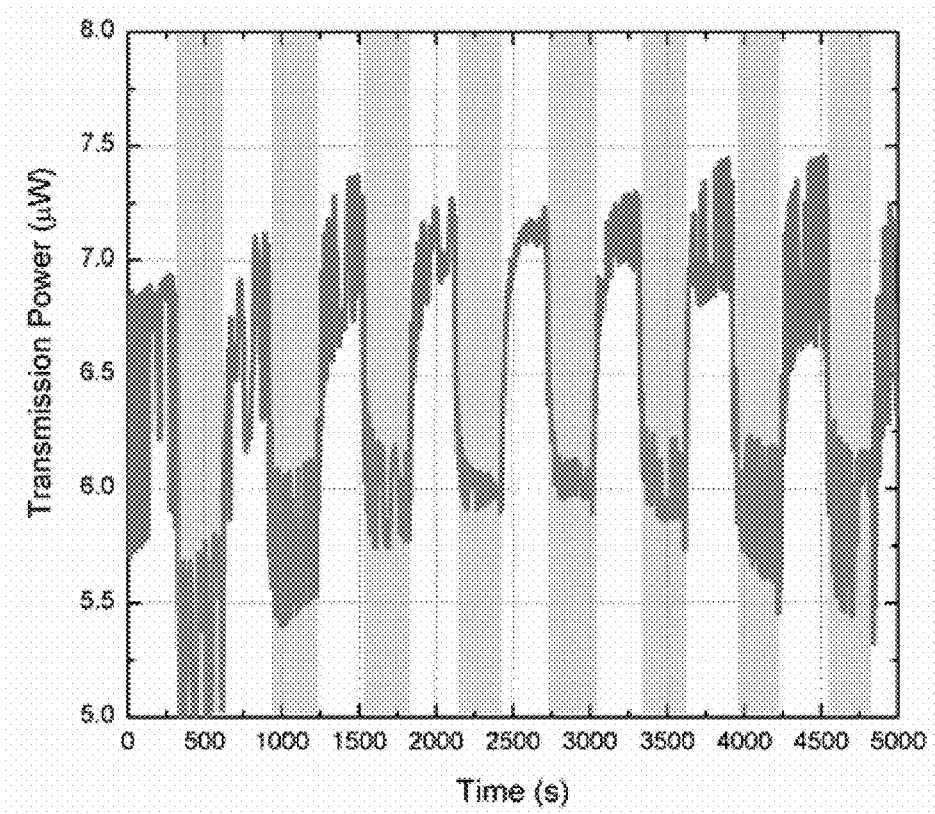
Figure 58C:
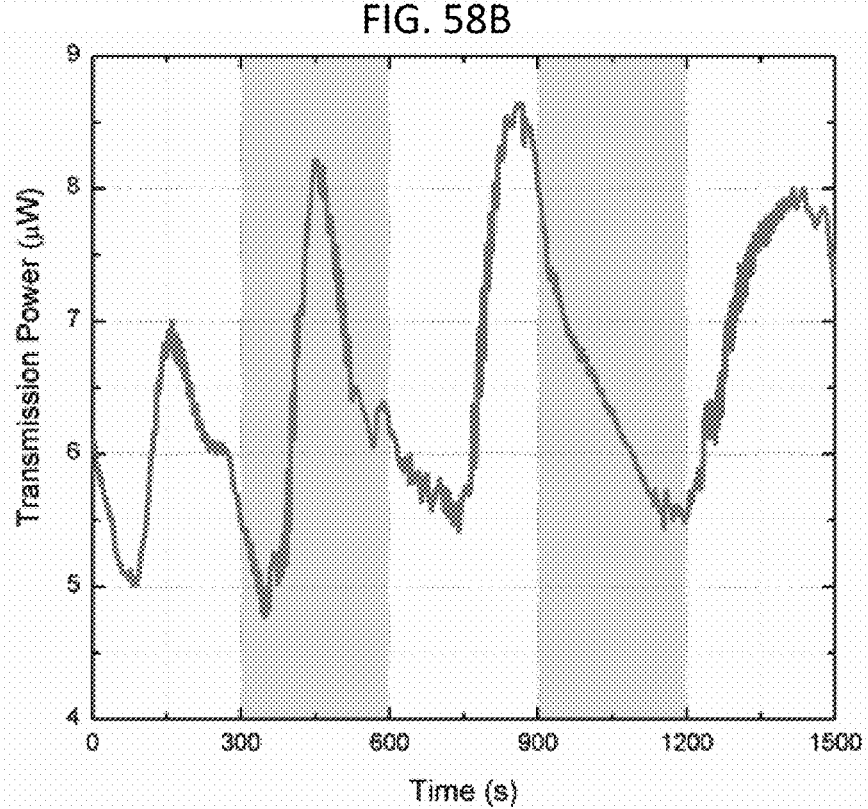

FIGS. 58A-58C are graphs illustrating real time output power of the sensor cell in FIG. 56 at 1572.5 nm (FIG. 58A), 1500 nm (FIG. 58B), and 632 nm (FIG. 58C); gray area indicate the $CO_2$ flowing.

DETAILED DESCRIPTION

I. Explanation of Terms

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

The present disclosure is directed toward all novel and non-obvious features and aspects of the various disclosed embodiments, alone and in various combinations and sub-combinations with one another. Any theories of operation are to facilitate explanation, but the disclosed devices and methods are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed devices, materials, and methods can be used in conjunction with other devices and methods. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or devices are referred to as "lowest," "best," "minimum," or the like. It will be appreciated that such descriptions are intended to indicate that a selection among many used functional alternatives can be made, and such selections need not be better, smaller, or otherwise preferable to other selections.

Examples are described with reference to directions indicated as "above," "below," "upper," "lower," and the like. These terms are used for convenient description, but do not imply any particular spatial orientation.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided:

Near-Infrared Light: Light having a wavelength ranging from 0.75 μm to 2.5 μm.

Sensing Component: A device component comprising a metal-organic framework material, a plasmonic nanomaterial, or a combination thereof.

Light Source: A device capable of acting as a source of illumination, typically capable of producing light falling within the ultraviolet, visible, or infrared region (e.g., 200 nm to 1 mm) of the electromagnetic spectrum, such as the ultraviolet-visible region (e.g., 0.2 μm to 0.75 μm), the near-infrared region (e.g., 0.75 μm to 2.5 μm), the short-wavelength infrared region (e.g., 2.5 μm to 3.5 μm), the mid-infrared region (e.g., 3.5 μm to 8 μm), the long-wavelength infrared region (e.g., 8 μm to 15 μm), the far-infrared region (e.g., 15 μm to 1000 μm).

Gold Nanowires/Antennas/Nanorods: Gold-containing nanomaterials that are structurally distinct from gold nanoparticles, such as those having ellipsoidal or spherical shapes. Gold nanowires or gold antennas, as disclosed herein, can have a particular length, width, and thickness that differs from that of a gold nanoparticle.

I. Overview

Disclosed herein are embodiments of sensor devices that can be used to determine the presence of detectable species in the environment or produced in a variety of industrial applications. The disclosed sensor devices also provide sensitive detection of such detectable species and can be used for a variety of applications. The disclosed sensor devices and materials used with these devices provide several advancements over conventional sensor devices and the materials used to make such devices, some of which are discussed below.

Conventionally, bench-top Fourier transform IR spectrometers are used to detect gases for chemical analysis; however, these instruments exhibit relative low sensitivity and often are used only for in-lab analyses as the instruments are expensive and difficult to transport due to size. Mid-IR absorption or tunable laser diode absorption sensors have been developed in the art to improve sensitivity; however, these types of devices are also very expensive as they require expensive lasers and can also require chalcogenide waveguides. Such devices also can only be used as individual sensors and therefore are not scalable for use in sensor networks.

Fiber-optic evanescent field sensors have been used for chemical sensing, gas sensing, and biosensing; however, the sensing mechanism of such sensors requires penetration of the evanescent field of a totally internally reflected light into the absorbing layer and therefore suffers from low sensitivity. This low sensitivity problem is only increased when used to detect gases.

In addition to the challenges discussed above for conventional sensors, there are additional issues associated with detecting changes in optrode properties of detectable species in such sensors (e.g., resistance of ZnO, pH value of dyes, and refractive index changes of surrounding layers). For example, pH value sensors typically are not able to differentiate between two gas species, particularly $CO_2$ and $NH_3$.

The present disclosure concerns sensor devices that can address many of the challenges that have not been addressed by conventional gas sensors. The devices disclosed herein can be used as NIR absorption sensors (e.g., near-infrared or "NIR" sensors) for gas detection while also still being transportable, low in cost, compact in size, and exhibits distributed sensing capability. The inventors of the embodiments described herein have discovered that metal-organic frameworks (also referred to herein as "MOFs" or "MOF materials") can be used to improve the sensitivity of absorption sensors. The inventors have further discovered that MOF materials can be combined with plasmonic nanomaterials to not only improve sensitivity, but to also improve absorption efficiency. Thus, utilizing these inventive features (either alone or in combination), the inventors have discovered that it is possible to obtain sensor devices, such as infrared sensors (e.g., NIR sensors), sensor devices capable of detecting direct optical constant changes of the MOF material, sensor devices capable of detecting indirect changes of the MOF material, such as index changes of the MOF material through modifications to the surface plasmon resonance of the plasmonic materials in contact with the MOF. Such modifications can be observed using, for example, surface-enhanced Raman spectroscopy sensing techniques, IR sensing techniques, refractive index sensing techniques, and combinations thereof. Thus, in some embodiments, the disclosed devices can be used with a variety of wavelengths to observe detectable changes in the MOF materials (alone or in combination with the plasmonic nanomaterials disclosed herein). Such wavelengths can include, but are not limited to, visible light wavelengths, UV light wavelengths, or other infrared wavelengths other than just NIR. In some embodiments, the sensors be used to determine the presence of, detect, and/or quantify detectable species in a variety of environments and contexts. The devices disclosed herein also can be used to build sensor networks or systems that can monitor detectable species, particularly storage of such species (e.g., $CO_2$ storage).

II. Sensor Devices and Materials

Disclosed herein are embodiments of sensor devices useful for determining the presence of detectable species. In some embodiments, the sensor devices can detect and quantify particular detectable species and further identify these species. The inventors have discovered suitable materials that enhance performance of the devices as compared to conventional devices without such materials. In some embodiments, the sensor devices comprise a sensing component comprising an MOF material capable of adsorbing and/or absorbing the detectable species. In some embodiments, the sensor devices comprise a sensing component comprising plasmonic nanomaterials that can provide enhanced sensitivity such as enhanced NIR sensitivity. In yet additional embodiments, the sensing component can comprise a combination of these MOF materials and plasmonic nanomaterials. The disclosed sensor devices can be used to determine the presence of different detectable species and further differentiate these different detectable species.

A. Metal-Organic Frameworks (MOFs)

The metal-organic framework materials described herein are highly porous crystalline materials comprising one or more metal ions and one or more bridging organic ligands coupled to the metal ions. The metal ions and ligands can be coupled via coordination bonds that can be covalent and/or ionic (e.g., electrostatic). The MOFs disclosed herein can be made to exhibit high surface area and tunable nanostructured cavities, and can be modified both chemically and physically. The MOFs disclosed herein also can rapidly adsorb and/or absorb detectable species, such as gases and volatile organic compounds, within pores formed in the MOFs. The MOFs can be readily recycled as the physisorbed detectable species can be evacuated from the MOF material by subjecting it to dynamic vacuum or flowing inert gases, thereby providing the ability to reuse the MOF material in a subsequent application.

In some embodiments, the metal ions used in the MOFs can be selected from metals capable of forming one or more coordination bonds with a mono-, di-, tri-, or tetra-valent ligand. In some embodiments, the one or more metals can be selected from a Group 2 metal or a metal belonging to any one of Groups 7-13 metal (wherein "Group" refers to a group of the Periodic Table), or a combination thereof. In some embodiments, multiple metal ions of a single species, or a cluster thereof, can be used. In yet additional embodiments, multiple metal ions of two or more species, or a cluster thereof, can be used. In exemplary embodiments, the metal can be selected from copper, silver, gold, aluminum, zinc, cobalt, nickel, magnesium, manganese, iron, cadmium, beryllium, calcium, titanium, tin, chromium, vanadium, or a combination thereof.

The organic ligands used in the MOFs disclosed herein can be selected from mono-, di-, tri-, or tetra-valent ligands. In some embodiments, the ligand can be a bidentate carboxylic acid ligand (or a carboxylate thereof), a tri-dentate carboxylic acid ligand (or carboxylate thereof), an azole ligand, or a combination thereof. Exemplary ligands include, but are not limited to, oxalic acid, malonic acid, succinic acid, glutaric acid, phthalic acid, terephthalic acid, citric acid, trimesic acid, benzene-1,3,5-tricarboxylic acid (BTC), 4,6-dioxido-1,3-benzenedicarboxylate (DOBDC), 1,2,3-triazole, pyrrodizaole, squaric acid, 1,4-diazabicyclo[2.2.2]octane) (DABCO), 1,4-naphthalenedicarboxylate (NDC), 3,6-di(pyridin-4-yl)-1,2,4,5-tetrazine (DPTZ), N,N'-di(4-pyridyl)-1,4,5,8-naphthalenediimide (dpNDI), biphenyldicarboxylate, and combinations thereof.

In particular disclosed embodiments, the MOF material can be modified to improve the electronic conductivity of the MOF material. In some embodiments, the electronic conductivity can be improved or enhanced by including a dopant, such as 12, into the MOF material. In additional embodiments, the MOF material can be modified to include an organocyanide moiety or an organocyanide-containing ligand to enhance the conductivity of the MOF material. Exemplary organocyanide-containing ligands include, but are not limited to, 7,7,8,8-tetracyanoquinodimethane (TCNQ), tetracyanoethylene (TCNE), and N,N'-dicyanoquinonediimine (DCNQI). In yet another embodiment, the MOF material can be modified or used in combination with a layer of conductive material, such as polyaniline.

In exemplary embodiments, the MOF material can comprise, consist essentially of, or consist of the metal and ligand components described above. Embodiments consisting essentially of the metal and ligand components described herein are free of any component that would affect the MOF material's ability to adsorb and/or absorb gases and/or its ability to readily be recycled. In exemplary embodiments, the MOF material can comprise, consist essentially of, or consist of Al(fumarate)(OH), Zn(methylimidazolate)$_2$, Co(methylimidazolate)$_2$, or Cu$_3$(BTC)$_2$, Ni$_2$(DOBDC), or a combination thereof.

Figure 1:
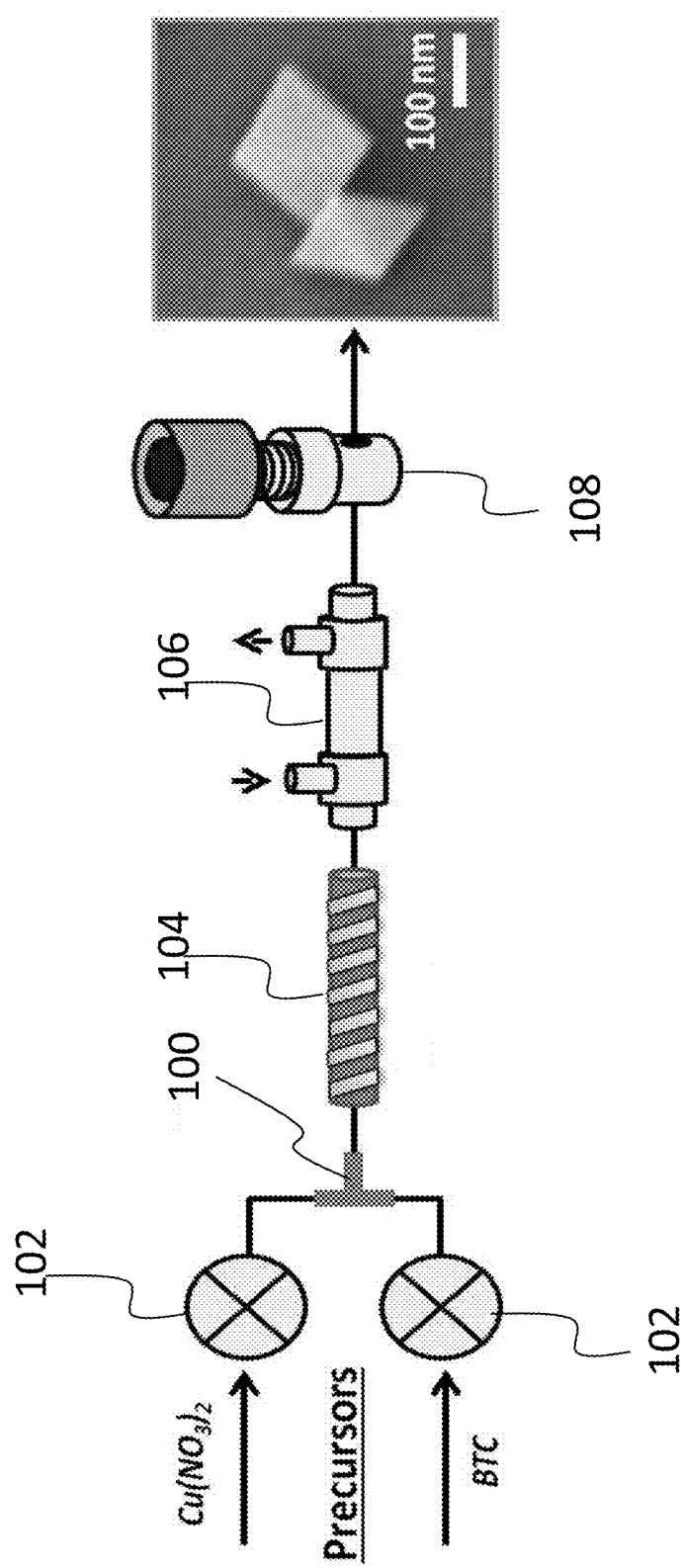
FIG. 1 is a schematic diagram illustrating an exemplary system for making exemplary metal-organic framework (MOF) materials disclosed herein.

The MOF material can be made by using a growth technique whereby layers of MOF material are deposited onto a substrate component of the sensor device, such as in a layer-by-layer ("LBL") method. The layer-by-layer deposition technique can comprise immersing the substrate into an MOF precursor solution, a ligand solution, or a combination thereof. In some embodiments, the substrate is first immersed in the MOF precursor solution and then subsequently immersed in the ligand solution. In yet other embodiments, the order of immersion can be reversed, or the substrate can be immersed in a solution comprising a mixture of the MOF precursor and the ligand. The MOF precursor solution can comprise any of the metals described above for use in the MOF material. In some embodiments, the MOF precursor solution can be selected from solutions comprising metal acetates, metal nitrates, or combinations thereof. Exemplary MOF precursors can include, but are not limited to Cu(OAc)$_2$, Zn(OAc)$_2$, Ni(OAc)$_2$, Zn(NO$_3$)$_2$.6H$_2$O, Cu(NO$_3$)$_2$.2.5H$_2$O, Co(NO$_3$)$_2$.6H$_2$O. In some embodiments, the metal precursor and/or the ligand can be combined with a solvent, such as an alcohol (e.g., methanol, ethanol, isopropanol, etc.), water, or a mixture thereof. The substrate can be rinsed with solvent and dried under an inert gas between each application of the metal precursor, ligand, or combination thereof. In other embodiments, the MOF materials can be prepared using a system as illustrated in FIG. 1. As illustrated in FIG. 1, the metal precursor and the ligand precursor can be introduced into a T-mixer 100 using pumps 102. The mixed precursors can then be transferred to a reactor 104 and then to cooler 106. The cooled mixture is then passed through a back pressure regulator 108 to provide crystals of the MOF material.

In some embodiments, the amount of metal precursor used may be selected to provide a corresponding crystal size in the MOF material. In some embodiments, the metal precursor can be selected to provide crystal sizes ranging from 100 nm to 350 nm, such as from 125 nm to 325 nm, or 100 nm to 300 nm. In an exemplary embodiment, the crystal size of the MOF material was 300 nm. The MOF materials can be grown directly on a substrate to form a film or they can be formed into a film and then coupled to a substrate. Suitable substrates and coupling methods are described in more detail herein.

In some embodiments, the MOF material can be provided as or grown as a thin film or a thick film. Exemplary thin films can be have thicknesses ranging from greater than zero nanometers to several hundred nanometers, such as 1 nm to 500 nm or more, or 10 nm to 200 nm or more, or 50 nm to 100 nm or more. Exemplary thick films can have thicknesses ranging from at least 500 nm to several micrometers, such as 500 nm to 50 μm or more, or 1 μm to 20 μm or more, or 5 μm or 10 μm or more. In one exemplary embodiment, a thin film of the MOF material was grown onto a substrate and had a thickness of 100 nm. Exemplary embodiments of deposited MOF materials are shown in FIGS. 2-5. FIG. 2 shows an optical image of the core of an optical fiber prior to deposition and FIG. 3 shows an optical image of the core of the optical fiber after deposition. FIGS. 4 and 5 are SEM images of the MOF-coated fiber; FIG. 4 shows a cross section view of the coated fiber and FIG. 5 shows a top view of the coated fiber. FIG. 6 is an AFM image of an optical fiber coated with an exemplary MOF.

B. Plasmonic Nanomaterials

Disclosed herein are embodiments of plasmonic nanomaterials that can be used in the sensor devices. In some embodiments, the plasmonic nanomaterials can be used to enhance the absorption efficiency of the sensor devices disclosed herein. In some embodiments, the plasmonic nanomaterials can be plasmonic nanocrystals, nanowires, nanorods, or a combination or array thereof.

Plasmonic nanomaterials can be used in the devices disclosed herein as these materials have unique surface plasmon resonance properties in the NIR region; however, the present disclosure is not limited to applications in the NIR region and the embodiments disclosed herein can be used in combination with light sources capable of producing light falling within the ultraviolet, visible, or other infrared regions. Some embodiments of plasmonic nanomaterials comprise a dopant. In some embodiments, a particular peak wavelength can be obtained by controlling the amount of dopant present in the plasmonic nanomaterials. This peak wavelength can be manipulated to be the same as, or substantially the same as the overtone of molecule vibration bands in NIR wavelengths of the detectable species thereby increasing the absorption sensitivity and efficiency of the devices disclosed herein. In some embodiments, this peak wavelength may be sensitive to external conditions surrounding the particle such as effective refractive index or it may be sensitive to charge transfer to and from the plasmonic material as a result of interactions of the plasmonic material or the MOF material with a detectable species of interest.

In some embodiments, the plasmonic nanomaterials disclosed herein can comprise a metal oxide, a metal sulfide, one or more dopants, and combinations thereof. Metal oxides and/or metal sulfides that can be used to make the plasmonic nanomaterials can include metal oxides and metal sulfides that are resistant to high temperatures (e.g., temperatures ranging from greater than 100° C. to 400° C., such as 200° C. to 400° C., or 250° C. to 350° C.). The metal oxides or metal sulfides also can be catalytically active and optically transparent in visible wavelengths. In some embodiments, the metal oxides can be selected from indium oxides (e.g., $In_2O_3$), tin oxides (e.g., $SnO_2$), titanium oxides (e.g., $TiO_2$), zirconium oxides (e.g., $ZrO_2$), cesium oxides (e.g., $CeO_2$), zinc oxides (e.g., ZnO), copper oxides (e.g., CuO), gallium oxides (e.g., $Ga_2O_3$), or combinations thereof. In some embodiments, the metal sulfides can be selected from indium sulfides (e.g., $In_2S_3$), tin sulfides (e.g., SnS or $SnS_2$), titanium sulfides (e.g., $TiS_2$), zirconium sulfides (e.g., $ZrS_2$), cesium sulfides (e.g., $CeS_2$), zinc sulfides (e.g., ZnS), copper sulfides (e.g., CuS, $Cu_2S$, or $CuS_2$), gallium sulfides (e.g., $Ga_2S_3$), or combinations thereof. In some embodiments, the metal oxide or the sulfur oxide can be doped with a dopant selected from, for example, Pd, Pt, Au, Sn, Al, Nb, or Ta. In one embodiment, Sn-doped indium oxide nanocrystals were used as an exemplary plasmonic nanomaterial. Another exemplary plasmonic nanomaterial that can be used is aluminum zinc oxide nanoparticles. In yet other embodiments, the plasmonic nanomaterials can comprise or consist of a combination of dopants, with one exemplary embodiment being Cu:In:Se nanocrystals.

In yet other embodiments, the plasmonic nanomaterials can comprise or consist of a metal or alloy. The plasmonic nanomaterials also may be nanoparticles having a single material core structure or an inner core and an outer shell comprised of the same or different materials. In some embodiments, the plasmonic nanomaterials are gold nanorods or gold antennas that can be used to form arrays. Gold nanorods and gold antennas as disclosed herein are different from gold nanoparticles, such as spherical/ellipsoidal gold nanoparticles. In independent embodiments, the gold nanomaterials are other than or are not spherical/ellipsoidal gold nanoparticles, which in such independent embodiments, do not have the same length:width:thickness dimensions as the gold nanowires, nanorods, or gold antennas disclosed herein. Some exemplary gold nanomaterials include gold nanowires, gold nanorods, or gold antennas that have geometries, dimensions, and properties not exhibited by spherical gold nanoparticles, such as tunable plasmonic wavelengths. In another independent embodiment, the plasmonic nanomaterials are not or are other than platinum nanoparticles, or palladium nanoparticles used in combination with ZnO nanorods.

In some embodiments, the plasmonic nanomaterials can be in the form of discrete nanocrystals or nanoparticles, nanowire arrays, nanorod arrays, hollow antenna arrays, dipole antenna arrays, or a combination thereof. Nanocrystals disclosed herein can have core sizes ranging from 5 nm to 100 nm, such as 8 nm to 50 nm, or 8 nm to 20 nm, or 8 nm to 15 nm. In one exemplary embodiment, the nanocrystals had core diameters of 10 nm.

Figure 7:
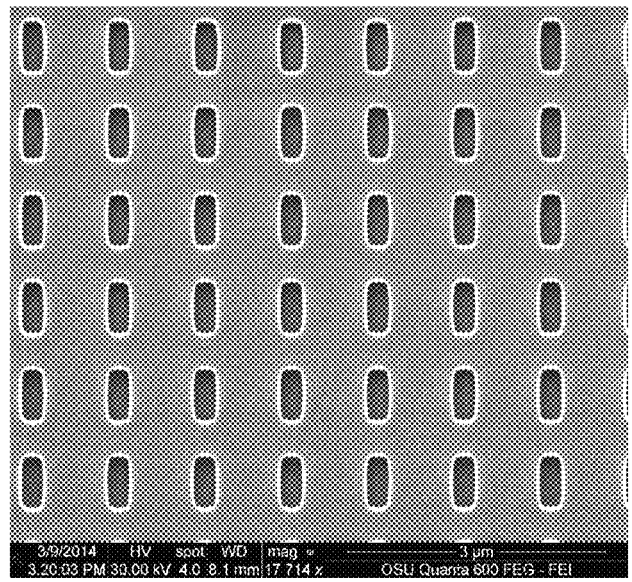
FIG. 7 is an image of a poly(methyl methacrylate) (PMMA) pattern after developing used to form an exemplary gold nanowire array.
Figure 8:
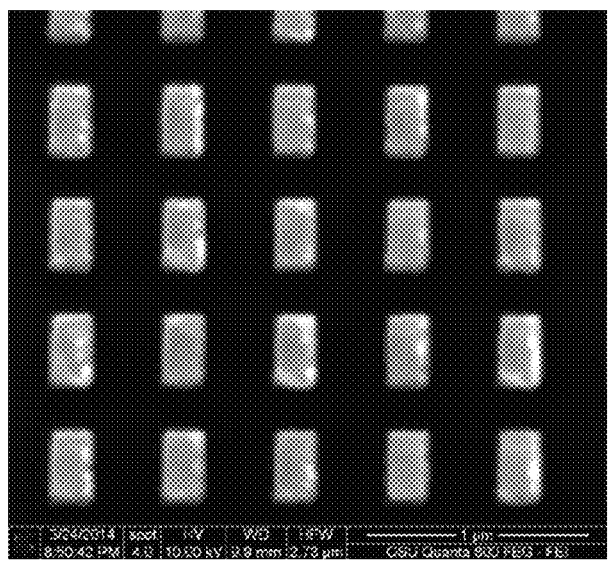
FIG. 8 is an image of a gold nanowire array after lift-off from the PMMA template shown in FIG. 7.

Nanorod arrays can comprise nanorods having dimensions ranging from greater than zero nanometers to several hundred nanometers wide, greater than zero nanometers to several thousand nanometers long, and greater than zero nanometers to several hundred nanometers thick. In some embodiments, the dimensions can range from 10 nm to 300 nm (or greater) wide, 20 nm to 2000 nm (or greater) long, and 10 nm to 500 nm (or greater) thick. In particular disclosed embodiments, the nanorods of the nanorod arrays can be 200 nm wide, 400 nm long, and 100 nm thick. In some embodiments, the length of the nanorod can be modified to tune the plasmonic resonant wavelength of the array. Exemplary nanorod arrays are illustrated in FIGS. 7 and 8. In some embodiments, dipole antenna arrays can be used to enhance the NIR enhancement obtained with certain sensor device embodiments. In some embodiments, the dipole antennas of the antenna array can have dimensions ranging from greater than zero nanometers to several hundred nanometers wide, greater than zero nanometers to several thousand nanometers long, and greater than zero nanometers to several hundred nanometers thick. In some embodiments, the dimensions can range from 10 nm to 300 nm (or greater) wide, 20 nm to 2000 nm (or greater) long, and 10 nm to 500 nm (or greater) thick. In one exemplary embodiment, the dipole antennas were 200 nm wide, 420 nm long, and 100 nm thick. The distance between the dipole antennas can range from 25 nm to 200 nm, such as 25 nm to 150 nm, or 50 nm to 100 nm. In one exemplary embodiment, the distance between the dipole antennas was 50 nm. In some embodiments, the length of the nanorod can be modified to tune the plasmonic resonant wavelength of the array. In other embodiments, the geometry of the array can be modified to optimize the sensitivity of the array in response to changes in effective refractive index of a surrounding MOF material or to changes in the free carrier density of the plasmonic materials due to interactions of a composite material with an analyte.

Figure 9:
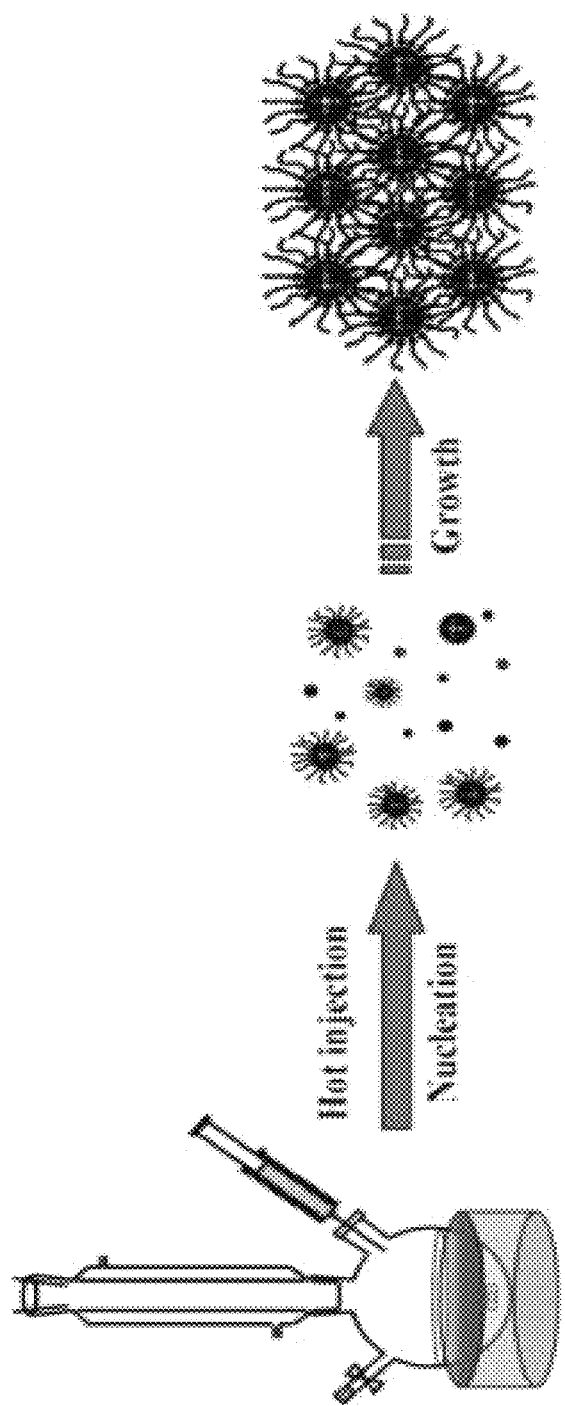
FIG. 9 is a schematic diagram of an exemplary method for synthesizing plasmonic nanomaterials disclosed herein.
Figure 10:
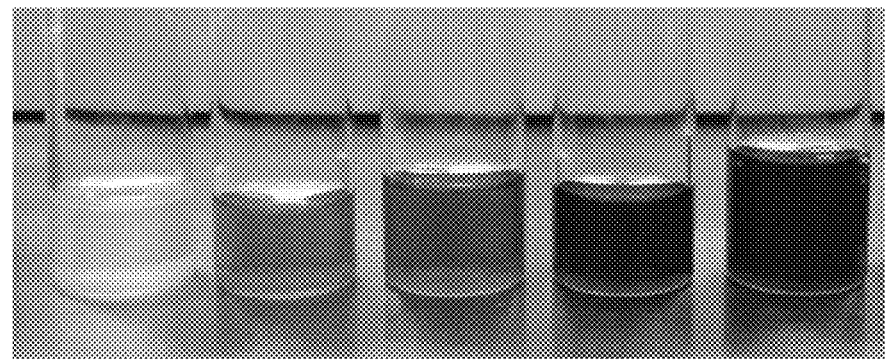
FIG. 10 is a photographic image of plasmonic nanomaterials in solution at varying concentrations.
Figure 11:
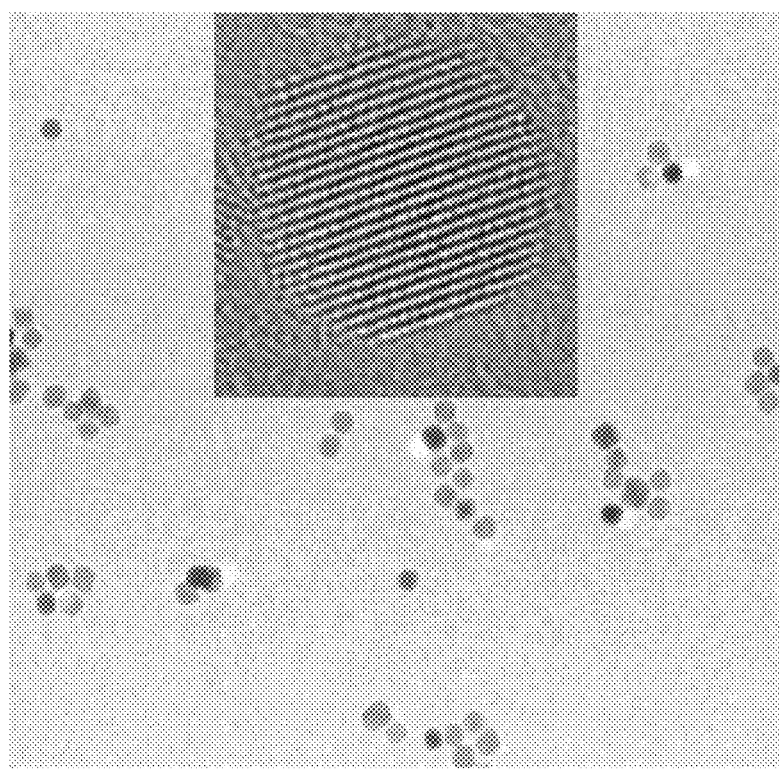
FIG. 11 is a TEM image of exemplary plasmonic nanomaterials.

In some embodiments, the plasmonic nanomaterials can be made by using an embodiment of a hot-injection method, such as that illustrated schematically in FIG. 9. Such hot-injection methods can comprise combining a metal oxide precursor, one or more ligand precursors, and a dopant precursor. These components can be added sequentially or simultaneously in any order, and combinations thereof. In some embodiments, the metal oxide precursor, dopant precursor, and a first ligand precursor are mixed under vacuum at a suitable temperature. One or more solvents can be used to facilitate mixing, with such solvents being selected from organic solvents, such as octadecene or other hydrocarbon-based solvents. These components can be mixed at such temperatures for a time period ranging from 5 minutes to 60 minutes, such as 10 minutes to 50 minutes, or 20 minutes to 40 minutes. A solution of a second ligand precursor can be added to the mixture of the metal oxide precursor, dopant precursor, and first ligand precursor. The resulting reaction mixture can then be mixed at a suitable temperature and for a suitable time so as to provide a solution of nanocrystals. After this time period, the reaction mixture can be allowed to cool to ambient temperature and the nanocrystals can be isolated and precipitated using methods known to persons of ordinary skill in the art. Exemplary isolated nanomaterials are shown in FIGS. 10 and 11. FIG. 10 illustrates solutions of exemplary nanocrystals in varying concentrations. FIG. 11 shows exemplary nanocrystals.

C. Combined Sensing Component

Figure 12:
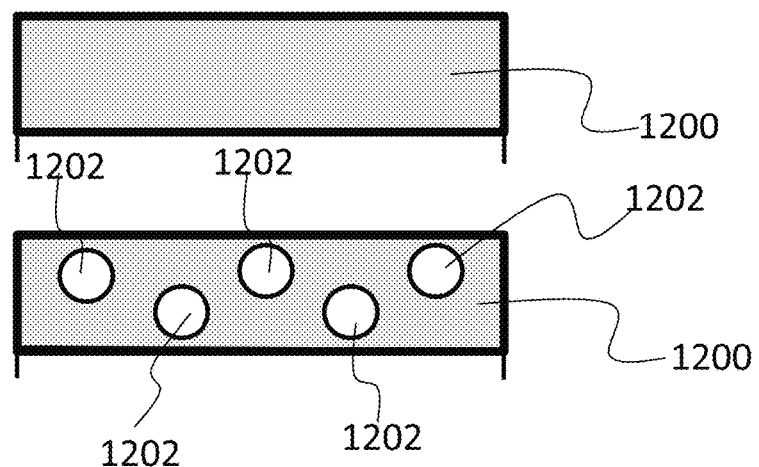
FIG. 12 is a schematic diagram of an exemplary combined sensing component comprising plasmonic nanoparticles embedded in an MOF material.
Figure 13:
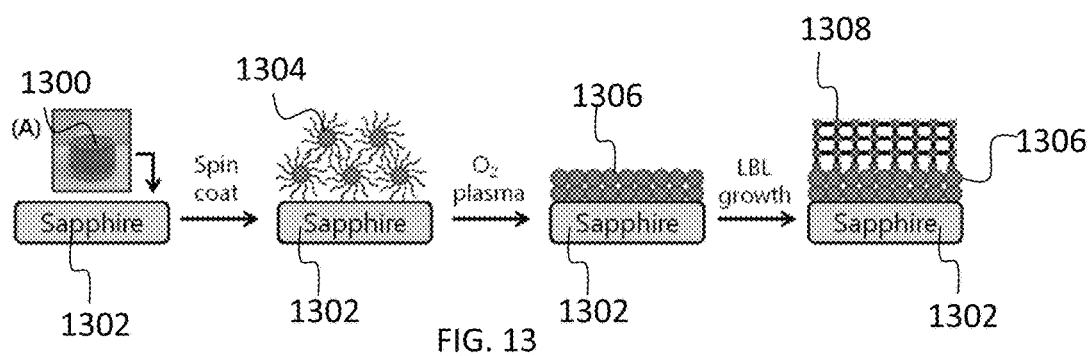
FIG. 13 is a schematic diagram illustrating an exemplary method of preparing an MOF//ITO/Sapphire embodiment.

The MOF embodiments disclosed herein can be used in combination with plasmonic nanomaterials to provide a combined sensing component. In some embodiments where the MOFs and plasmonic nanomaterials are used in combination, the plasmonic nanomaterials can be contained within pores of MOF materials, or otherwise embedded in the MOF material, such as is illustrated in FIG. 12. As illustrated in FIG. 12, plasmonic nanomaterials 1200 can be embedded in an MOF material 1202. In some embodiments, multiple layers of the combined sensing component can be used. In yet some additional embodiments, a layer of MOF material can be placed between two or more layers of nanoparticles. In these embodiments, any suitable order of addition is contemplated to form the different layers of MOF material and plasmonic nanomaterials. For example, a first layer of plasmonic nanomaterial can be deposited onto a substrate, followed by deposition of a layer of MOF material; this process can then be continued for a desired number of cycles. In some embodiments, a single layer of plasmonic nanomaterial can be deposited onto a substrate, followed by multiple layers of MOF material, such as is illustrated in FIG. 13. As illustrated in FIG. 13, a solution of plasmonic nanomaterial, such as plasmonic nanoparticles 1300 can be deposited onto a substrate, such as sapphire substrate 1302, to provide a layer of plasmonic nanomaterial 1304. Substrate 1302 can then undergo $O_2$ plasma treatment to provide packed plasmonic nanomaterial 1306 capable of reacting with MOF material 1308, which can be grown onto the plasmonic nanomaterial using an LBL method. In yet additional embodiments, the plasmonic nanomaterial can be deposited onto already formed layers of the MOF material, which can be pre-formed and then added to a substrate, or directly grown onto a substrate.

Figure 14:
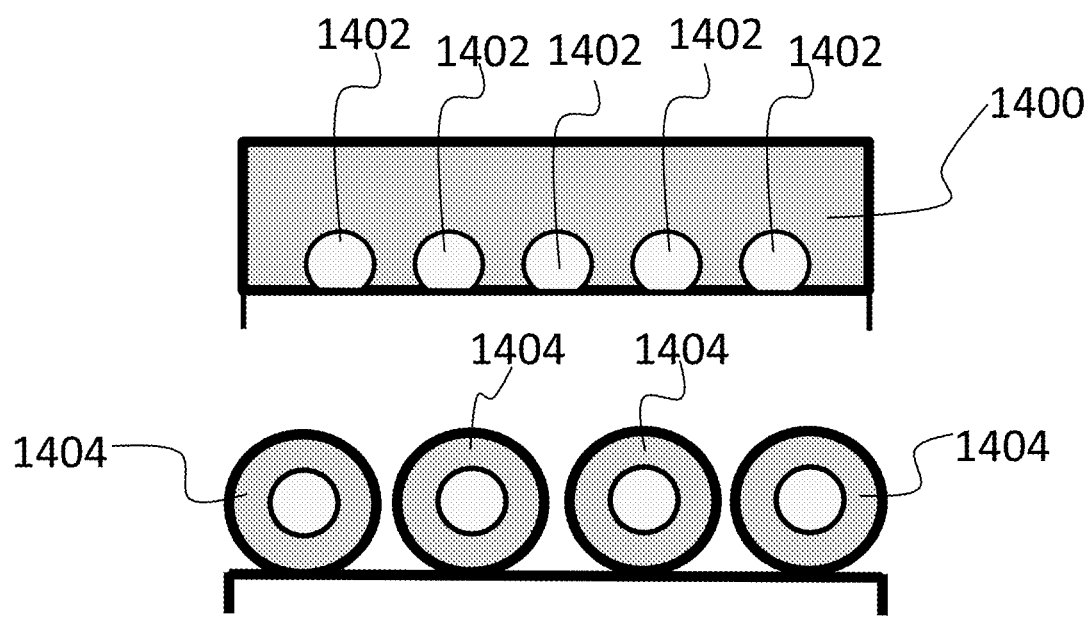
FIG. 14 is a schematic diagram of an exemplary combined sensing component comprising plasmonic nanoparticles encapsulated by an MOF material.

In other embodiments, the plasmonic nanomaterials can be encapsulated by the MOF material, such as is illustrated in FIG. 14. With reference to FIG. 14, an MOF material 1400 and plasmonic nanomaterial 1402 can be combined to form combined sensing components 1404 wherein the plasmonic nanomaterial is encapsulated by the MOF material. In such embodiments, the MOF-encapsulated plasmonic nanomaterials can exist as discrete particles. The layer of MOF material encapsulating the nanomaterials can be controlled so as to provide thin or thick layers of MOF material around the nanomaterial. In some embodiments, the layer of MOF material that encapsulates the plasmonic nanomaterial is not so thick as to prevent absorption of detectable species. Also, the layer of MOF material that encapsulates the plasmonic nanomaterial should be maintained at a thickness that does not hinder the plasmonic field of the plasmonic nanomaterial. In some embodiments, the thickness of the MOF material surrounding the plasmonic nanomaterial can be selected to range from 50 nm to 250 nm, such as 100 nm to 200 nm, or 100 nm to 150 nm so as to prevent hindrance of detectable species absorption and/or hindrance of the plasmonic field of the plasmonic nanomaterial.

An exemplary method for forming MOF-encapsulated plasmonic nanomaterials can include combining an MOF-precursor solution, a pre-formed nanomaterial (e.g., nanoparticles), one or more ligand precursors, and a solvent. Allowing these components to mix briefly (e.g., 5 minutes to 30 minutes, such as 5 minutes to 20 minutes, or 10 minutes to 15 minutes) together at ambient temperature, followed by allowing the mixture to sit at ambient temperature without mixing for a time ranging from 6 hours to 24 hours, such as 12 hours to 24 hours, or 12 hours to 20 hours, can provide the MOF-encapsulated plasmonic nanomaterials. In some embodiments, the MOF-encapsulated plasmonic nanomaterials can be obtained as discrete particles and therefore are not agglomerated. In yet other embodiments, the MOF-encapsulated plasmonic nanomaterials can be allowed to aggregate so as to provide more combined sensing components within a desired surface area.

Embodiments of combined sensing components can exhibit surface plasmon energies that are sensitive to a surrounding environment therefore contributing to their utility in sensing, such as gas sensing. In some embodiments, the particular components of the MOF materials and the plasmonic nanomaterials can be selected to provide a combined sensing component that exhibits a surface plasmon absorption peak at a wavelength that is the same as or substantially overlaps with the vibrational frequency exhibited by the detectable species to be analyzed using the sensor devices disclosed herein. "Substantially overlaps," as used herein, means the vibrational band of the detectable species is within 3-dB bandwidth of the resonant mode. Solely by way of example, the components of the MOF material and the plasmonic nanomaterial can be selected to provide a combined sensing component that can exhibit surface plasmon absorption at a wavelength of 2650 nm to 2750 nm, such as 2700 nm. Such exemplary embodiments can therefore be used to detect and identify gases having vibration frequencies in this range, such as $CO_2$. These combined sensing components, however, can be readily modified so as to provide different surface plasmon absorption at different wavelengths and therefore detect other gas species having similar vibration frequencies to these surface plasmon absorptions. These modifications can include changing the species of the metal component of the MOF, the ligand component of the MOF material, the nanomaterial of the plasmonic nanomaterial, or any combination thereof.

In other embodiments, modifications to the optical response associated with the plasmonic materials can be monitored in response to changes in effective refractive index of a surrounding MOF material or to changes in the free carrier density of the plasmonic materials due to interactions of a composite material with an analyte either directly or mediated via interactions between the MOF material and the analyte followed by charge transfer with the plasmonic material.

D. Substrates

The sensing components described above can be coupled with a variety of substrates to provide the sensor devices disclosed herein. Substrates suitable for use with the disclosed sensing components include, but are not limited to, light guides, such as optical fibers, or substrates that can be coupled with a light guide or a light source, such as wafers, slides, or other solid infrared transparent substrates, such as sapphire-containing substrates, barium fluoride-containing substrates, calcium fluoride-containing substrates, or combinations thereof. The substrate can have any suitable shape that enables its use in detecting and/or quantifying one or more detectable species. In some embodiments, the substrate can have a square, rectangular, oval, elliptical, or circular shape. In exemplary embodiments, the sensing component can be pre-formed and coupled to a substrate or it can be grown directly onto a substrate. In one exemplary embodiment, the substrate was an optical fiber, such as a multi-mode optical fiber or a single-mode fiber. In yet another exemplary embodiment, the substrate was a solid planar substrate, such as a sapphire or silicon substrate.

Figure 15:
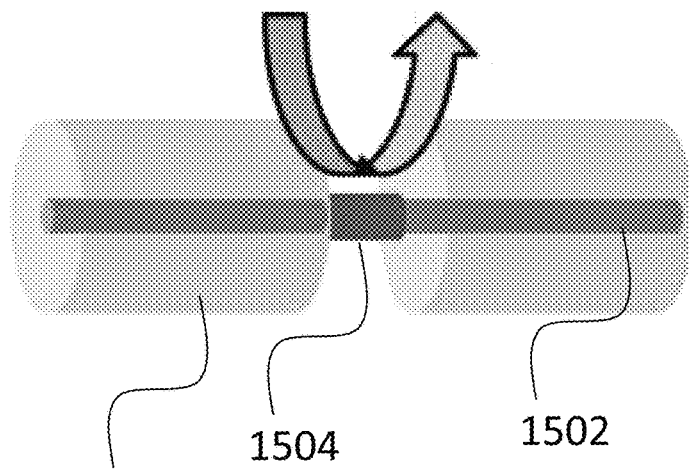
FIG. 15 is an image of an optical fiber comprising a core modified with an exemplary sensing component described herein.
Figure 16:
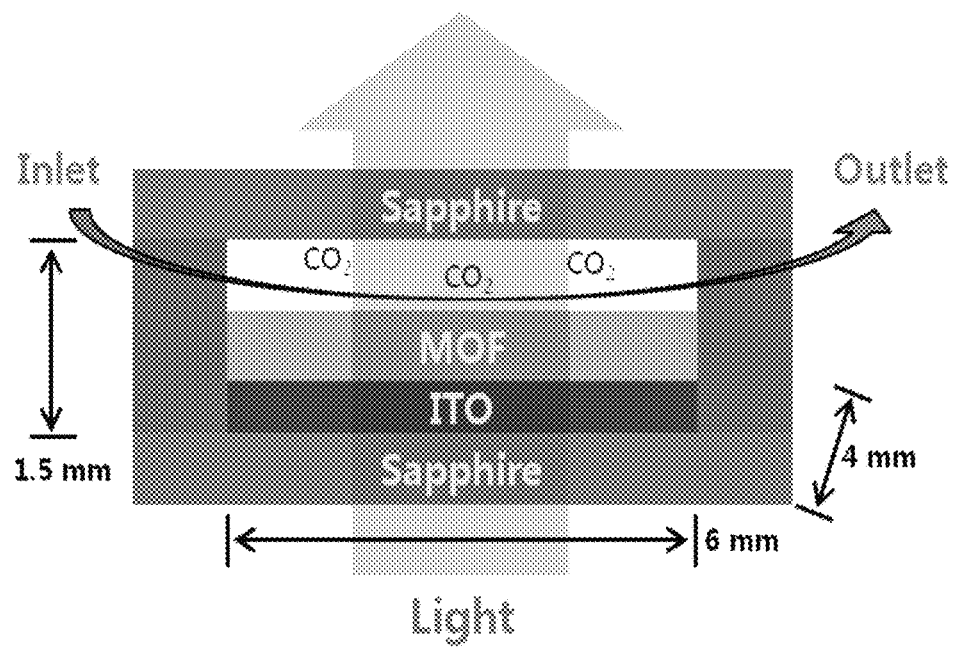
FIG. 16 is a schematic diagram of an exemplary flow-cell used to test the disclosed sensing components disclosed herein.

In particular disclosed embodiments, the sensor device can comprise a substrate having one or more sections modified with a sensing component as described above. In one exemplary embodiment, the core of an optical fiber was coupled to an MOF material, such as is illustrated in FIG. 15. FIG. 15 illustrates an optical fiber substrate 1500 comprising a core 1502, which is coupled to a sensing component 1504 as described herein. In an independent embodiment wherein the substrate is an optical fiber, the surface of the portion of the optical fiber that is coupled to the metal-organic framework material sensing component does not include a base layer of palladium coupled to the optical fiber. In some embodiments, the section of the optical fiber modified with the metal-organic framework material can be further modified with a plasmonic nanomaterial. In such embodiments, the MOF material can be layered with plasmonic nanomaterial layers as described above, or the MOF material can encapsulate the plasmonic nanomaterial as disclosed above. An exemplary embodiment of a substrate coupled with a combined sensing component is illustrated in FIG. 16. In an independent embodiment, the MOF material is used in combination with a plasmonic nanomaterial other than gold nanoparticles. In another independent embodiment wherein the substrate is an optical fiber, the optical fiber is not coupled to multilayers of ZnO and palladium or to a palladium-ZnO composite that is used in combination with a silver coating.

Figure 17:
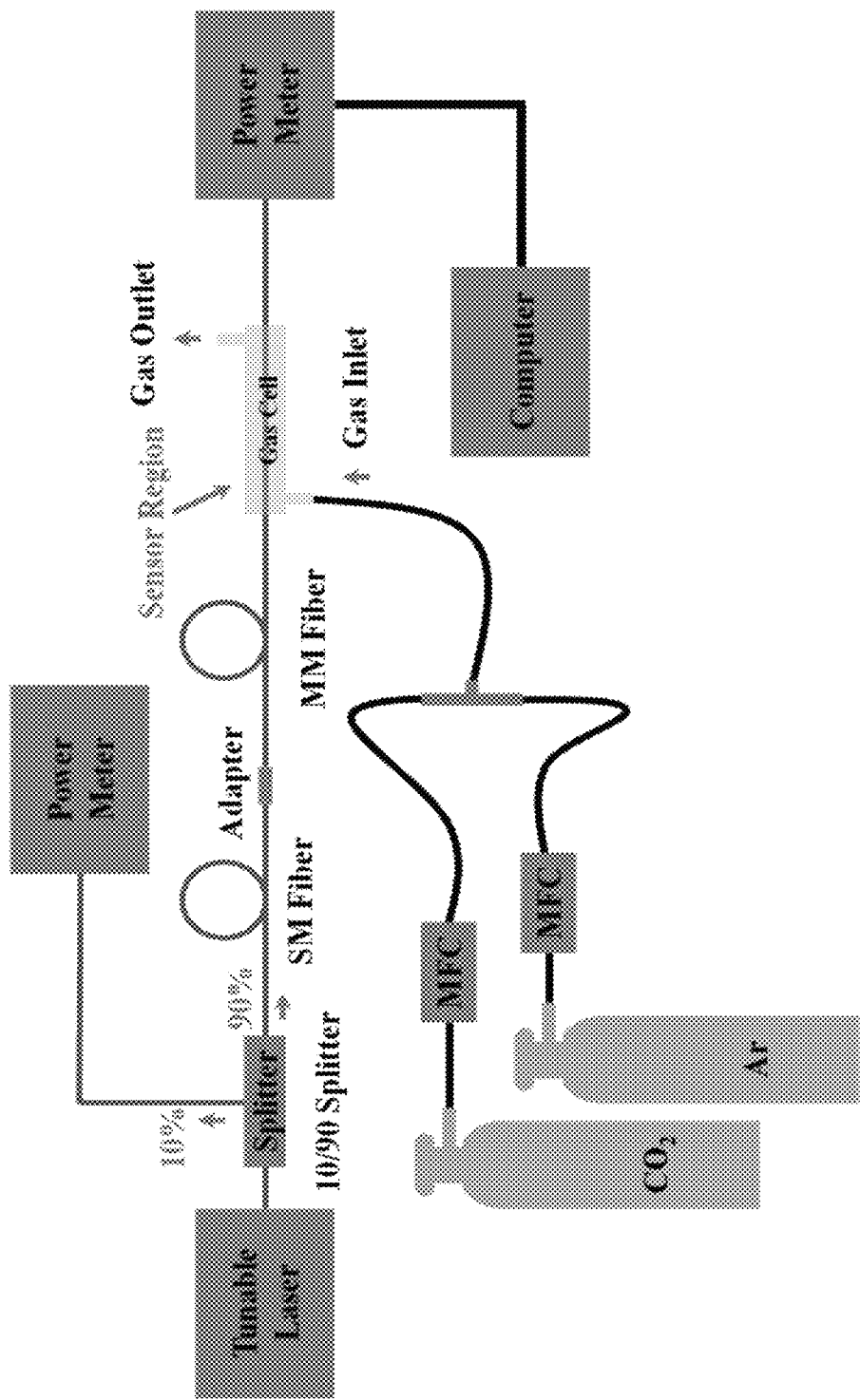
FIG. 17 is a schematic diagram of an exemplary sensor device setup as disclosed herein.
Figure 18:
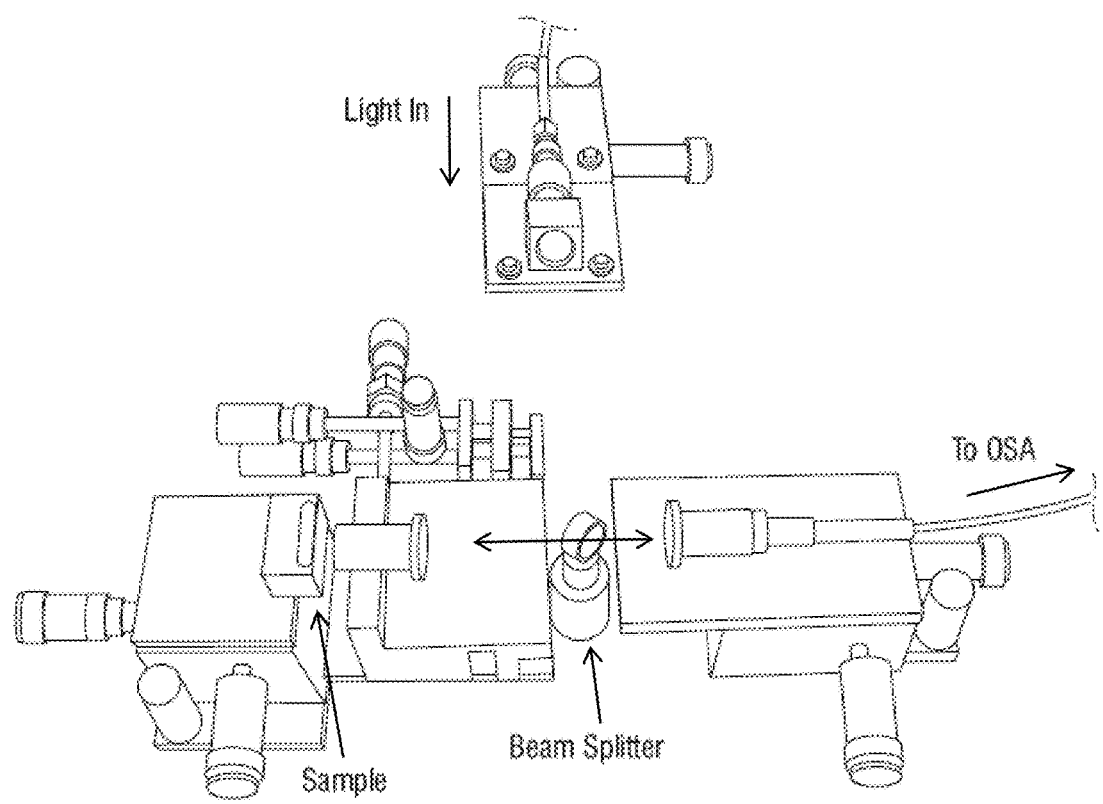
FIG. 18 is a photographic image of an exemplary device setup that can be used to determine reflection measurements.
Figure 19:
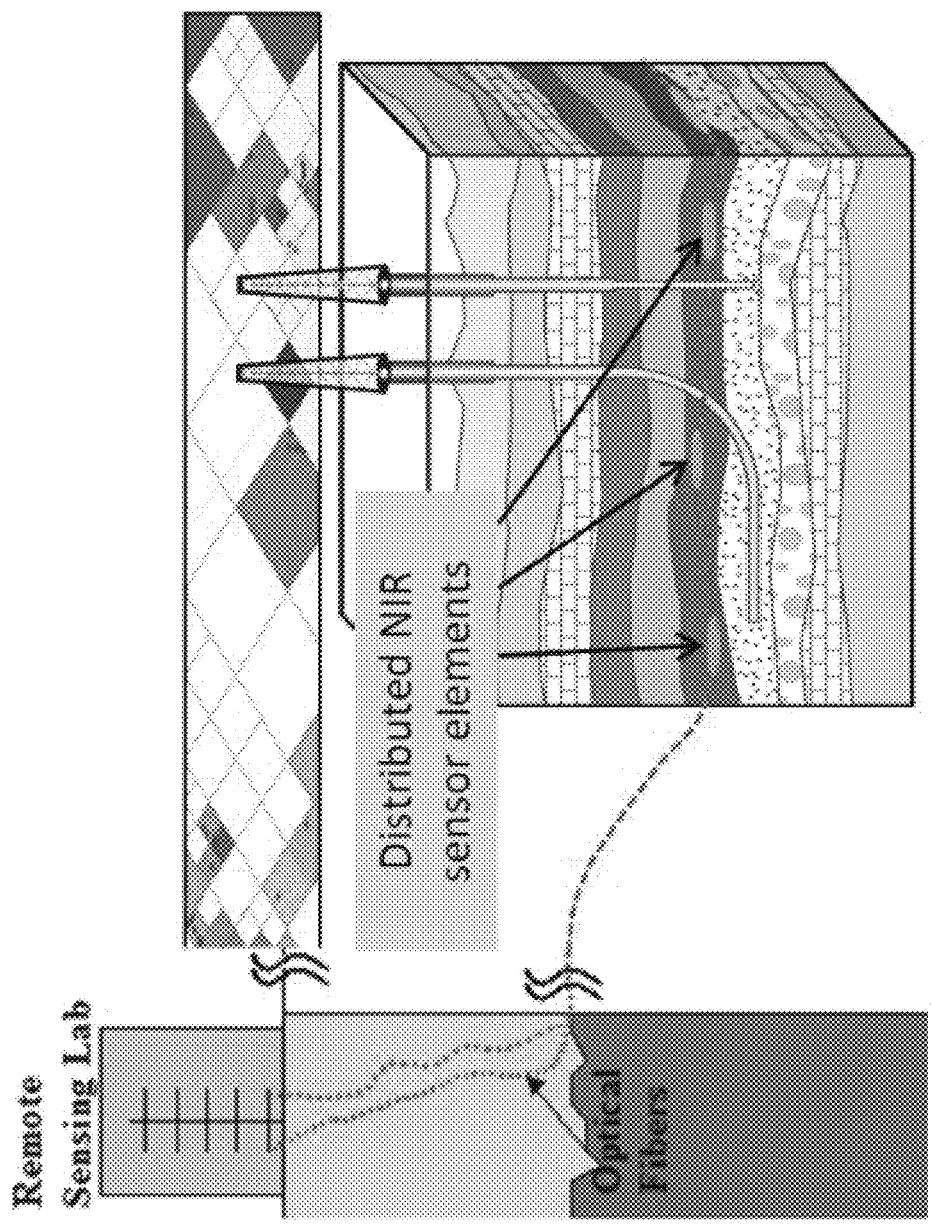
FIG. 19 is a schematic diagram illustrating an exemplary sensing device network setup.

The sensor devices disclosed herein also can comprise one or more additional components that facilitate detection and/or quantification of detectable species. In some embodiments, the one or more additional components can be selected from a light source, one or more adapters, one or more power meters, and a computer or other means suitable for collecting data, and any combination thereof. In some embodiments, the light source can be coupled to or separate from the substrate and sensing component. Suitable light sources will be recognized by those of ordinary skill in the art. In one exemplary embodiment, the light source was a laser, particularly a tunable laser. Adapters can be used with the sensing device so as to couple one or more components together. For example, an adapter can be used to couple the sensing device (e.g., the substrate and sensing component) to the light source, one or more extension components (e.g., an additional light guide that can be used to increase the distance between the light source and the sensing device), the one or more power meters, and/or the computer. In one exemplary embodiment, a light source, such as a laser, was coupled to a beam splitter and power meter as well as an extension fiber, which was coupled to the sensing device via an adapter. The sensing device was coupled to an additional power meter and computer. This exemplary embodiment is illustrated in FIG. 17. Another exemplary embodiment of a device set up is shown in FIG. 18.

III. Methods of Making Sensor Devices

Disclosed herein are embodiments of methods for making the sensor devices disclosed herein. In particular disclosed embodiments, the sensor devices can be made by partially or completely covering a substrate as described above with one or more sensing components, such as by coupling the substrate with the sensing component. The substrate may be pretreated prior to adding the sensing component.

In some embodiments, a selected surface area of the substrate can be modified with any of the sensing components described herein. In some embodiments, the sensing component can partially or completely cover the substrate. In embodiments where the sensing component partially covers the substrate, the substrate can have from about 0.01% to less than 100% of the total surface area of the substrate covered, such as 0.01% to 50%, or 1% to 10% of the total surface area of the substrate It is contemplated herein that the amount of surface area of the substrate that is covered can be modified as needed to achieve a desired sensing result without sacrificing performance and efficiency. In particular disclosed embodiments using a light guide substrate, the selected surface area can include a distance of 4 cm to 20 cm of the light guide that can be coupled to the sensing component, such as 6 cm to 15 cm, or 7 cm to 9 cm. These surface area distances can be scaled as necessary depending on the size of the substrate. In embodiments where an optical fiber is used, the sensing component thereof can cover the entire circumference of the optical fiber, or only a portion thereof. In one exemplary embodiment, the sensing component was coupled to an optical fiber to provide 8 cm of covered surface area.

In some embodiments, more than one selected surface area region can be covered with the sensing component by coupling the selected surface area region with the sensing component. For example, a plurality of surface area regions can be spaced apart throughout a selected length of the substrate. The plurality of surface area regions can be separated by any suitable distance. For example, each of the plurality of surface area regions coupled to the sensing component can be separated by a distance ranging from 0.1 mm to 100 m, such as 0.5 mm to 5 mm, or 0.1 m to 10 m. In one exemplary embodiment, members of a plurality of sensing components were separated by a distance of 50 nm.

In some embodiments, the sensing device can be made by coupling a substrate with one or more sensing components. In such embodiments, the substrate and the one or more sensing components can be physically and/or chemically coupled to provide the sensing device. For example, the sensing component can be physically coupled to the substrate by a coupling component, such as an adhesive. In some embodiments, the substrate and the sensing component can be chemically coupled, such as through ionic and/or covalent bonds formed between the sensing component and the substrate. In particular disclosed embodiments, the disclosed sensing devices exhibit superior bonding between the substrate and sensing component as evidenced by the lack of peel-off or shedding of the sensing component.

The substrate can be pretreated prior to coupling with the sensing component. In some embodiments, pretreatment can comprise exposing the substrate to one or more chemical reagents capable of facilitating chemical coupling to the sensing component. For example, functional groups of the substrate can be exposed or modified so as to promote chemical coupling with functional groups present in the ligands of the MOF material, the metal component of the MOF material, the plasmonic nanomaterials, or a combination thereof. In some embodiments, the substrate can be modified with a chemical reagent such that a layer of the chemical reagent becomes associated with the substrate and can thereby promote chemical coupling of the sensing component.

In an exemplary embodiment, an optical fiber comprising a polymer coating was pretreated with a variety of chemical reagents to produce a sensing device. The polymer coating of the optical fiber was removed chemically and then chemically etched using a buffered oxide etchant or hydrofluoric acid to expose the core. In some exemplary embodiments, a portion of the core can be etched away so as to increase the evanescent field and detectable species. For example, in one exemplary embodiment, the F-doped silica cladding of 25 µm in thickness was etched away to expose the core followed by an additional ~25 µm of etching to reduce the exposed core diameter from 100 µm to 75 µm. Once the core was exposed, the fiber was cleaned and then treated using an $O_2$ plasma treatment to provide hydroxyl groups to which the MOF material could bind.

In yet another exemplary embodiment, the sensing component was deposited onto a solid sapphire substrate. In this embodiment, a combined sensing component was deposited by first spin-coating the sapphire substrate with a solution of a plasmonic nanomaterial. The substrate and plasmonic nanomaterial was then exposed to an $O_2$ plasma treatment, followed by LBL growth of an MOF material, as described above.

IV. Methods of Using Sensor Devices

The sensor devices disclosed herein can be used to detect, qualify, and quantify detectable species in a variety of environments. In some embodiments, the sensor devices can be used to determine the presence of a detectable species. In yet additional embodiments, the sensor devices can be used to store detectable species. In some embodiments, the sensor devices can be used to detect or determine the presence of detectable species in air or liquid. The sensor devices disclosed herein are able to detect gases, organic compounds, or combinations thereof. In some embodiments, the sensor devices can be used to detect and identify different gas species, volatile organic compounds, or combinations thereof. Exemplary detectable species include, but are not limited to, $CO_2$, $SF_6$, water vapor, NO, $CH_4$, $C_2H_4$, $NH_4$, PhMe, $C_6H_6$, and the like. The sensor devices are also capable of distinguishing between different gas species and also quantifying the amount of a particular gas species that is detected.

The sensing components of the disclosed sensor devices can be chosen to selectively detect or determine the presence of particular detectable species. In some embodiments, the particular MOF material used in a sensor device can be selected to specifically absorb and/or adsorb a particular detectable species, such as a particular gas or organic compound. For example, the pore size of the MOF material can be modified based on the type of metal component or ligand component used. The pore size can be enlarged so as to better absorb larger detectable molecules, or it can be decreased so as to detect only detectable molecules of a particular size and exclude larger detectable molecules. In such embodiments, the pores are "internal pores" existing within the MOF material (or the combination of the MOF material and the plasmonic nanomaterials) and that result from the crystalline structure of the MOF material (with or without the plasmonic nanomaterials). Such "internal pores" are distinct from pores existing on the surface of the MOF material (referred to as "external pores") which are merely physical deformities formed by external forces as opposed to the crystalline nature of the MOF material. In yet additional embodiments, the plasmonic nanomaterial used in a sensor device can be modified to provide different plasmonic resonant wavelengths and therefore enhance detectable species absorption. For example, the size of the plasmonic nanomaterial can be enlarged or reduced to tune the plasmonic resonant wavelength. For example, nanoparticle core size can be enlarged or decreased, or nanowire length can be increased or decreased. In yet other embodiments using nanomaterial arrays, the period of the array can be changed to modify the plasmonic resonant wavelength.

In particular disclosed embodiments, the sensor devices are capable of producing detection limits suitable for use in detecting various concentrations of the detectable species. In some embodiments, the sensor devices are capable of detection limits ranging from several hundred ppm to several hundred ppb. In some embodiments, the sensor devices can achieve detection limits ranging from 100 ppm to 700 ppm, such as 100 ppm to 600 ppm, or 100 ppm to 500 ppm. In additional embodiments, the sensor devices can achieve detection limits ranging from 0.1 ppb to 10,000 ppb, such as 0.1 ppb to 10 ppb, or 100 ppb to 1000 ppb. In an exemplary embodiment, a sensor device embodiment was able to detect 500 ppm of a detectable species. The detection limit can further be improved by varying the type of substrate used. For example, in some embodiments, an improved detection limit can be achieved using a single-mode optical fiber instead of a multi-mode fiber. The detection limit of the sensor device can be determined using methods known to those of ordinary skill in the art, such as by measuring changes in optical transmission power as a function of detectable species concentration.

The sensor devices disclosed herein also exhibit efficient response times for determining the presence of detectable species. In some embodiments, response time is measured as the time it takes to register a certain percentage of the total response produced by interaction between the sensing component and the detectable species. Solely by way of example, in some embodiments, a response time can be determined as the amount of time needed to register 75% of a total response due to the presence of a detectable species. In some embodiments, response times can range from seconds to minutes, with some embodiments exhibiting response times of less than 60 seconds. In some embodiments, the response times can range from 0.1 seconds to 100 seconds, such as 0.1 seconds to 1 seconds, or 10 seconds to 50 seconds. In some exemplary embodiments, a response time of 15 seconds and 40 seconds was observed.

In some embodiments, the sensor devices disclosed herein can be used to form sensing networks. Such sensing networks can comprise a plurality of the sensor devices disclosed herein and can therefore be used to determine the presence of, detect, and/or quantify detectable species in large-scale applications. The plurality of sensor devices can be coupled using any suitable coupling component. One or more light sources can be used in such networks. In some embodiments, a remote sensing station can be used to gather data obtained from the plurality of sensor devices.

The sensor devices and/or sensor device networks described above can be used to monitor greenhouse gas emissions, or as gas sensors in food storage. In yet other embodiments, the sensor devices can be used to detect gases produced in gas lines, engines, pipes, and/or any gas leaks produced in such structures. The disclosed sensor devices are also suitable for use in monitoring hazardous gases or other products produced during use of explosives, fertilizers, and the like. In an exemplary embodiment, a method of determining the presence of a detectable species can comprise exposing a sample to a sensor device or sensor device network as described herein and analyzing an optical absorption signal obtained from absorption of the detectable species by the sensor device. In some embodiments, the optical absorption signal can be analyzed or measured by determining the change of transmitted optical power from the sensor device in the presence of the sample and when the sample is not present.

V. Examples

Materials

Indium(III) acetate ($In(Ac)_3$, 99.99%) and copper nitrate hexahydrate ($Cu(NO_3)_2 \cdot 6H_2O$, 98%) were purchased from Alfa Aesar. Tin(II) 2-ethylhexanoate (95%), copper acetate ($Cu(Ac)_2$, 98%), benzene-1,3,5-tricarboxylic acid (BTC, 95%), oleylamine (OLA, >70%), 1-octadecene (ODE, 90%), and 2-ethylhexanoic acid (99%) were delivered from Sigma-Aldrich. Ethyl acetate (99.9%) from Fisher Scientific, n-hexane (95%) from J.T. Baker, anhydrous tetrachloroethylene (TCE, 99%) from Cole-Parmer, ACS grade of ethanol (>99.5%) from Macron chemicals were used for solvents. All chemicals were used as purchased without further purification. Sapphire as substrates were purchased from Precision Micro-Optics with 430 μm thickness.

Characterizations:

X-ray diffraction (XRD) patterns were obtained using a Rigaku Ultima IV Diffractometer, operating at 40 kV and 40 mA with Cu kα radiation (0.154 nm) in the 2 scan range from 5 to 30 with a step size of 0.01. Field emission-scanning electron microscope (FE-SEM) analysis was conducted with an FEI Quanta 600 and FEI Nova NanoSEM 230 using 10 kV accelerating voltage. In some embodiments, a thin gold/palladium layer was coated on the samples to increase its electrical conductivity. The gas sensing properties were measured with a Thermo Scientific Nicolet 6700 Fourier transform infrared (FT-IR) spectrometer. High resolution transmission electron microscopy (HR-TEM) images were obtained using FEI Titan 80-300 operating at 300 kV. X-ray photoelectron spectroscopy (XPS) was carried out with a PHI 5600ci instrument using a monochromatized Al Kα X-ray source (1486.6 eV). The binding energy was calibrated using the C is signal located at 285.0 eV. Samples were lightly sputtered (~30 sec) to remove the very-top surface contamination. $O_2$ plasma system was performed using Harrick Plasma, operating at 50 W for 20 min.

MOF material optical properties were measured by ellipsometry. About 130 nm MOF was grown on the silicon (Si) substrate with $SiO_2$ layer to form high refractive index (RI) contrast layers. Experimental data shows that the real part of the refractive index of MOF at NIR region is about 1.3 and the imaginary part is negligible as shown in FIG. 53.

Example 1

In this example, an evanescent field NIR fiber-optic sensor was fabricated by growing nanoporous MOF materials on the core surface of a multimode fiber (MMF). First, standard buffered oxide etchant (BOE) was used to etch away the cladding of a fluorine-doped silica cladded/silica core MMF (Thorlabs AFS 105/125Y). The length of the etched region was about 8 cm. Prior to the etching process, the MMF polymer coating layer was removed by chemical stripping over a slightly longer length of about 10 cm. To increase the interaction between the evanescent field and the surrounding gas molecules and thereby enhance the sensitivity, the 125 μm core and cladding of the MMF was etched to approximately 75 μm with the core fully exposed. Second, the etched fiber was cleaned thoroughly by acetone, isopropanol and deionized water respectively, followed by $O_2$ plasma treatment (50 w) for 20 minutes. Finally, a thin layer of MOF was grown on the surface of the etched core by stepwise layer-by-layer (LBL) method. Briefly, the fiber was first immersed into a 300 mL ethanol solution which contains 10 mM metal precursor $Cu(Ac)_2$ for 20 minutes. Subsequently, the MMF was immersed into another 300 mL ethanol solution which contained 1 mM organic ligand benzene-1,3,5-tricarboxylate (BTC) for 40 minutes. Between each step, the fiber was rinsed with ethanol to remove the unreacted precursor ions or molecules to ensure the uniform growth and then dried at room temperature for 10 minutes. Optical microscopy images of the MMF before and after growing MOF are shown in FIGS. 2 and 3, respectively. The crystal clear silica core of the MMF was deposited with MOF with some light blue color due to the copper ions. The scanning electron microscopy (SEM) images of the MOF-coated MMF are shown in FIGS. 4 and 5. The cross sectional view in FIG. 4 indicates that the thickness of the MOF film is around 100 nm, and the top view with a tilted perspective angle in FIG. 5 shows that the MOF film consists of many small crystals with average size less than 1 μm. In addition, no peel-off of the MOF film from the MMF was observed, which indicates good bonding between these two materials.

Figure 20:
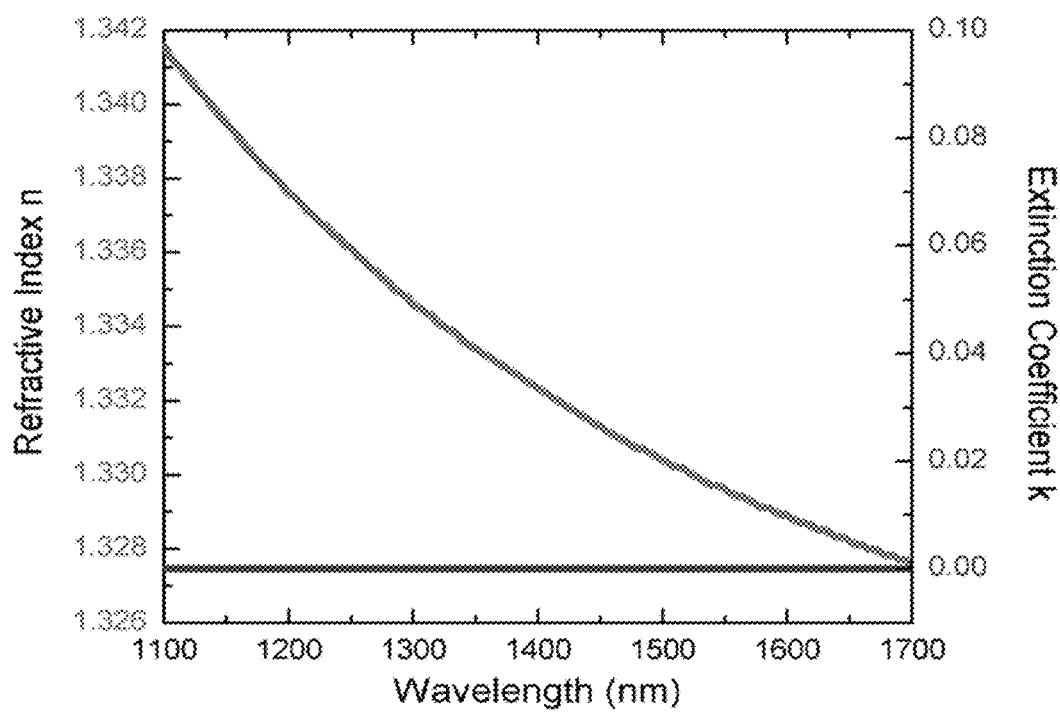
FIG. 20 is a graph of refractive index as a function of wavelength, providing refractive indices of an exemplary MOF material as measured by ellipsometry
Figure 21:
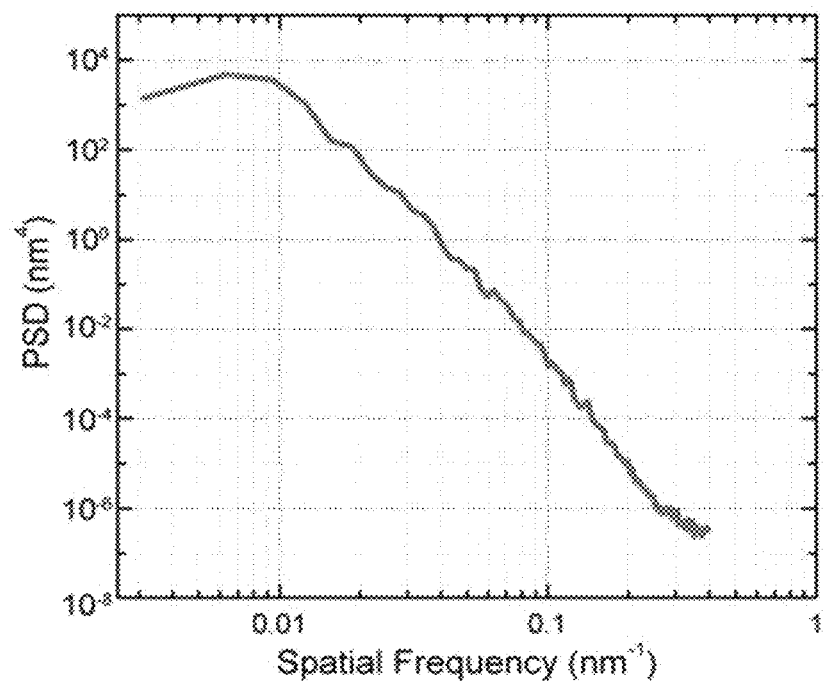
FIG. 21 is a fast Fourier transform graph of surface profile in a spatial domain.
Figure 22:
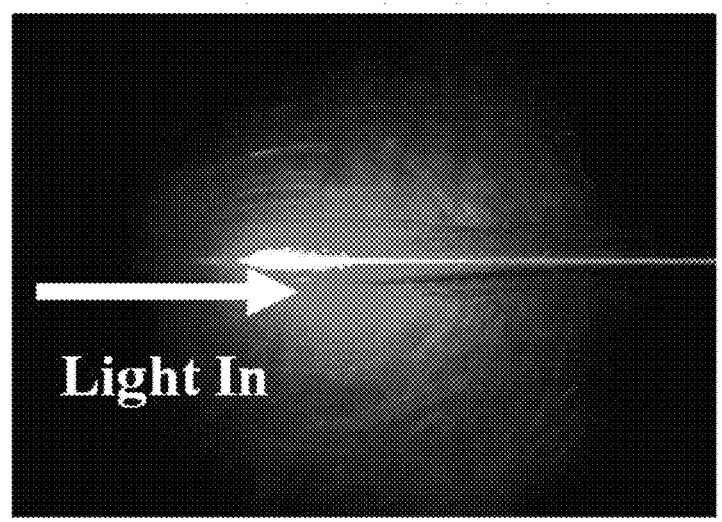
FIG. 22 is an optical scattering image of an MOF-coated fiber-optic sensor illuminated by a 635 nm red laser.

To measure the optical properties of MOF in the NIR wavelength range, a 100 nm thick MOF film was grown on a silicon wafer with 10 nm silicon oxide top layer. The refractive indices of the MOF film were measured and modeled using ellipsometry as shown in FIG. 20. The real part of the refractive index of MOF is 1.33 at 1.57 μm wavelength with a small dispersion from 1.1 to 1.7 μm. The imaginary part of the refractive index is negligible, which means that there is no material absorption in the NIR wavelength range. The refractive index of MOF is less than that of the MMF core (1.45) but greater than that of air; therefore, light can still propagate inside the MMF core, while the evanescent field will also be enhanced compared with air cladding. In some examples, optical loss of the fiber-optic gas sensors was caused by the surface roughness of the MOF crystals. Quantitative measurement of the fiber-optic sensor surface profile was conducted by atomic force microscopy (AFM) as shown in FIG. 6. The AFM surface profile corresponds very well with the SEM image in FIG. 4, with clear images of the small MOF crystals. The root mean square of the surface profile was 64.1 nm. Since the optical scattering can depend on the spatial frequency of the surface profile, post-measurement analysis using fast Fourier transform (FFT) was executed and the results are shown in FIG. 21. In the AFM image (FIG. 6), the scanning area was 2 μm×2 μm with 8 nm spatial resolution. The plotted spatial frequencies from 0.003 $nm^{-1}$ to 0.4 $nm^{-1}$ exhibited a peak power spectral density (PSD) at 0.006 $nm^{-1}$, which corresponds to the average MOF crystal size. Surface roughness with such spatial frequencies is comparable with the NIR wavelength in the fiber and can cause significant amount of optical scattering. The optical image of the MOF-coated MMF illuminated by a 635 nm semiconductor laser in FIG. 22 confirms the strong optical scattering. Broadband NIR light (1.5-1.6 μm) from an amplified spontaneous emission (ASE) light source was also coupled into the fiber-optic sensor. The total loss for the MMF without MOF was 6.8 dB. After being coated with MOF, the loss increased to 15.8 dB.

Example 2

In this example, a $CO_2$ sensing device set-up was examined. An exemplary set-up is illustrated in FIG. 17. A tunable semiconductor laser diode (HP 8168) with a standard single mode (SMF28) fiber pigtail was used as the light source. The output light was first split by a 1×2 10:90 coupler. Ten percent of the light was coupled into a power meter (Thorlabs, Inc. PM20) as the reference, and the other 90% was coupled into the fiber-optic sensor by a buffered fiber adapter (FIS F18294). The sensor was placed inside a gas cell, which was connected to $CO_2$ and Ar gas tanks. The transmitted light through the sensor was directly coupled to another power meter (Thorlabs, Inc. S122C), and the data was collected by a personal computer through a USB power and energy meter interface (Thorlabs, Inc. PM100USB). Gas flows were controlled by two mass flow controllers (MFC) (Aalborg, GFC 17) with 0-20 ml/min flow range. Different $CO_2$ concentrations were achieved by varying the mixing ratio of $CO_2$ and Argon (Ar) flows.

Figure 23:
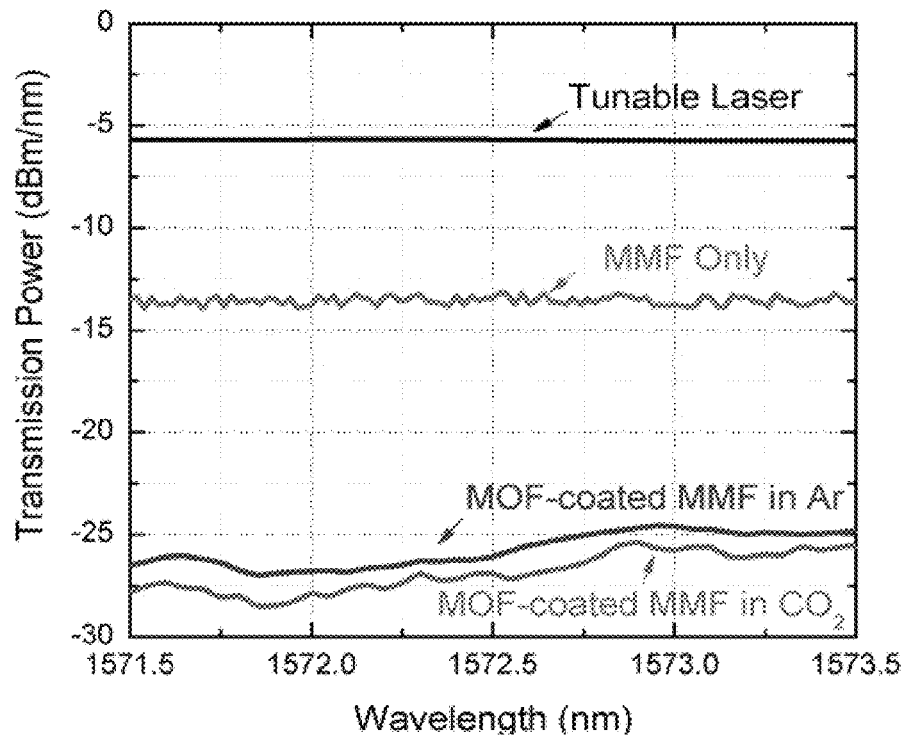
FIG. 23 provides optical transmission spectra of a tunable laser, optical fiber, and MOF-coated optical fiber in (Ar and in $CO_2$).

The gas cell was first purged by ultra-pure Ar for 2 hours to remove water vapor inside the MOF. Then, the gas flow was switched from pure Ar to $CO_2$ with a flow rate of 5 sccm for 5 minutes. The wavelength of the tunable laser was continuously scanned from 1571.5 nm to 1583.5 nm with 0.02 nm resolution. The optical transmission spectra of the tunable laser, MMF fiber only, MOF-coated MMF fiber with pure Ar and with pure $CO_2$ were plotted in FIG. 23. Compared with the tunable laser, the MMF without MOF had 8 dB optical insertion loss due the optical coupling at the fiber connectors and the optical scattering caused by surface roughness at the sensing region. Also, the spectrum was no longer flat and smooth due to the modal noise of MMF. After coated with MOF and purged with Ar, the optical loss further increased to 21 dB due to extra optical scattering by MOF. When the gas flow was switched to pure $CO_2$, the optical transmission spectra dropped around 1 dB due to the $CO_2$ absorption. As a comparison, if the MMF is not coated with MOF, switching Ar to $CO_2$ will not induce any observable change of the optical transmission since the fiber is not long enough to induce detectable NIR absorption.

Figure 24:
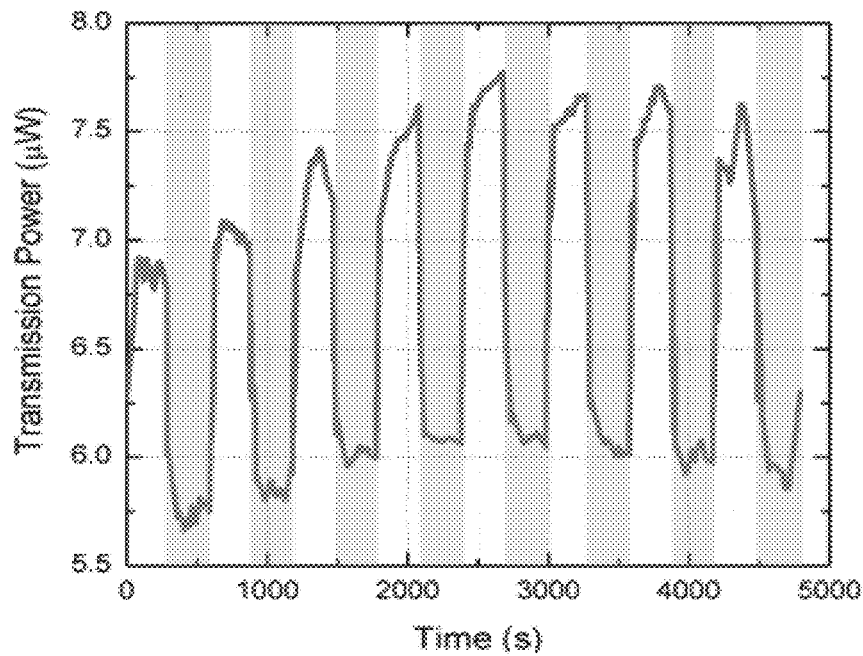
FIG. 24 is a graph of transmission power as a function of time illustrating a real-time response of an MOF-coated fiber-optic sensor to alternating Ar and $CO_2$ flows at 1572.5 nm.
Figure 25:
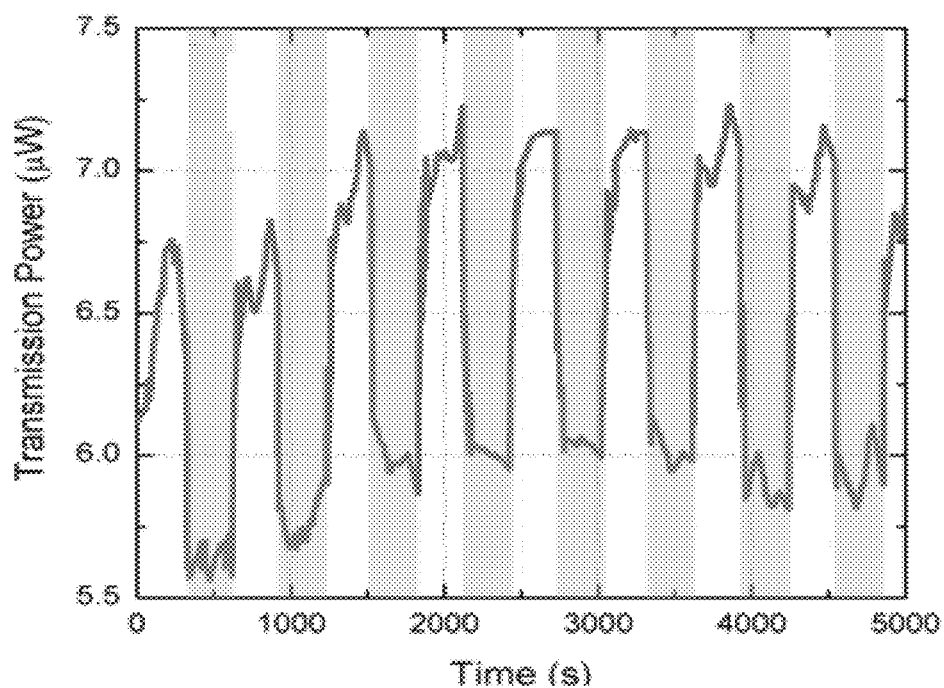
FIG. 25 is a graph of transmission power as a function of time illustrating a real-time response of an MOF-coated fiber-optic sensor to alternating Ar and $CO_2$ flows at 1500 nm.
Figure 26:
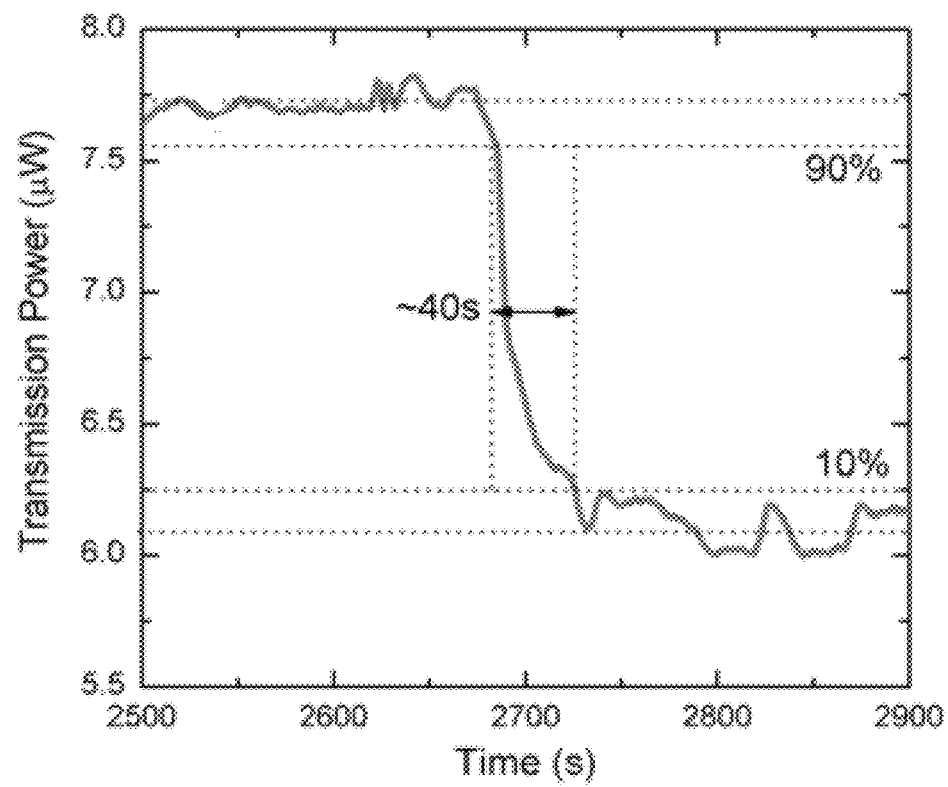
FIG. 26 is a graph of transmission power as a function of time illustrating response time of an MOF-coated fiber-optic sensor for absorbing $CO_2$.
Figure 27:
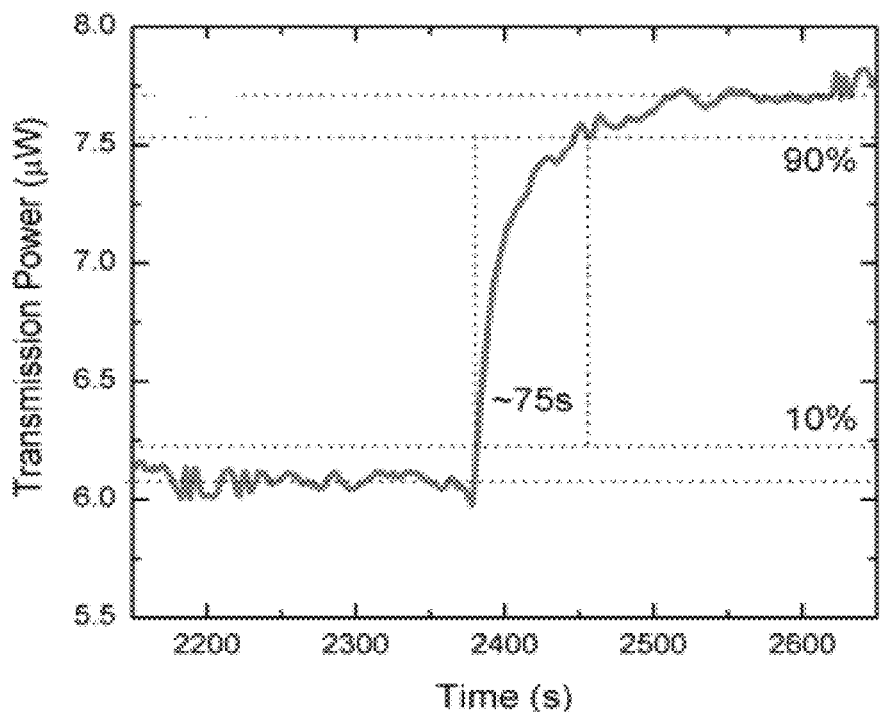
FIG. 27 is a graph of transmission power as a function of time illustrating response time of an MOF-coated fiber-optic sensor for desorbing $CO_2$.

To further determine the dynamic response, real-time data of the fiber-optic sensor was measured. The wavelength of the tunable laser was fixed at 1572.5 nm. Then, pure Ar and $CO_2$ gas flows were switched alternately every 5 minutes. In FIG. 24, the grey regions and white regions represent the time slots when $CO_2$ and Ar flows, respectively. The average transmission power difference between flowing Ar and $CO_2$ was 1.6 μW. As a comparison, the absorption measurement was repeated at 1500 nm in FIG. 25 with average absorption around 1.1 μW. This observation indicates that the absorption spectrum of $CO_2$ in MOF might be different from the gas in free space, which should have orders of magnitude higher absorption rate in the 1572.nm absorption lines than in 1500 nm. Interestingly, when a 635 nm laser diode was used as the light source, no meaningful absorption was observed. These results confirmed that the optical absorption at 1572.5 nm and 1500 nm were caused by the $CO_2$ absorption in MOF, which may have different spectral widths than the a few narrow lines as predicted. The response time of the sensor was measured for both the absorption and desorption process as shown in FIGS. 26 and 27. The absorption time (from 90% to 10%) was approximately 40 seconds and the desorption time (from 10% to 90%) was approximately 75 seconds. In some examples, results for the overall response times included purging the gas cell with volume of 7 $cm^3$. The MOF layer was only 100 nm thick, and the absorption time and desorption time for $CO_2$ was therefore likely to be negligible compared with the time to purge the gas cell.

Example 3

Figure 28:
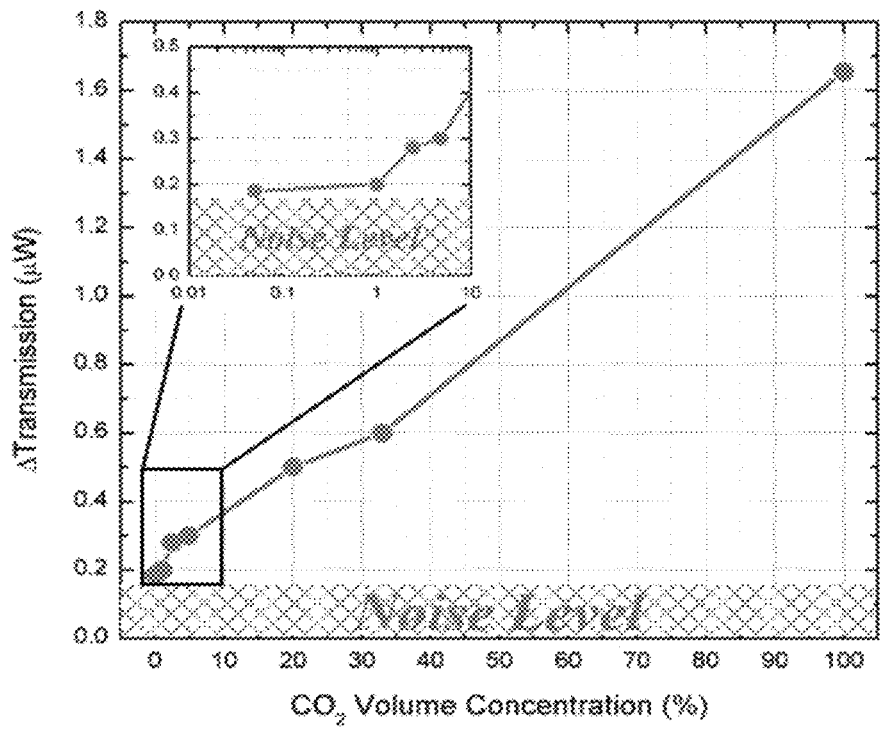
FIG. 28 is a graph of ΔTransmission as a function of $CO_2$ volume concentration in Ar, with an inset providing a magnified plot for low concentration (log scale).

In this example, the detection limit of the fiber-optic sensor was tested by measuring the change of the transmitted optical power (ΔTransmission) as a function of $CO_2$ concentration. Different concentrations of $CO_2$ were obtained by mixing pure Ar and $CO_2$ at various flow rates. From the plot of FIG. 28, the relation between ΔTransmission and the $CO_2$ concentration can be observed. The slope at higher concentration (>5%) is smaller than that at lower $CO_2$ concentration. Without being limited to a single theory of operation, it is currently believed that this results because higher concentration $CO_2$ will saturate the nanoporous MOF film. The inset figure shows zoomed-in plot of ΔTransmission vs. $CO_2$ volume concentration in log-scale. The lowest $CO_2$ concentration that was measured was 500 ppm. In some examples, the detection limit can be influenced by the noise of the MMF, which can cause signal fluctuation that is comparable with low concentration $CO_2$ absorption. A single-mode optical fiber coated with MOF can be used to further improve the detection limit. The examples presented above demonstrate the utility of ultra-short NIR fiber-optic gas sensors based on MOF-coated MMF for $CO_2$ sensing. Compared with conventional evanescent field fiber-optic gas sensors, the sensing length was reduced to only 8 cm by selective concentration of $CO_2$ by the MOF film, which was deposited at the surface of the core of the MMF. A detection limit of 500 ppm was achieved in some examples, and the overall real-time response was found to be only 40 seconds for absorption and 75 seconds for desorption in a gas cell. These results further establish the shortest NIR fiber-optic sensor for $CO_2$ detection at 1.57 μm wavelength. Such ultra-short fiber-optic gas sensors with rapid response time can be used for greenhouse gas detection and environmental protection.

Example 4

Sn-Doped Indium Oxide Nanocrystals (ITO NCs) Synthesis

ITO NCs were synthesized by using a hot-injection method. A solution consisting of $In(Ac)_3$ (0.96-1.20 mmol), Tin(II) 2-ethylhexanoate (0.01-0.24 mmol), 2-ethylhexanoic acid (3.6 mmol), and octadecene (10 mL) in three-neck flask was stirred under vacuum at 80° C. for 30 min, then purged with Ar gas at 150° C. for 60 min while stirring. In the meantime, a solution containing oleylamine (10 mmol) and octadecene (5 mL) was purged with Ar gas at 100° C. for 60 min, and then was injected into a three-neck flask at 240° C. The reaction mixture was held at 290° C. for 2 hours. The reaction mixture was allowed to cool and 10 mL of ethyl acetate was added to precipitate the NCs followed by centrifuging at 6000 rpm for 10 minutes. The supernatant was discarded, and 5 mL of toluene and 5 mL of ethyl acetate were added to flocculate the NCs followed by an additional centrifuging at 6000 rpm for 10 minutes. The supernatant was decanted, and the final product was re-dispersed in non-polar solvent such as tetrachloroethylene, hexane, and toluene for further characterization.

ITO Thin Films:

A spin-coating method was used to fabricate ITO thin films. Sapphire as substrates were cleaned via sonication in a three step process: 15 minutes deionized water, 15 minutes acetone, 15 minutes isopropanol. Three rinses were performed between each sonication step. A total 100 µL of the ITO NCs dispersion in hexane were spin-coat onto sapphire substrate (2.5 cm×2.5 cm) at 5000 rpm for 30 seconds. Finally, the ITO NCs-coated sapphire substrate was treated by $O_2$ plasma at 50 W for 20 minutes.

Cu-BTC Films and Bulk Powder:

A stepwise layer-by-layer (LBL) method was used to grow the Cu-BTC MOF thin films onto the ITO-coated sapphire substrate. In a typical method, the ITO-coated sapphire substrate after $O_2$ plasma treatment was immersed in a 2 mM of the metal precursor $(Cu(Ac)_2)$ 60 mL ethanol solution for 20 minutes. Subsequently, the ITO-coated sapphire substrate was immersed in a 0.2 mM solution of the organic ligand (BTC) in 60 mL ethanol solution for 40 minutes. Between each step the substrates were rinsed with ethanol to remove unreacted precursor ions or molecules and to ensure uniform film growth and dried in a $N_2$ stream. Powder-typed bulk Cu-BTC synthesized via a typical solvothermal method in the batch reactor was also prepared. A solution of $Cu(NO_3)_2.6H_2O$ (3.6 mmol) in 60 mL of ethanol and BTC (8.1 mmol) in 60 mL of ethanol were both stirred for 10 minutes in a 250 mL beaker, separately. A 50/50 mixture of $Cu(NO_3)_2$ and BTC solution was stirred for 10 minutes, then was placed in a Teflon autoclave. The sealed autoclave was heated to 120° C., held for 18 hours in a convective oven, and cooled to room temperature naturally. The collected reaction products were washed with ethanol 3 times and were dried under vacuum for 24 hours at 70° C.

Sensor Performances:

Flow gas-cell for the NIR absorption sensors using plasmonic-enhanced nano-composite MOF//ITO/Sapphire is designed (FIG. 17). Before measure transmittance (% T), the gas-cell was purged with ultra-high purity Ar gas for 24 hours at room temperature, which is used for baseline in the spectrum. A high (100%) and low (0.1% in $N_2$) concentration of $CO_2$ gas was then passed through the flow-cell at atmospheric pressure. The flow rates of the gases were controlled at 10 mL min$^{-1}$ using mass-flow-controllers.

Figure 29:
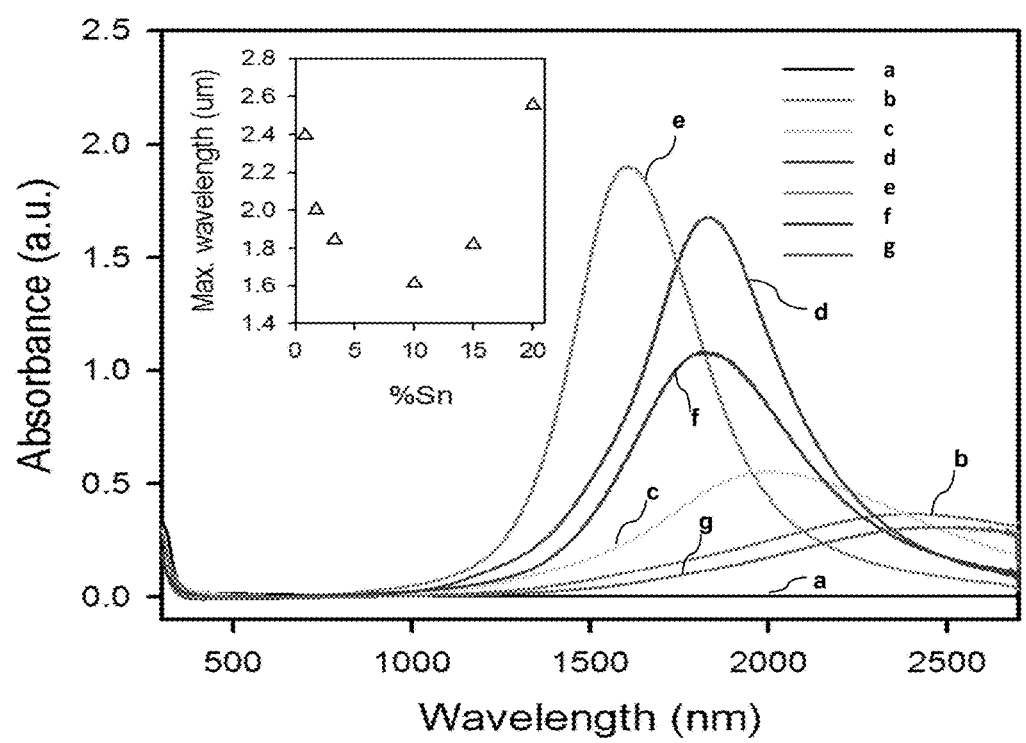
FIG. 29 is a combined absorption spectrum illustrating absorption spectra of synthesized ITO nanocrystals dispersed in TCE, with an inset illustrating a dependence of the SPR peaks of ITO nanocrystals on the doped % Sn.

In this example, plasmonic ITO NCs were synthesized using embodiments of a hot-injection method described herein. The exemplary method used in this example is discussed above. These plasmonic ITO nanocrystals were deposited on substrates via spin-coating, followed by growth of the MOF using the room temperature layer-by-layer (LBL) approach. FIG. 29 shows the absorption spectra of the ITO NCs dispersed in tetrachloroethylene (TCE) with varying Sn percentages (line a=0% Sn; line b=0.8% Sn; line c=1.7% Sn; line d=3.3% Sn; line e=10% Sn; line f=15% Sn; and line g=20% Sn). No surface plasmon resonance (SPR) was observed in the un-doped sample ($In_2O_3$ NCs), while the absorption peak did appear with the ITO NCs. Without being limited to a single theory of operation, it is currently believed that this peak results from the SPR absorption. It is also currently believed that this property supports the theory that the Sn occupies substitutional sites creating free-electrons in the $In_2O_3$ structure. The SPR peak gradually blue-shifted from 2400 to 1610 nm when the Sn precursor increased from 0.8% Sn to 10% Sn. Further increasing of Sn percentage led to a gradual red shift of the SPR peak from 1810 to 2550 nm as the Sn percentage increased from 15 to 20% (insert of FIG. 29). This result indicates that 10% Sn-doped ITO NCs can exhibit strong plasmon absorption, which likely results from the corresponding highest free-electron density. Transmission electron microscopy (TEM) imaging (FIG. 30) was used to establish that ITO NCs were highly mono-dispersed and high-resolution TEM (HRTEM, insert of FIG. 30) revealed single crystals with a lattice fringe distance of 0.292 nm, illustrative of the crystal lattice spacing of the (222) planes of ITO.

Figure 34:
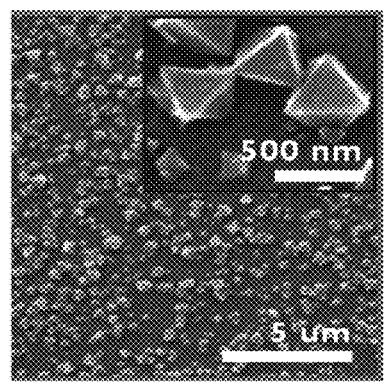
FIG. 34 is an SEM image of an exemplary combined sensing material after 10 cycles of deposition, with an inset showing an individual MOF microcrystal with a size of ~300 nm.
Figure 35:
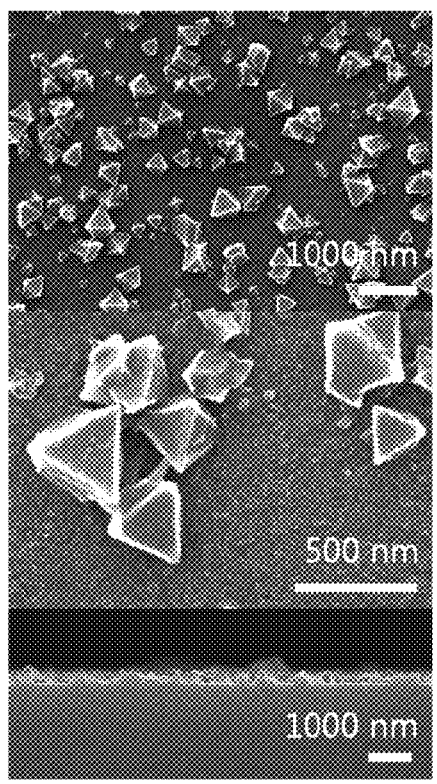
FIG. 35 is a combined SEM image illustrating a top view and cross-sectional view of a combined sensing component grown using 10 growth cycles.
Figure 36:
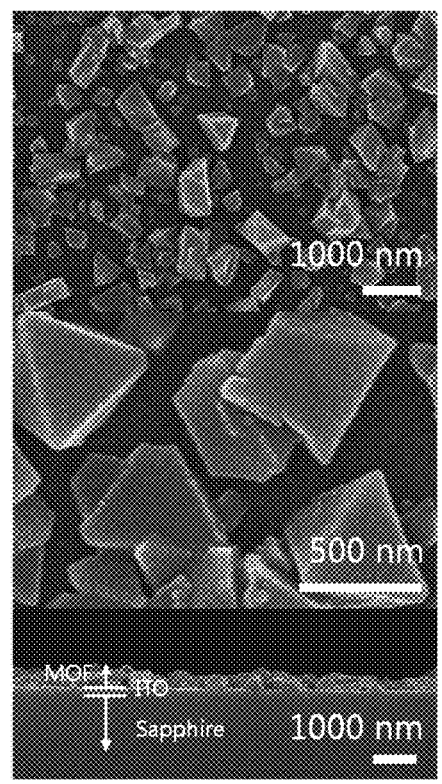
FIG. 36 is a combined SEM image illustrating a top view and cross-sectional view of a combined sensing component grown using 30 growth cycles.
Figure 37:
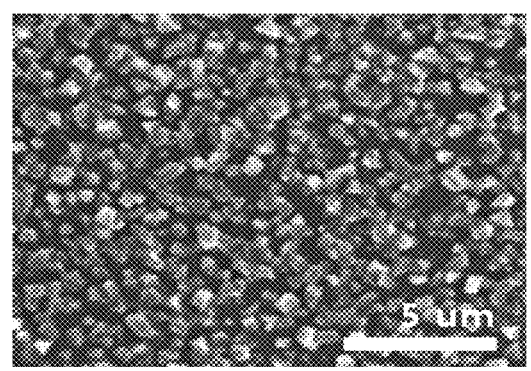
FIG. 37 is an SEM image illustrating a combined sensing component grown using 30 cycles of a layer-by-layer (LBL) method as described herein.

Freshly prepared ITO NCs were deposited onto a sapphire substrate by spin coating from a hexane solution, followed by $O_2$ plasma treatment and then MOF film growth using the LBL method (FIG. 13). The SEM image in FIG. 31 shows that the individual ITO NCs (10% Sn) were uniformly deposited onto the sapphire substrate by the spin-coating method with a thickness of ~130 nm, which was measured by cross-sectional SEM imaging (FIG. 32). The residual organic compounds left on the surface of the ITO NCs can be removed prior to MOF film growth to prevent the organic compounds from having a deleterious effect on the MOF growth and/or the optical properties of the fabricated sensors. $O_2$ plasma techniques can be used to remove any residual organic compounds (FIG. 33) and to produce hydroxylated surfaces, which can be used to replace the self-assembled monolayer (SAM) commonly used in MOF thin-film growth with a stepwise, LBL method as discussed herein. A Cu-BTC MOF was chosen as an exemplary embodiment for this example given its adsorption capacity for $CO_2$. Cu-BTC MOF of 10 cycles LBL growth on ITO film (MOF10//ITO) surfaces produced crystals with sizes ranging from 150 nm to 300 nm. These crystals were distributed on the surface of the ITO film (FIGS. 34, 35, and 36) with clear triangular-shaped single crystals (insert of FIG. 34), suggesting that in some embodiments, the Cu-BTC particles can grow to the specific orientation on ITO film. Increasing cycles of Cu-BTC MOF growth to 30 cycles LBL growth (MOF30//ITO) increased surface coverage into the continuous film region, as shown in FIG. 37. Without being limited to a single theory of operation, it is currently believed that this result suggests that the Cu-BTC MOF film grows directly on the ITO film after $O_2$ plasma treatment. The thickness of the Cu-BTC film in this example was about 300 nm after 30 cycles of LBL growth (cross-sectional SEM image in FIG. 32). In some examples, uniform thin films with complete surface coverage can be achieved by increasing the number of LBL growth cycles.

Figure 38:
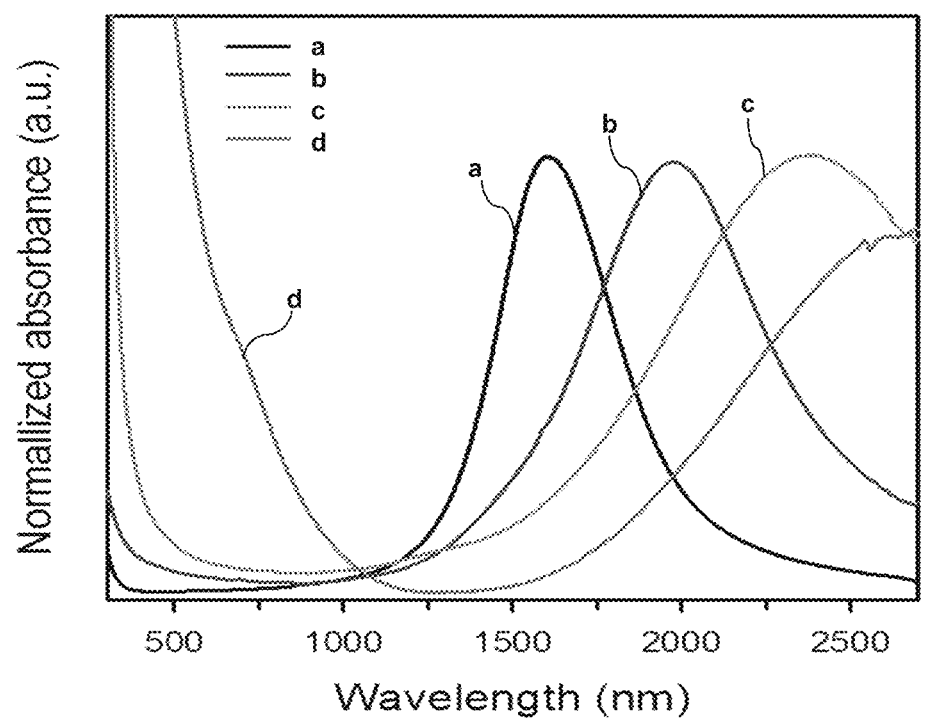
FIG. 38 is a combined UV-Vis-NIR spectrum providing spectra of 10% Sn-doped ITO nanocrystals dispersed in TCE (a), an as-deposited ITO film on sapphire substrate by spin-coat (b), an ITO film on sapphire after $O_2$ plasma treatment (c), and an embodiment wherein 10 cycles of MOF growth on an ITO film was obtained using an LBL method as disclosed herein (d).
Figure 39:
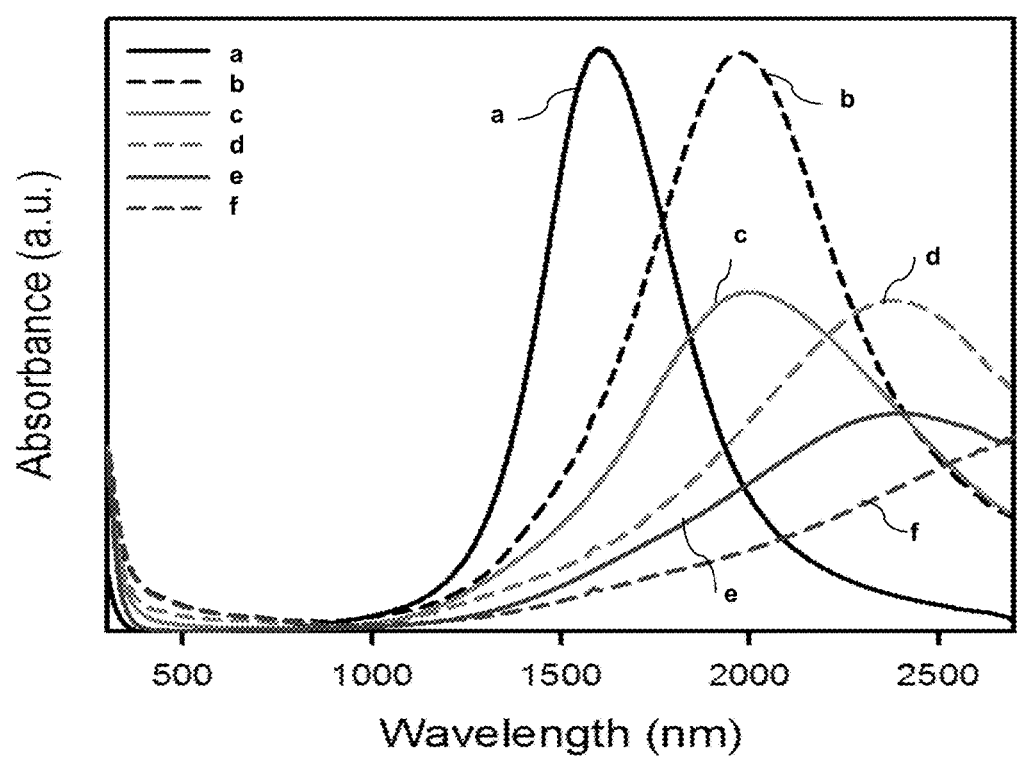
FIG. 39 is a combined UV-Vis-NIR spectrum providing spectra of ITO nanocrystals dispersed in TCE (lines a, c, and e) and as-deposited ITO nanocrystals (lines b, d, and f) on a sapphire substrate by spin-coating.
Figure 40:
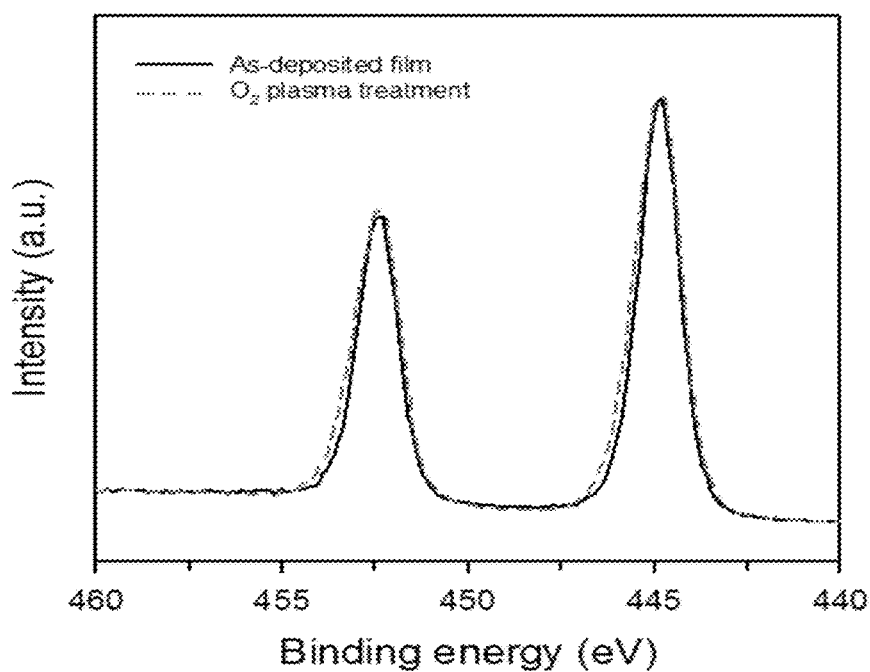
FIG. 40 is an XPS spectrum illustrating results obtained from XPS analysis of the In3d peak in ITO nanocrystals with 10% Sn.
Figure 41:
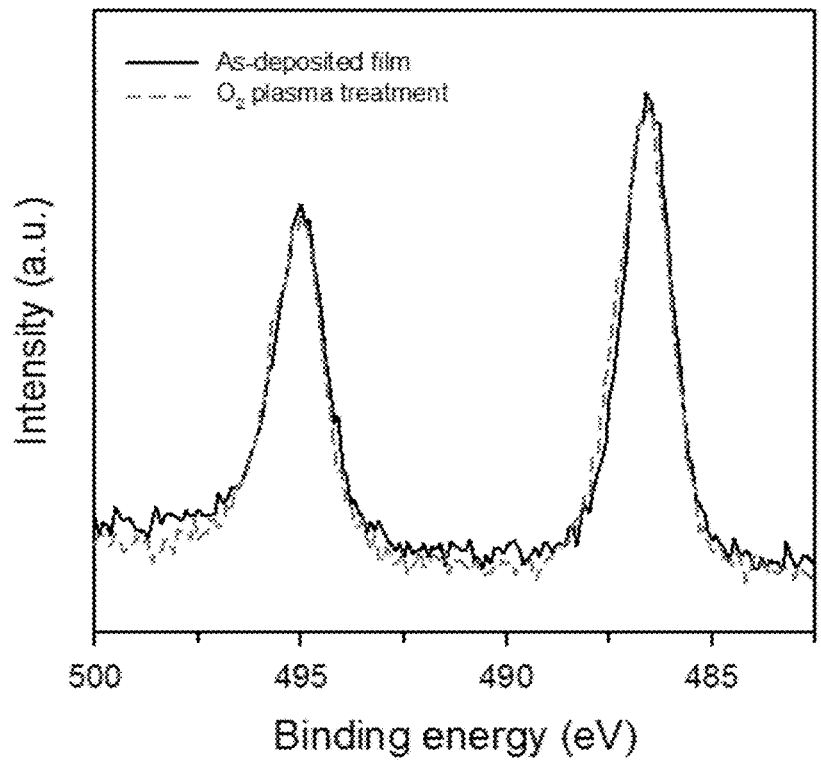
FIG. 41 is an XPS spectrum illustrating results obtained from XPS analysis of the Sn3d peak in ITO nanocrystals with 10% Sn.
Figure 42:
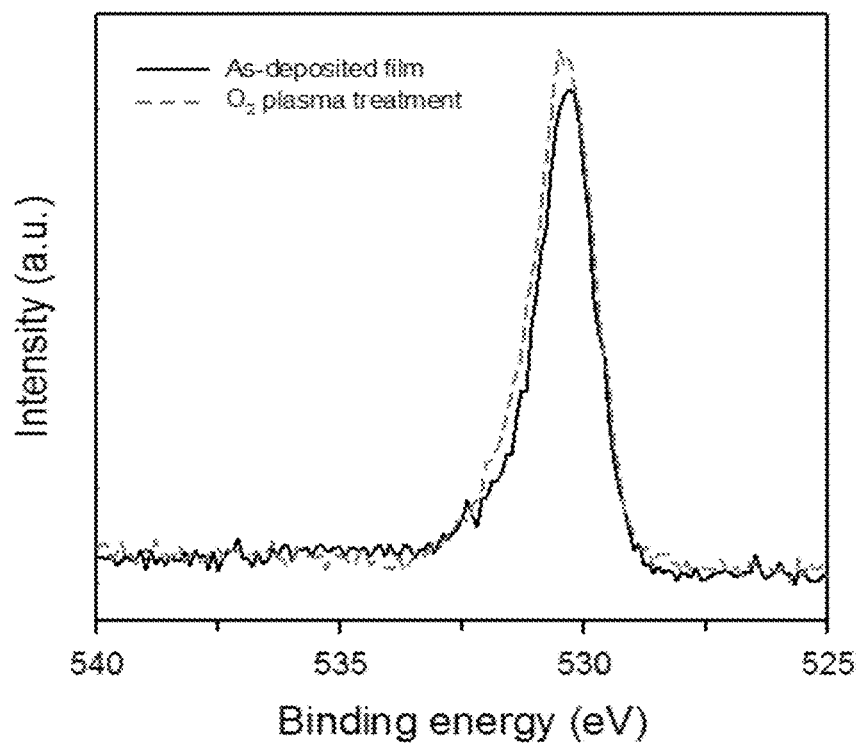
FIG. 42 is an XPS spectrum illustrating results obtained from XPS analysis of the O1S peak in ITO nanocrystals with 10% Sn.

The UV-Vis-NIR absorption spectra of the samples obtained at each stage of film deposition and processing are shown in FIG. 38 (line a=ITO nanocrystals in solution; line b=ITO film as deposited; line c=ITO film after $O_2$ plasma; line d=MOF10//ITO). The absorption peak of as-deposited 10% Sn-doped ITO film shifted to longer wavelength due to an increasing ITO volume fraction from extremely low in the solvent dispersion to the as-deposited film, which was also observed in other samples with different % Sn (FIG. 39, wherein line a=10% Sn in TCE; line b=10% Sn as deposited; line c=1.7% Sn in TCE; line d=1.7% Sn as deposited; line d=0.8% Sn in TCE; and line e=0.8% Sn as deposited). Additionally, the shift of the absorption peak after $O_2$ plasma treatment was observed. XPS was used to determine the change of chemical states of the ITO film due to $O_2$ plasma treatment. The O 1s peak appears primarily as a single peak with slight increase both in relative peak height and in peak broadening towards the higher binding energy side after $O_2$ plasma treatment (FIGS. 40-42). The broadenings were also observed for the In 3d and Sn 3d spectra, although it is more obvious for the In 3d spectra. The increase in relative O 1st peak height of the ITO films after $O_2$ plasma-treating suggests a higher concentration of oxygen (O/In=1.31 vs 1.13 for the as-deposited ITO film), which is expected to impact the free carrier density. Accordingly, it is currently believed that the shift in absorption peak after $O_2$ plasma treatment likely can be attributed to a decrease in free carrier concentration.

Figure 43:
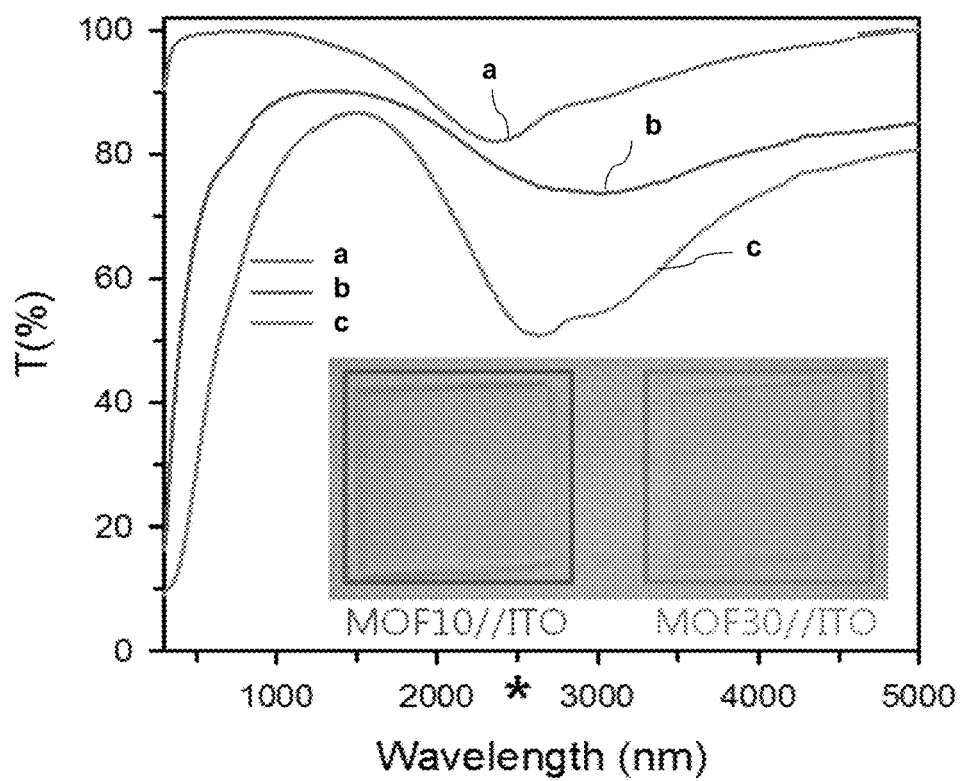
FIG. 43 is a graph of transmittance as a function of wavelength illustrating transmittance observed from sensing component embodiments using 10 cycles (line b) and 30 cycles (line c) LBL growth onto an ITO film (ITO film alone is represented by line a), with an inset showing photoimages of the MOF10//ITO and MOF30//ITO films; the symbol (*) on x-axis indicates the junction point between the two spectra (Vis-NIR and IR).

The MOF10//ITO and MOF30//ITO show an absorption peak located at 700 nm (FIG. 43, wherein line a=ITO film; line b=MOF10//ITO; and line c=MOF30//ITO), which is attributed to the d-d band typical of copper carboxylate complexes, corroborating that the Cu-BTC MOF was produced on the ITO film. The surface plasmon absorption peaks for an ITO NC film appears at 2400 nm and both were broadened and shifted towards a max value of ~2700 nm after Cu-BTC MOF growth on the ITO film, which indicates that the surface plasmon frequencies are sensitive to the surrounding environment. In this example, the overtune vibration frequencies for $CO_2$ molecules appears at 2700 nm and the prepared nanoporous MOF//ITO thin-film in this example exhibited significant overlap with this characteristic band of $CO_2$. This result corroborates the use of this exemplary and like materials for detecting $CO_2$ molecules in the NIR range.

The crystal structures of the samples were identified by XRD and the results are shown in FIG. 44, wherein line a=MOF30//ITO; line b=MOF10//ITO; line c=ITO after $O_2$ plasma treatment; line d=ITO as deposited; and line e=bulk Cu-BTC. Both the as-deposited and $O_2$ plasma-treated ITO film show diffraction peak at $2\theta=30.5°$ and $35.3°$ for (222) and (400) planes, respectively, corresponding to the cubic bixbyite structure of the $In_2O_3$ (JCPDS file 06-0416). After 10 cycles LBL growth of Cu-BTC MOF on ITO film, the new diffraction peak at $2\theta=11.6°$ appeared, corresponding to (222) plane of Cu-BTC. Further increasing the LBL cycles (MOF30//ITO) and the diffraction peaks revealed the presence of a polycrystalline material with preferred orientation along the (111) direction. Hydroxyl functional groups on the ITO film surface may induce MOF growth in a specific crystallographic direction, leading to preferentially oriented films. The decreasing intensity of ITO diffraction peaks indicates increased MOF layer thickness.

To examine the capability for the fabricated NIR absorption sensor, a gas-flow (sensing) cell comprising a bare sapphire, an ITO/sapphire combination and an MOF//ITO/sapphire combination was developed as shown in FIG. 16. Before measuring the transmittance (% T), the designed flow-cell was inserted into the FT-IR chamber filled with pure $N_2$ gas to prevent the absorption of atmospheric $CO_2$. At the same time, the gas-cell was purged with ultra-high purity Ar gas for 24 hours at room temperature, which was used for the baseline in the spectra. A high- (100%) or low-concentration (0.1%) of $CO_2$ gas was then passed through the flow-cell at atmospheric pressure. Typical FT-IR absorption spectra of $CO_2$ gases measured at the high and low concentrations of $CO_2$ are shown in FIG. 45 (top and bottom, respectively). The sensor performance at a high-concentration of $CO_2$ flowing was determined by measuring the difference in % T, which is calculated by (% T of Sapphire)–(% T of ITO/Sapphire or MOF//ITO/Sapphire). As can be seen in FIG. 46 (bottom of left spectra), the difference in % T observed for an ITO film was about 0.8% compared to bare sapphire, indicating that plasmonic ITO NCs enhanced the sensitivity in $CO_2$ sensing. Using a 3-dimensional finite element method simulation with periodic boundary condition, the electromagnetic field distribution of the ITO NCs thin film covered by 90 nm MOF layer was quantitatively estimated by the RF module of COMSOL 4.4 (FIGS. 47A-47C).

The model used in the simulation was constructed according to the SEM image shown in FIG. 31. For the sake of simplicity, it was assumed that the ITO NCs formed a highly packed monolayer on top of sapphire substrate ($n_{sub}$=1.726), which is a hexagonal array as shown in FIG. 47A. The field was calculated at the incident light wavelength of 2700 nm. FIG. 47B and FIG. 47C present the map of simulated electric field intensity on horizontal (XY plane) and vertical (XZ plane) cross-section. E is the local electric field and $E_0$ is the incident electric field. The incident light, excited from the substrate side, is polarized in x-direction and propagates in z-direction. The diameter of ITO NC was set to be 15 nm with 2 nm gap between each nanocrystal, which matches the average value of real synthesized nanocrystals. A 90 nm MOF layer was placed on top of ITO NPs with refractive index $n_{MOF}$=1.3, which was obtained from ellipsometry. The dielectric constant of ITO was obtained from Drude model.

Strong field enhancement mainly occurs in the gaps between ITO NCs, which forms the hotspots. The maximum enhancement factor is about 755 and 762 for horizontal and vertical cross-section, respectively. Since each gap has a hotspot, there will be intense hotspots across the whole array, which contributes to the enhancement of NIR absorption. To compare the average enhancement, the optical field intensity was integrated over the 90 nm thick MOF layer. The results indicate that with the presence of ITO NCs, the average enhancement factor can be about 50. Moreover, if multilayer configuration is considered, the number of hotspots and average enhancement can be further increased.

The MOF30//ITO exhibited a 1.05% difference in % T (FIG. 46, top of right spectra), which likely is due to $CO_2$ readily adsorbing into MOF pores. Moreover, the difference in % T of sapphire and MOF30//ITO samples was about 1.85%. The capability for NIR absorption sensor at low concentrations of $CO_2$ flowing was also determined, with the results being illustrated in FIG. 46 (middle schematic). Increased difference in % T for the absorption band of $CO_2$ was also confirmed when the ITO NCs were coated onto sapphire substrate, indicating that plasmonic ITO thin-films can detect low-concentrations of $CO_2$ (e.g., well below 1000 ppm) in the NIR range. Moreover, the difference in the % T result of the MOF30//ITO film with low concentration of $CO_2$ flowing indicate that this exemplary film can effectively detect $CO_2$ at substantially increased sensitivity in comparison to a simple ITO film. To avoid the possible influence of residual $CO_2$ in MOF pores, all the samples were purged with Ar gas for 72 hours at room temperature and tests were performed on a freshly corrected base-line before measuring % T. For reference, the flow cell designed in this study can be recovered within 60 minutes under the given conditions (FIGS. 48A, 48B, 49A, and 49B). The fabricated MOF//ITO sensor exhibited the potential for applications in NIR gas a sensing.

In this example, a plasmonics-enhanced MOF nanoporous film was developed and its potential for sensing $CO_2$ in the NIR range was demonstrated. This nanocomposite thin film was highly sensitive in NIR absorption as exhibited by effectively pre-concentrating $CO_2$ molecules in MOF pores causing close proximity to the strongly localized optical fields at the plasmonic NCs surface.

Example 5

In this example, an RF module from COMSOL 4.4 was used to numerically design and investigate the plasmonic enhancement for NIR absorption sensing. Four different nano-structures were studied: thin film formed ITO nanoparticles (NPs), hollow bowtie antenna array in gold film, gold nanorod (NR) array, and gold dipole antenna array. Based the simulation results and the consideration of experimental feasibility, three nano-structures were selected as exemplary embodiments for use in device fabrication.

In an exemplary simulation, it was assumed that the NPs had 10 nm diameters, to model chemically synthesized ITO NPs, and that those NPs are closely packed on the sapphire substrate. The results in FIG. 50A show that the plasmonic resonant wavelength varies with the free carrier concentration (line a=$n=5.332\times10^{20}$; line b=$n=6.776\times10^{20}$; line c=$n=8.221\times10^{20}$; line d=$n=9.665\times10^{20}$; line e=$n=11.110\times10^{20}$; line f=$n=12.554\times10^{20}$; line g=$n=13.998\times10^{20}$). Higher free carrier concentrations will blue-shift the resonant wavelength. The absorption of pure $CO_2$ at 2.0 µm and 2.7 µm bands are also simulated by adding the imaginary part of the refractive index of $CO_2$ obtained from HITRAN database. The size of the simulation domain is 1000 nm, which is also the absorption length. The simulation results are shown in FIGS. 50B-50E, with optical field densities illustrated in FIG. 50F. The absorption was ~0.0017% and ~0.09% for 2.0 µm and 2.7 µm bands respectively. However, since transmission spectra of the entire simulation window were monitored, major absorption comes from the 1 µm absorption length. Therefore, the simulated IR absorption enhancement is relatively low. But if multilayer ITO NPs or aggregation in the real experimental samples is considered, the enhancement should be larger.

The second plasmonic nanostructure that was evaluated was a gold nanorod array. In this simulation, the width (200 nm) and thickness (100 nm) of the nanorod was fixed. By varying the length of the nanorod and the period of the array, plasmonic resonant wavelength can be tuned as shown in FIG. 51A (line a=L of 1300 nm, p of 1500 nm; line b=L of 1000 nm, p of 1500 nm; line c=L of 800 nm, p of 1500 nm; line d=L of 700 nm, p of 1500 nm; line e=L of 800 nm, p of 1200 nm). For this structure, the reflection spectra are monitored instead of the transmission. In this way, the absorption will be purely due to the enhanced absorption. Similar to ITO NP thin film simulation, the $CO_2$ absorption was considered as shown in FIGS. 51B-51E. The absorption was ~0.002% and ~0.1% at 2.0 µm and 2.7 µm, respectively. This is due to the larger optical field enhancement as shown is FIG. 51F.

To obtain even larger NIR enhancement, gold dipole antenna array was studied. The width and thickness of the dipole antenna is still fixed as 200 nm and 100 nm respectively. The gap between the two antenna components was 50 nm. By changing the length (L) of the antenna components and the period of the array (p), the plasmonic resonant wavelength can be tuned as shown in FIG. 52A (line a=L of 350 nm, p of 1200 nm; line b=L of 400 nm, p of 1200 nm; line c=L of 450 nm, p of 1200 nm; line d=L of 500 nm, p of 1200 nm; line e=L of 500 nm, p of 1500 nm; line f=L of 540 nm, p of 1500 nm; line g=L of 550 nm, p of 1500 nm; line h=L of 600 nm, p of 1400 nm; and line i=L of 600 nm, p of 1500 nm). FIGS. 52B-52E show the simulation results when $CO_2$ absorption is considered. The absorption was ~0.00225% and ~0.225% at 2.0 µm and 2.7 µm, respectively, which is significantly higher than the gold NR structures due the larger optical field enhancement as shown in FIG. 52F. Besides, the reflection spectrum was also simulated when there is no antenna array. It shows that the absorption is negligible.

In this example, the fiber used as the optical sensor had a 100 µm core and 25 µm cladding. About 25 to 35 µm of the fiber was etched by hydrofluoric acid (HF) to form about 8 to 10 cm long etched area. Then a layer of MOF was grown on the etched fiber by an exemplary LBL method described herein. FIG. 54 shows the SEM images of the optical fiber after growing the MOF.

Also, a gold nanorod (Au NR) array was fabricated by electron beam (Ebeam) lithography. The substrate was first cleaned thoroughly by acetone, IPA and DI water respectively. Then 150-200 nm PMMA was spin coated on to the substrate and prebaked for 1 minute at 80° C. The pattern was written by Ebeam. The parameters used in this example are listed below in Table 1. After ebeam writing, the PMMA was developed by Methyl Isobutyl Ketone (MIBK) and IPA mixed solution at 1:3 ratio for 60 seconds. After being cleaned by DI water and dried by $N_2$ flow, the pattern shown in FIG. 7 was ready for use. 5 nm Cr and 100 nm Au thin film was deposited onto the PMMA by thermal evaporation, respectively. Finally, a lift-off process by acetone with ultrasonic assistance was used to create the metallic patterns.

TABLE 1

| Parameters for Ebeam lithography | | | | |
| --- | --- | --- | --- | --- |
| Beam Current | Area Dose | Magnification | Center-to-center | Line Spacing |
| 16 pA | 400 µC/cm² | 2500 | 0.79 nm | 4.72 nm |

The reflection spectrum of the Au NRs was successfully measured. FIG. 18 shows the measurement setup. The excitation light (white light source) was launched from the top fiber, then passing through a 50/50 beam splitter. About half of the light will be reflected to the left branch and focused by an objective (×40). The reflected light from the sample will be collected and collimated by the same objective. Then passing through the beam splitter again. About half of the light will pass through and coupled into a multimode fiber by the objective (×20). The loss for both top-to-left and left-to-right branch are 3-4 dB. FIG. 55 shows the reflection spectrum obtained by this setup. As it shown, the result is very noisy. The reason is that the power of the white light source at infrared region is very weak which almost reaches to the noise level of the spectrometer. Therefore, another ASE light source having higher power around 2.0 μm wavelength can be used to improve these results.

The MOF material was successfully grown onto the etched optical fiber. The $CO_2$ sensing capability is demonstrated by comparing the light power output with Ar. A tunable laser was used as the light source to launch the light into the fiber. The etched fiber was sealed inside a sensing gas cell as shown in FIG. 56. The output power is monitored directly by a power meter. First, the wavelength from 1571.5 nm to 1573.5 nm was scanned, while Ar or $CO_2$ was flowing. The transmission spectrum for Ar (line a) and $CO_2$ flowing for different times (line b=5 minutes; line c=20 mins; line d=40 mins; and line e=60 minutes) are shown in FIG. 57. There was a clear power drop when $CO_2$ was flowing. To confirm this drop was due to the $CO_2$ absorption, the wavelength was fixed at 1572.5 nm and 1500 nm respectively, and then the real time output power was monitored. Ar and $CO_2$ were switched every 5 minutes. As FIG. 58A and FIG. 58B shown, the power drop was correlated to the $CO_2$ absorption. To further confirm the power drop was not due to the mechanical vibration of the optical fiber during the gas flow, the output power of 632 nm light was monitored, at which wavelength $CO_2$ should not have any absorption. As FIG. 58C shows, the output power randomly fluctuated, no matter whether Ar was flowing or $CO_2$ was flowing. This result confirms that the MOF-coated etched optical fiber can be used as a $CO_2$ sensor.

In view of the many possible embodiments to which the principles of the present disclosure may be applied, it should be recognized that the illustrated embodiments are only preferred examples of the present disclosure and should not be taken as limiting the scope of this disclosure. Rather, the scope of the present disclosure is defined by the following claims.

We claim:

1. A light guide comprising a section modified with a metal-organic framework material comprising a metal selected from copper, silver, gold, aluminum, zinc, cobalt, nickel, magnesium, manganese, iron, cadmium, beryllium, calcium, titanium, tin, chromium, vanadium, or a combination thereof; and an organic ligand selected from a mono-, di-, tri-, or tetra-valent ligand; wherein the light guide does not comprise a grating.

2. The light guide of claim 1, wherein the section of the light guide modified with the metal-organic framework material is further modified with a plasmonic nanomaterial comprising a metal oxide selected from an indium oxide, tin oxide, titanium oxide, zirconium oxide, cesium oxide, zinc oxide, copper oxide, or gallium oxide; and a dopant selected from Pt, Au, Sn, Al, Nb, or Ta.

3. The light guide of claim 1, wherein the section of the light guide modified with the metal-organic framework is an exposed core surface area of the light guide.

4. A method of determining the presence of a detectable species, comprising:
exposing a sample to the light guide of claim 1; and
analyzing the sample for a near-infrared signal produced by a detectable species absorbed by the metal-organic framework material of the light guide of claim 1.

5. The method of claim 4, wherein the sample is an environmental sample selected from a gas sample or an air sample.

6. The light guide of claim 1, wherein the light guide delivers near-infrared light.

7. The light guide of claim 1, wherein the light guide is a multi-mode optical fiber or a single-mode optical fiber.

8. The light guide of claim 1, wherein the section modified with the metal-organic framework material has a surface area ranging from 0.01% to 10% of the light guide.

9. The light guide of claim 1, wherein the section modified with the metal-organic framework material has a distance of 5 cm to 15 cm.

10. The light guide of claim 1, wherein the light guide comprises a plurality of sections modified with the metal-organic framework material.

11. The light guide of claim 2, wherein the plasmonic nanomaterial is fully encapsulated by the metal-organic framework material.

12. The light guide of claim 2, wherein the plasmonic nanomaterial is embedded within internal pores of the metal-organic framework material.

13. The light guide of claim 11, wherein the plasmonic nanomaterial is encapsulated within one or more layers of the metal-organic framework material.

14. The light guide of claim 1, wherein the light guide is physically coupled to the metal-organic framework material.

15. The light guide of claim 1, wherein the light guide is chemically coupled to the metal-organic framework material.

16. The light guide of claim 1, wherein a thin layer of the metal-organic framework material having a thickness ranging from 1 nm to less than 500 nm is coupled to the light guide.

17. The light guide of claim 1, wherein a thick layer of the metal-organic framework material having a thickness ranging from 500 nm to 50 μm is coupled to the light guide.

18. The light guide of claim 1, wherein the light guide detects gases at concentrations ranging from 100 ppm to 500 ppm.

19. The light guide of claim 1, wherein the light guide exhibits a response time of 0.1 seconds to 100 seconds.

* * * * *